US008748097B1

(12) United States Patent
O'Shea et al.

(10) Patent No.: US 8,748,097 B1
(45) Date of Patent: Jun. 10, 2014

(54) IDENTIFICATION OF AGENTS FOR TREATING CALCIUM DISORDERS AND USES THEREOF

(71) Applicants: President and Fellows of Harvard College, Cambridge, MA (US); Whitehead Institute for Biomedical Research, Cambridge, MA (US)

(72) Inventors: Erin O'Shea, Cambridge, MA (US); Timothy Peterson, Cambridge, MA (US); Thijn Brummelkamp, Amsterdam (NL); David M. Sabatini, Cambridge, MA (US)

(73) Assignees: President and Fellows of Harvard College, Cambridge, MA (US); Whitehead Institute for Biomedical Research, Cambrdge, MA (US)

( * ) Notice: Subject to any disclaimer, the term of this patent is extended or adjusted under 35 U.S.C. 154(b) by 0 days.

(21) Appl. No.: 13/692,993

(22) Filed: Dec. 3, 2012

Related U.S. Application Data

(60) Provisional application No. 61/566,470, filed on Dec. 2, 2011.

(51) Int. Cl.
*C12Q 1/68* (2006.01)
(52) U.S. Cl.
USPC ........... 435/6.1; 435/6.11; 435/7.1; 435/68.1; 435/69.1; 435/70.1
(58) Field of Classification Search
USPC .................. 435/6.1, 7.1, 68.1, 69.1, 70.1
See application file for complete search history.

(56) References Cited

U.S. PATENT DOCUMENTS

| | | | |
|---|---|---|---|
| 4,509,612 A | 4/1985 | Stuart | |
| 4,666,895 A | 5/1987 | Bosies et al. | |
| 4,683,195 A | 7/1987 | Mullis et al. | |
| 4,683,202 A | 7/1987 | Mullis | |
| 4,710,473 A | 12/1987 | Morris | |
| 4,711,843 A | 12/1987 | Chang | |
| 4,713,339 A | 12/1987 | Levinson et al. | |
| 4,719,203 A | 1/1988 | Bosies et al. | |
| 4,777,163 A | 10/1988 | Bosies et al. | |
| 4,800,159 A | 1/1989 | Mullis et al. | |
| 4,956,778 A | 9/1990 | Naito | |
| 4,958,839 A | 9/1990 | Guzik et al. | |
| 4,971,958 A | 11/1990 | Bosies et al. | |
| 5,002,937 A | 3/1991 | Bosies et al. | |
| 5,091,513 A | 2/1992 | Huston et al. | |
| 5,132,405 A | 7/1992 | Huston et al. | |
| 5,143,854 A | 9/1992 | Pirrung et al. | |
| 5,242,974 A | 9/1993 | Holmes | |
| 5,384,261 A | 1/1995 | Winkler et al. | |
| 5,405,783 A | 4/1995 | Pirrung et al. | |
| 5,409,818 A | 4/1995 | Davey et al. | |
| 5,412,087 A | 5/1995 | McGall et al. | |
| 5,424,186 A | 6/1995 | Fodor et al. | |
| 5,429,807 A | 7/1995 | Matson et al. | |
| 5,436,327 A | 7/1995 | Southern et al. | |
| 5,445,934 A | 8/1995 | Fodor et al. | |
| 5,472,672 A | 12/1995 | Brennan | |
| 5,527,681 A | 6/1996 | Holmes | |
| 5,529,756 A | 6/1996 | Brennan | |
| 5,532,128 A | 7/1996 | Eggers et al. | |
| 5,545,531 A | 8/1996 | Rava et al. | |
| 5,554,501 A | 9/1996 | Coassin et al. | |
| 5,554,527 A | 9/1996 | Fickenscher | |
| 5,556,752 A | 9/1996 | Lockhart et al. | |
| 5,561,071 A | 10/1996 | Hollenberg et al. | |
| 5,571,639 A | 11/1996 | Hubbell et al. | |
| 5,593,839 A | 1/1997 | Hubbell et al. | |
| 5,599,695 A | 2/1997 | Pease et al. | |
| 5,624,711 A | 4/1997 | Sundberg et al. | |
| 5,658,734 A | 8/1997 | Brock et al. | |
| 5,700,637 A | 12/1997 | Southern | |
| 5,747,251 A | 5/1998 | Carson et al. | |
| 5,807,522 A | 9/1998 | Brown et al. | |
| 5,837,832 A | 11/1998 | Chee et al. | |
| 5,962,273 A * | 10/1999 | Durmowicz et al. | ........ 435/91.1 |
| 6,004,755 A | 12/1999 | Wang | |
| 6,040,138 A | 3/2000 | Lockhart et al. | |
| 6,040,166 A | 3/2000 | Erlich et al. | |
| 6,045,996 A | 4/2000 | Cronin et al. | |
| 6,218,114 B1 | 4/2001 | Peck et al. | |
| 6,218,122 B1 | 4/2001 | Friend et al. | |
| 6,271,002 B1 | 8/2001 | Linsley et al. | |

(Continued)

FOREIGN PATENT DOCUMENTS

| | | |
|---|---|---|
| EP | 0252504 A1 | 1/1988 |
| EP | 0252505 A1 | 1/1988 |
| EP | 0320308 B1 | 11/1993 |

OTHER PUBLICATIONS

Ahmed, H., Principals and Reactions of Protein Extraction, Purification, and Characterization, CRC Press LLC (2005).
Arrington, S.A. et al., Temporal changes in bone mass and mechanical properties in a murine model of tumor osteolysis, Bone, 38(3):359-367 (2006).
Ausubel, F.M. et al., Short Protocols in Molecular Biology, 5th Edition, John Wiley & Sons, Inc. (2002).
Bi, Y., et al., Bisphosphonates Cause Osteonecrosis of the Jaw-Like Disease in Mice, The American Journal of Pathology, 177(1):280-290 (2010).
Bivi, N. et al., Identification of secondary targets of N-containing bisphosphonates in mammalian cells via parallel competition analysis of the barcoded yeast deletion collection, Genome Biology, 10(9):R93 (2009).

(Continued)

*Primary Examiner* — Ardin Marschel
(74) *Attorney, Agent, or Firm* — Choate, Hall & Stewart LLP; Brenda Herschbach Jarrell; Paul A. Nuzzi

(57) ABSTRACT

The present invention provides systems for identifying genes and gene products associated with nitrogenous bisphosphonate treatment (NBP) treatment of calcium disorders. The invention also provides systems for identify and/or characterizing agents in treating calcium disorders. The invention further provides systems for diagnosing a calcium disorder and monitoring treatment of a subject.

11 Claims, 20 Drawing Sheets

(56) References Cited

U.S. PATENT DOCUMENTS

| | | |
|---|---|---|
| 6,284,460 B1 | 9/2001 | Fodor et al. |
| 6,607,885 B1 | 8/2003 | Larossa et al. |
| 8,461,161 B2 * | 6/2013 | Burns et al. ............... 514/255.06 |

OTHER PUBLICATIONS

Bollag, D.M. et al., Protein Methods Second Edition, Wiley-Liss, Inc. (1996).
Brown, E.J. et al., A mammalian protein targeted by G1-arresting rapamycin-receptor complex, Nature, 369:756-758 (1994).
Bushman, F.D. et al., Host Cell Factors in HIV Replication: Meta-Analysis of Genome-Wide Studies, PLoS Pathogens, 5(5):1-12 (2009).
Carette, J.E. et al., Haploid Genetic Screens in Human Cells Identify Host Factors Used by Pathogens, Science, 326(5957):1231-1235 (2009).
Chen, J.J.W. et al., Profiling expression patterns and isolated differentially expressed genes by cDNA microarray system with colorimetry detection, Genomics, 51:313-324 (1998).
Clark, H.F. et al., The Secreted Protein Discovery Initiative (SPDI), a Large-Scale Effort to Identify Novel Human Secreted and Transmembrane Proteins: A Bioinformatics Assessment, Genome Research, 13:2265-2270 (2003).
Cote, R.J. et al., Generation of human monoclonal antibodies reactive with cellular antigens, Proceedings of the National Academy of Sciences, 80:2026-2030 (1983).
Czernik, A.J. et al., Phosphorylation State-Specific Antibodies, in Regulatory Protein Modification Techniques and Protocols, Neuromethods, 30:219-250 (1997).
Czernik, A.J. et al., Phosphorylation State-Specific Antibodies: Preparation and Applications, Neuroprotocols: A Companion to Methods in Neurosciences, 6:56-61 (1995).
Czernik, A.J. et al., Production of Phosphorylation State-Specific Antibodies, Methods in Enzymology, 201:264-283 (1991).
Echeverri, C.J. et al., High-throughput RNAi screening in cultured cells: a user's guide, Nature Reviews Genetics, 7:373-384 (2006).
Fire, A. et al., Potent and specific genetic interference by double-stranded RNA in *Caenorhabditis elegans*, Nature, 391:806-811 (1998).
Fisher, J.E. et al., Alendronate mechanism of action: geranylgeraniol, an intermediate in the mevalonate pathway, prevents inhibition of osteoclast formation, bone resorption, and kinase activation in vitro, Proceedings of the National Academy of Science, 96:133-138 (1999).
Hardy, R. et al., Bone loss in inflammatory disorders, Journal of Endocrinology, 201:309-320 (2009).
Harlow, E. et al., Antibodies: A Laboratory Manual, Cold Springs Harbor Laboratory (1988).
Harris, E.L.V. et al., Protein purification methods: A practical approach, IRL Press at Oxford University Press (1989).
Heitman, J. et al., Targets for cell cycle arrest by the immunosuppressant rapamycin in yeast, Science, 253(5022):905-909 (1991).
Holland, P.M. et al., Detection of specific polymerase chain reaction product by utilizing the 5'-3' exonuclease activity of *Thermus aquaticus* DNA polymerase, Proceedings of the National Academy of Sciences, 88:7276-7280 (1991).
Hosfield, D.J. et al., Structural Basis for Bisphosphonate-mediated Inhibition of Isoprenoid Biosynthesis, The Journal of Biological Chemistry, 279(10):8526-8529 (2004).
Huston, J.S. et al., Protein engineering of antibody binding sites: Recovery of specific activity in an anti-digoxin single-chain Fv analogue produced in *Escherichia coli*, Proceedings of the National Academy of Sciences, 85:5879-5883 (1988).
Inada, M. et al., Animal models for bone and joint disease. Ovariectomized and orchidectomized animals, Clinical Calcium, 21(2):164-170 (2011). Abstract.
Innis, M.A. et al., PCR Protocols: A Guide to Methods and Applications, Academic Press, Inc. (1990).
Itzstein, C. et al., The regulation of osteoclast function and bone resorption by small GTPases, Small GTPases, 2(3):117-130 (2011).
Jakoby, W.B. et al., Methods in Enzymology: Affinity Techniques—Enzyme Purification: Part B, vol. XXXIV: Methods in Enzymology series, Academic Press (1974).
Joos, S. et al., Mapping and chromosome analysis: the potential of fluorescence in situ hybridization, Journal of Biotechnology, 35:135-153 (1994).
Karsenty, G. Transcriptional control of skeletogenesis, Annual Review of Genomics and Human Genetics, 9:183-196 (2008).
Kavanagh, K.L. et al., The molecular mechanism of nitrogen-containing bisphosphonates as antiosteoporosis drugs, Proceedings of the National Academy of Sciences, 103(20):7829-7834 (2006).
Kimmel, A.R. et al., Preparation of cDNA and the Generation of cDNA Libraries: Overview, Methods in Enzymology, 152:307-316 (1987).
Kohler, G. et al., Continuous cultures of fused cells secreting antibody of predefined specificity, Nature, 256:495-497 (1975).
Kozbor, D. et al., Specific Immunoglobulin Production and Enhanced Tumorigenicity Following Ascites Growth of Human Hybridomas, Journal of Immunological Methods, 81:31-42 (1985).
Kricka, L.J. et al., Stains, labels and detection strategies for nucleic acids assays, Annals of Clinical Biochemistry, 39:114-129 (2002).
Kuehn, B.M., Long-term risks of bisphosphonates probed, The Journal of the American Medical Association, 301:710-711 (2009).
Lacey, D.L. et al., Osteoprotegerin Ligand is a Cytokine that Regulates Osteoclast Differentiation and Activation, Cell, 93(2):165-176 (1998).
Lam, J. et al., TNF-x induces osteoclastogenesis by direct stimulation of macrophages exposed to permissive levels of RANK ligand, The Journal of Clinical Investigation, 106(12):1481-1488 (2000).
Lerner, R.A., Tapping the immunological repertoire to produce antibodies of predetermined specificity, Nature, 299:592-596 (1982).
Liang, P. et al., Distribution and cloning of eukaryotic mRNAs by means of differential display: refinements and optimization, Nucleic Acid Research, 21(14):3269-3275 (1993).
Ma, Y. et al., Prevalence of off-target effects in *Drosophila* RNA interference screens, Nature, 443:359-363 (2006).
Mage, M. et al, Preparation of Fab and F(ab')2 Fragments from Monoclonal Antibodies, in Monoclonal Antibody Production Techniques and Applications, Marcel Dekker, Inc., pp. 79-97 (1987).
Mansfield, E.S. et al., Nucleic acid detection using non-radioactive labeling methods, Molecular and Cellular Probes, 9:145-156 (1995).
Masarachia, P. et al., Comparison of the distribution of 3H-alendronate and 3H-Etidronate in rat and mouse bones, Bone, 19(3):281-290 (1996).
Minkin, C. Bone acid phosphatase: tartrate-resistant acid phosphatase as a marker of osteoclast function, Calcified Tissue International, 34(3):285-290 (1982).
Monoclonal Antibody Purification, IBC Conference, May 16-17, 1996, La Jolla, California.
Morrison, S.L. et al., Chimeric human antibody molecules: Mouse antigen-binding domains with human constant region domains, Proceedings of the National Academy of Sciences, 81:6851-6855 (1984).
Mulder, N. J. et al., New developments in the InterPro database, Nucleic Acids Research, 35:D224-D228 (2007).
Mundlos, S. et al., Mutations Involving the Transcription Factor CBFA1 Cause Cleidocranial Dysplasia, Cell, 89:773-779 (1997).
Mundy, G.R., Bone resorption and turnover in health and disease, Bone, 8 suppl. 1:S9-16 (1987).
Mundy, G., Metastasis to bone: Causes, consequences and therapeutic opportunities, Nature Reviews Cancer, 2:584-593 (2002).
Nairn, A.C. et al., Serum antibodies that distinguish between the phospho- and dephospho-forms of a phosphoprotein, Nature, 299:734-736 (1982).
Neuberger, M.S. et al., Recombinant antibodies possessing novel effector functions, Nature, 312:604-608 (1984).
Ohara, O. et al., One-sided polymerase chain reaction: the amplification of cDNA, Proceedings of the National Academy of Sciences, 86:5673-5677 (1989).
Otto, F. et al., *Cbfa1*, a Candidate Gene for Cleidocranial Dysplasia Syndrome, is Essential for Osteoblast Differentiation and Bone Development, Cell, 89:765-771 (1997).

(56) References Cited

OTHER PUBLICATIONS

Paul, W.E. et al., Fundamental Immunology Third Edition, Raven Press, Ltd. (1993).

Raje, N. et al., Clinical, Radiographic, and Biochemical Characterization of Multiple Myeloma Patients with Osteonecrosis of the Jaw, Clinical Cancer Research, 14(8):2387-2395 (2008).

Roe, S., Protein Purification Techniques: A Practical Approach, Second Edition, Oxford University Press (2001).

Rosol, T.J. et al., Animal models of bone metastasis. Cancer, 97:748-757 (2003).

Sabatini, D.M. et al., RAFT1: a Mammalian Protein That Binds to FKBP12 in a Rapamycin-Dependent Fashion and is Homologous to Yeast TORs, Cell, 78:35-43 (1994).

Samadfam, R. et al., Co-Treatment of PTH With Osteoprotegerin or Alendronate Increases Its Anabolic Effect on the Skeleton of Oophorectomized Mice, Journal of Bone and Mineral Research, 22(1):55-63 (2007).

Sambrook, J. et al., Molecular Cloning: A Laboratory Manual, Second Edition, Cold Spring Harbor Laboratory Press (1989).

Sato, M. et al., Bisphosphonate action: alendronate localization in rat bone and effects on osteoclast ultrastructure, Journal of Clinical Investigation, 88:2095-2105 (1991).

Schaefer, B.C., Gene Cloning and Analysis: Current Innovations, Horizon Scientific Press (1997).

Schena, M. et al., Parallel human genome analysis: Microarray-based expression monitoring of 1000 genes, Proceedings of the National Academy of Sciences, 93:10614-10619 (1996).

Schena, M. et al., Quantitative Monitoring of Gene Expression Patterns with a Complementary DNA Microarray, Science, 270:467-470 (1995).

Stelzl, U. et al., A Human Protein-Protein Interaction Network: A Resource for Annotating the Proteome, Cell, 122:957-968 (2005).

Takeda, S. et al., Construction of chimaeric processed immunoglobulin genes containing mouse variable and human constant region sequences, Nature, 314:452-454 (1985).

Van Beek, E. et al., The Role of Geranylgeranylation in Bone Resorption and Its Suppression by Bisphosphonates in Fetal Bone Explants in Vitro: A Clue to the Mechanism of Action of Nitrogen-Containing Bisphosphonates, Journal of Bone and Mineral Research, 14(5):722-729 (1999).

Van Gijlswijk, R.P.M. et al., Universal Linkage System: versatile nucleic acid labeling technique, Expert Review of Molecular Diagnostics, 1(1):81-91 (2001).

Wilchek, M. et al., The Avidin-Biotin Complex in Bioanalytical Applications, Analytical Biochemistry, 171:1-32 (1988).

Yang, G. et al., Identification of the distinct promoters for the two transcripts of apoptosis related protein 3 and their transcriptional regulation by NFAT and NFαB, Molecular and Cellular Biochemistry, 302(1-2):187-194 (2007).

Yu, F. et al., Apoptosis related protein 3, an ATRA-upregulated membrane protein arrests the cell cycle at G1/S phase by decreasing the expression of cyclin D1, Biochemical and Biophysical Research Communications, 358(4):1041-1046 (2007).

Zhang, H. et al., Phosphoprotein Analysis Using Antibodies Broadly Reactive against Phosphorylated Motifs, The Journal of Biological Chemistry, 277(42):39379-39387 (2002).

Zhu, F. et al., Improved PCR-Based Subtractive Hybridization Strategy for Cloning Differentially Expressed Genes, BioTechniques, 29:310-313 (2000).

Zou, X. et al., NELL-1 Binds to APR3 Affecting Human Osteoblast Proliferation and Differentiation, FEBS Letters, 585(15)2410-2418 (2011).

\* cited by examiner

IDENTIFICATION OF AGENTS FOR TREATING CALCIUM DISORDERS AND USES THEREOF

CROSS REFERENCE TO RELATED APPLICATIONS

This application claims priority benefit under 35 U.S.C. §119 from U.S. patent application Ser. No. 61/566,470 filed Dec. 2, 2011, which is incorporated herein by reference.

BACKGROUND

As access to medical care continues to improve people are living longer. Yet, aging-associated diseases, such as calcium disorders, still present a barrier to increases in life expectancy and to improvements in the quality of life. Irregularities in calcium metabolism or homeostasis are linked to several pathological disorders, including osteoporosis, osteitis deformans, arthritis and osteolytic bone metastasis.

It is estimated that 10 million Americans have established osteoporosis and another 34 million have osteopenia, or low bone mass, accounting for approximately 1.5 million fractures annually. Bone metastases have also been shown to pose a major issue in many frequently occurring malignancies. Hypercalcemia, resulting from bone resorption, is an important complication of malignancy, causing most distressful symptoms, such as severe pain, spontaneous fractures, and in some cases metabolic coma and death. Moreover, studies have shown that neoplastic cell-induced osteolysis may determine the localization and provide growth enhancement of the tumor. (Mundy et. al., 1987, Bone, 8 supp. 1:S9-5; Rubin et al., 1985, Calcium in Biological Systems, Plenum Press, NY; both of which are hereby incorporated by reference).

SUMMARY

The present invention provides, among other things, systems for identifying and/or characterizing the molecular basis as well as cellular targets of a bisphosphonate agent. The present invention provides systems for identifying and/or designing agents that share some functional and/or mechanistic characteristics of a bisphosphonate agent. The present invention provides systems for identifying biomarkers whose level, form, and/or activity is associated with a disease, disorder, or condition associated with calcium disorders. The present invention further provides systems for the treatment of a subject with a calcium disorder.

Among other things the present invention provides systems for identifying and/or characterizing biological components (e.g., genes and/or factors encoded or regulated by them) that are associated with nitrogenous bisphosphonate (NBP) treatment of calcium disorders. The present invention encompasses the discovery of various biomarkers associated with NBP treatment. Without wishing to be bound by any particular theory, it is contemplated that biomarkers, may be used to detect or otherwise characterize one or more features of the pathological cascade, genes of interest, and/or mechanisms of action involved in NBP activity. Such biomarkers, whether used alone or in combination with one another and/or with one or more other features or agents, may permit characterization, understanding, and/or monitoring of NBP drugs and/or a subject's response to them. Biomarkers as described herein can be used to evaluate a subject suffering from or susceptible to a calcium disorder, to select a treatment regimen for such a subject, and/or to monitor and/or characterize such a treatment regimen and/or its progress.

Among other things the present invention provides systems for and/or characterizing a potential therapeutic that may be useful in medicine and in particular for treating a calcium disorder. In some embodiments, provided systems assess, for example, one or more pharmacological properties, efficacy, and/or toxicity of one or more analyzed agents. In some embodiments, provided systems compare one or more features (e.g., pharmacological properties, efficacy, toxicity etc) of tested compounds with that of one or more reference compounds (such as, for example, one or more of those NBP compounds listed in Table 1).

In some aspects, the present invention provides methods and/or reagents (e.g., supplied as kits) for determining level, form, and/or activity of one or more biomarkers associated with NBP therapy, as described herein. In some embodiments, such biomarkers are selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL1), NEL-like protein 2 (NELL2) and combinations thereof. In some embodiments, the protein C2orf28 (APR3) is referred to as Target of BisphOsphonate NitrogEnous (TBONE). As will be understood by those skilled in the art reading the present disclosure, the terms C2orf28, APR3 and TBONE are synonymous and can be used interchangeably with one another. In some embodiments, provided methods and/or reagents utilize (and/or provided kits include) one or more reference standards and/or control samples against which determined biomarker level, form, and/or activity is compared. In some embodiments, such a reference standard and/or control sample is or comprises a level, form, and/or activity of a particular biomarker in a normal sample (i.e., from a subject not suffering from a calcium disorder) or in an untreated sample (e.g., from a subject suffering from or susceptible to a calcium disorder but not receiving NBP therapy, or receiving different NBP therapy). In some embodiments, a reference standard or control sample is or comprises a historical level, form, and/or activity. In some embodiments, a reference standard or control sample is or comprises a level, form, and/or activity of a biomarker other than the one whose level, form, and/or activity is determined or is compared. In some embodiments, a reference standard or control sample is or comprises a level, form, and/or activity of a biomarker that is associated with or observed in one or more subjects suffering from or susceptible to a calcium disorder other than the one under analysis.

Thus, in some aspects, the invention provides the recognition that biomarkers selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL1), NEL-like protein 2 (NELL2) and combinations thereof are valuable targets for drug discovery. In some embodiments, the present invention demonstrates that C2orf28 (APR3) is a target of particular interest. In some embodiments, the present invention demonstrates that biomarkers involved in response to nitrogenous bisphosphonates, but not to bisphosphonates, are of particular interest. The present invention therefore provides the recognition that modulating expression, level, modification, and/or activity of such biomarkers, and particularly of C2orf28 is of high interest for purposes of treating calcium disorders and/or for beneficially altering bone cell metabolism, viability, and/or proliferation, e.g., in mammalian subjects. In some embodiments, the invention provides methods of identifying and/or characterizing agents that bind to and/or modulate expression, level, modification, form, or activity of one or more biomarkers selected from the group consisting of biomarkers selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL1), NEL-like protein 2 (NELL2) and combinations thereof (e.g., of a protein or transcript thereof). In some particular embodiments, the invention provides methods of identifying and/or characterizing agents that bind to and/or modulate expression, level, modification, form, or activity of C2orf28, e.g., C2orf28 mRNA or protein.

In some embodiments, the present invention relates to a calcium disorder selected from the group consisting of osteoporosis, osteitis deformans (Paget's disease), hyperparathyroidism, hypercalcemia of malignancy, arthritis, osteolytic bone metastasis, or combinations thereof.

In some embodiments, determining activity, and/or level comprises determining gene expression level. In some such embodiments, protein level, form, and/or activity is determined for one or more biomarkers. In some such embodiments, detection of protein level (form and/or activity) utilizes one or more reagents comprising one or more antibodies that specifically bind to the one or more biomarkers. In some embodiments, nucleic acid identity and/or level is determined; in some such embodiments, reactions that measure nucleic acid level of one or more biomarkers are used. In some such embodiments, one or more oligonucleotide probes is utilized, for example, that specifically hybridizes to mRNA of one or more biomarkers.

In one aspect the current invention provides systems for identifying and/or characterizing biological agents (e.g., genes and/or the entities they encode) whose level, form, and/or activity is associated with NBP treatment. In some embodiments, the present invention provides systems comprising: providing a population of cells, each of which shows altered level, form, and/or activity of a particular gene or gene product as compared with a parental cell; growing cells of the population under conditions of NBP exposure that cause a detectable effect on the parental cell; identifying cells of the population that lack the detectable effect; and determining which is the particular gene or gene product in the population cell that has altered level, form, and/or activity as compared with the parental cell. In some embodiments, the cells are haploid. In some embodiments, the cells are human. In some embodiments, the cells are human KBM7 cells. In some embodiments, the detectable effect is or comprises cell death. In some embodiments, the conditions of NBP exposure comprise NBP at a concentration that kills greater than 50% of the parental cells. In some embodiments, the conditions of NBP exposure comprise NBP at a concentration that kills greater than 75% of the parental cells. In some embodiments, the conditions of NBP exposure comprise NBP at a concentration that kills greater than 99% of the parental cells.

In some embodiments, the step of providing a population of cells that each have altered level, form, and/or activity of a particular gene or gene product as compared with a parental cell, comprises providing a population of parental cells and exposing them to a population of agents that each target a particular gene, for example under conditions that permit, on average, not more than one agent to enter a single cell and/or that permit, on average, not more than one genomic modification per cell. In some such embodiments, the agent comprises a retrovirus. In some such embodiments, the retrovirus is or comprises a gene-trap vector. In some embodiments, the retrovirus comprises a marker gene. In some embodiments, the marker gene is a drug resistance gene. In some embodiments, the drug resistance gene confers resistance to a drug selected from the group consisting of puromycin, hygromycin, streptomycin, kanamycin, and ampicillin. In some embodiments, the marker gene encodes a protein whose level or activity generates a detectable (e.g., fluorescent, chemiluminescent, radioactive, etc) signal. In some embodiments, the marker gene encodes a fluorescent protein. In some embodiments, the fluorescent protein is selected from the group consisting of green fluorescent protein (GFP), red fluorescent protein (RFP), yellow fluorescent protein (YFP), cyan fluorescent protein (CYP), mCherry, blue fluorescent protein (BFP), mTurquoise, mEGFP, mKO2, mVenus, and mApple.

In some aspects, the current invention provides methods for classifying and/or monitoring subjects who are suffering from or susceptible to a calcium disorder. For example, in some embodiments, the invention provides methods that involve determining in the subject (e.g., by obtaining and analyzing a sample from the subject) a level, form, and/or activity of a biomarker associated with NBP therapy and, in light of the determined level, form, and/or activity, classifying the subject as relatively likely or unlikely to have a particular response or reaction to NBP therapy, and/or as undergoing the particular response or reaction to such therapy. In some embodiments, the step of determining comprises determining that the subject expresses a level, form, and/or activity of the biomarker that is above or below a reference or threshold level established as correlated with the particular response or reaction to therapy.

In various embodiments, the present invention relates to one or more biomarkers and/or to use thereof. In some embodiments, the one or more biomarkers comprise at least one biomarker selected from the group consisting of C2orf28 (APR3), Phospholipase C-like 1(PLCL-1), Ephrin receptor B1 (EPHB1), Syntrophin Gamma 1(SNTG1), NELL1, NELL2, and combinations thereof. In some embodiments, the one or more biomarkers comprise at least two biomarkers selected the group consisting of C2orf28, Phospholipase C-like 1(PLCL-1), Ephrin receptor B1 (EPHB1), Syntrophin Gamma 1(SNTG1), NELL 1, NELL2 and combinations thereof. In some embodiments, the one or more biomarkers comprise at least three biomarkers selected from the group consisting of C2orf28, Phospholipase C-like 1(PLCL-1), Ephrin receptor B1 (EPHB1), Syntrophin Gamma 1(SNTG1), NELL1, NELL2, and combinations thereof. In some embodiments, the one or more biomarkers comprise C2orf28 (APR3), Phospholipase C-like 1(PLCL-1), Ephrin receptor B1 (EPHB1), Syntrophin Gamma 1(SNTG1), NELL1 and NELL2.

In some embodiments, level, form, and/or activity of one or more biomarkers is determined. In some embodiments, level, form, and/or activity is assessed by detecting and/or measuring biomarker protein. In some embodiments, biomarker protein is detected and/or measured using an antibody that specifically binds to the biomarker. In some embodiments, biomarker protein is detected and/or measured using gel electrophoresis (e.g., 2D-gel electrophoresis or mass spectrometry). In some embodiments, level, form, and/or activity is assessed by detecting and/or measuring biomarker nucleic acid. In some embodiments, hybridization is used to detect and/or measure biomarker nucleic acid. In some embodiments reverse transcription and/or primer extension is used to detect and/or measure biomarker nucleic acid. In some such embodiments, multiple rounds of reverse transcription and/or primer extension are employed (e.g., a polymerase chain reaction ["PCR"] is utilized). In some embodiments, Real Time PCR is employed.

In some embodiments, the current invention provides methods for treating a calcium disorder in a subject or system. In some embodiments, the subject or system comprises biomarker at a level, form, and/or activity that is associated with the calcium disorder. In some embodiments, the biomarker is or comprises a mutant version of at least one gene or protein, which mutant version is associated with the calcium disorder.

In some embodiments, the present invention provides methods that involve assessing entry of a NBP into cells. In some such embodiments, extent of entry is assessed for cells that show a level, form, and/or activity of at least one biomarker that is associated with a calcium disorder. In some embodiments, extent of entry is compared to a reference or control extent of entry into cells that show a level, form, and/or activity of the at least one biomarker that is not associated with the calcium disorder (e.g., that is associated with normal calcium metabolism). In some embodiments, extent of entry is used to classify a subject (e.g., a subject suffering from or susceptible to a calcium disorder and/or showing a biomarker level, form, and/or activity associated with a calcium disorder) as more or less likely to show (or as already showing) a particular response or reaction to NBP therapy. In some embodiments, extent of entry is used to assess effectiveness of treatment (e.g., NBP treatment or other treatment) of the calcium disorder. In some embodiments, extent of entry is assessed in a cell culture system (e.g., in a cell line). In some such embodiments, the cells are human. In some embodiments, extent of entry is assessed in an organism (e.g., via analysis of a biological sample of the organism).

In some embodiments, the present invention provides methods that involve assessing the effect of NBPs on components of the extracellular milieu. In some embodiments, this extracellular effect is assessed for cells that show an increase/ and or decrease in level, form, and/or activity of at least one biomarker that is associated with a calcium disorder. In some embodiments, the extracellular effect is compared to a reference or control extracellular effect, that shows an increase/ and or decrease in level, form, and/or activity of at least one biomarker that is not associated with a calcium disorder (e.g., that is associated with normal calcium metabolism). In some embodiments, change in extracellular effect may be used to determine a subject's response to NBP therapy. In some embodiments, extracellular effect may be assessed in an in vitro or in vivo system.

In some aspects, the current invention provides methods for evaluating agents (e.g., NBP agents) as drug candidates for treatment of a calcium disorder. In some embodiments, binding is assessed to a protein array, for example comprising at least one protein selected from the group consisting of C2orf28 (APR3), Phospholipase C-like 1(PLCL-1), Ephrin receptor B1 (EPHB1), Syntrophin Gamma 1(SNTG1), NELL1, NELL2 and combination thereof. In some embodiments, the agent(s) under evaluation are detectably labeled.

In some aspects, the current invention provides methods for evaluating a candidate agent for diagnosis, monitoring, and/or treatment of a calcium disorder. In some embodiments, the present invention provides methods comprising: contacting an agent with a protein selected from the group consisting of C2orf28 (APR3), NELL1, NELL2, Phospholipase C-like 1(PLCL-1), Ephrin receptor B1 (EPHB1), and Syntrophin Gamma 1(SNTG1) protein; and assessing binding of the agent to the protein, wherein binding of the agent to the protein indicates that the agent is a candidate agent for diagnosis, monitoring, and/or treatment of a calcium disorder. In some embodiemnts, the cotacting is performed in a cell-free system or cell lysate. In some embodiments, the protein is present in suspension. In some embodiments, the protein is bound to a solid support. In some embodiments, the support is a bead or chip.

In some embodiments, the contacting comprises contacting an agent with a cell that expresss a protein selected from the group consisting of C2orf28 (APR3), NELL1, NELL2, Phospholipase C-like 1(PLCL-1), Ephrin receptor B1 (EPHB1), Syntrophin Gamma 1(SNTG1) protein and/or combinations thereof. In some embodiments, the cell expresses one or more proteins selected from the group consisting of C2orf28 (APR3), NELL1, NELL2, Phospholipase C-like 1(PLCL-1), Ephrin receptor B1 (EPHB1) and Syntrophin Gamma 1(SNTG1).

In some embodiments, the method further comprises performing at least one assay to further evaluate the potential of a candidate agent as a diagnostic agent for a calcium disorder. In some embodiments, the at least one assay comprises: (i) measuring uptake of the agent by cells that express the protein; (ii) measuring uptake of the agent by cells that have increased or decreased expression of the protein as compared to suitable control cells; (iii) evaluating effect of the agent on at least one indicator of nitrogenous bisphosphonate activity; (iv) evaluating the effect of the agent on at least one indicator of bone cell survival, proliferation, apoptosis, or metabolism or at least one indicator of bone turnover, bone formation, or bone resorption in an ex vivo system or in a non-human animal; or (v) administering the agent to a non-human animal that serves as a model for a calcium disorder and evaluating the localization of the agent or the effect of the agent on one or more indicators bone turnover, bone formation, bone resorption, bone density, or one or more manifestations of the calcium disorder.

In some embodiments, the calcium disorder is characterized by abnormal bone formation as compared to that of a normal subject. In some embodiments, the calcium disorder is characterized by abnormal bone resorption as compared to that of a normal subject. In some embodiments, the calcium disorder is characterized by abnormal bone density as compared to that of a normal subject. In some embodiments the calcium disorder is selected from the group consisting of abnormal bone formation, bone resportion, bone density, or combination thereof, as compared to that of a normal subject. In some embodiments, the calcium disorder is a disorder for which nitrogenous bisphosphonate therapy is effective. In some embodiments, the calcium disorder is a disorder for which nitrogenous bisphosphonate therapy is selectively effective compared to treatment with non-nitrogenous bisphosphonate therapy. In some embodiments, the calcium disorders is selected from the group consisting of osteoporosis, osteitis deformans (Paget's disease), hyperparathyroidism, hypercalcemia of malignancy, arthritis, osteolytic bone lesion, osteolytic bone metastasis, osteopenia, osteogenesis imperfecta, or diffuse sclerosing osteomyelitis.

In some embodiments, the method comprises identify and/ or generating the agent. In some embodiments, the agent comprises a small molecule, antibody, lipid, polypeptide or nucleic acid. In some embodiments the agent is a mixture comprising one or more agents selected from the group consisting of small molecule, antibody, lipid, polypeptide or nucleic acid.

In some aspects, the current invention provides for a composition comprising: at least one isolated mammalian cell, wherein the at least one isolated mammalian cell is selected or modified to have altered expression, level, sequence, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product as compared with an otherwise comparable unselected or unmodified mammalian cell; and an agent selected from the group consisting of: small molecules, antibodies, lipids, polypeptides, and nucleic acids. In some embodiments, the agent is a small molecule. In some embodiments. the agent is a bisphosphonate. In some embodiments, the agent is a nitrogenous bisphosphonate. In some embodiments, the agent is a non-nitrogenous bisphosphonate. In some embodiments, the agent is not a bisphosphonate.

In some embodiments, the at least one mammalian cell is a haploid mammalian cell. In some embodiments, the mammalian cell is a cell line. In some embodiments, the cell line is the KBM7 cell line. In some embodiments, the mammalian cell has decreased expression of at least one protein selected from the group consisting of C2orf28 (APR3), NELL1, NELL2 Phospholipase C-like 1(PLCL-1), Ephrin receptor B1 (EPHB1), or Syntrophin Gamma 1(SNTG1) protein, as compared to a control cell. In some embodiments, the mammalian cell has increased expression of at least one protein selected from the group consisting of C2orf28 (APR3), NELL1, NELL2 Phospholipase C-like 1(PLCL-1), Ephrin receptor B1 (EPHB1), or Syntrophin Gamma 1(SNTG1) protein, as compared to a control cell. In some embodiments, the at least one mammalian cell is selected from the group consisting of osteoblast, osteocyte, osteoclast or combinations thereof. In some embodiments, the at least one mammalian cell is a co-culture comprising two or more cells selected from the group consisting of osteoblast, osteocyte, or osteoclast.

In some embodiments, the at least one mammalian cell is modified so that the cell expresses at least one protein selected from the group consisting of C2orf28 (APR3), NELL1, NELL2, Phospholipase C-like 1(PLCL-1), Ephrin receptor B1 (EPHB1), or Syntrophin Gamma 1(SNTG1). In some embodiments, the protein further comprises a detectable label or tag.

In some embodiments, the at least one mammalian cell is further selected or modified to have altered expression, level, sequence, modification, localization, or activity of one or more additional genes, wherein the one or more additional genes is associated with a calcium disorder or is associated with response to a therapeutic agent useful for treating a calcium disorder.

In some aspects, the present invention provides for a method of identifying a candidate agent for diagnosis, monitoring, and/or treatment of a calcium disorder comprising steps of: providing an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product; and testing the effect of the agent in a system that serves as a model for a calcium disorder, wherein the agent is identified as a candidate agent for treatment of a calcium disorder if the agent produces an effect in the system that is indicative of potential therapeutic efficacy for treatment of a calcium disorder. In some embodiments, the agent is not a bisphosphonate. In some embodiments, the agent is a nitrogenous bisphosphonate. In some embodiments, the agent is not C2orf28 (ARP3), NELL1, or NELL2 or a biologically active fragment or variant of C2orf28 (ARP3), NELL1, or NELL2. In some embodiments, the agent comprises a small molecule, antibody, polypeptide, lipid, nucleic acid or combinations thereof.

In some embodiments, the agent comprises an antibody. In some embodiments, the agent comprises a monoclonal antibody, antibody fragment, single chain antibody, bispecific antibody, diabody, tribody, tetrabody, nanobody, single domain antibody, VHH domain, human antibody, fully humanized antibody, partially humanized antibody, or chimeric antibody. In some embodiments, the agent is a polypeptide. In some embodiments, the polypeptide comprises an affibody, anticalin, or adnectin.

In some embodiments, the system comprises a cell culture comprising osteoclasts, osteoblasts, osteocytes, and/or a combination thereof. In some embodiments, the system comprises a non-human animal that serves as a model of a calcium disorder.

In some embodiments, the an effect indicative of potential therapeutic efficacy is an effect that would be produced in the system by a nitrogenous bisphosphonate present at a concentration that corresponds to a concentration that is therapeutically useful for treatment of a calcium disorder in a mammalian subject.

In some embodiments, providing an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product comprises identifying or generating an agent that binds to or modulates expression, level, modification, localization, or activity of said gene product.

In some embodiments, identifying an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product comprises screening at least 100, at least $10^3$, at least $10^4$, at least $10^5$, or at least $10^6$ agents.

In some embodiments, the agents are small molecules, wherein the small molecules are optionally members of a compound library. In some embodiments, the agents are antibodies, wherein an antibody is optionally a monoclonal antibody, antibody fragment, single chain antibody, bispecific antibody, diabody, tribody, tetrabody, nanobody, single domain antibody, VHH domain, human antibody, fully humanized antibody, partially humanized antibody, or chimeric antibody.

In some embodiments, identifying an agent that binds to a C2orf28 (APR3), NELL1, NELL2, Phospholipase C-like 1(PLCL-1), Ephrin receptor B1 (EPHB1), or Syntrophin Gamma 1(SNTG1) gene product comprises performing virtual screening using a library of small molecule structures and a three dimensional structure of at least a portion of a C2orf28 (APR3), NELL1, NELL2, Phospholipase C-like 1(PLCL-1), Ephrin receptor B1 (EPHB1), or Syntrophin Gamma 1(SNTG1) protein, thereby identifying a small molecule that binds to a C2orf28 (APR3), NELL1, or NELL2 protein.

In some aspects, the present invention provides for a method of treating a calcium disorder in a subject comprising administering to the subject an agent identified according to the method of: identifying a candidate agent for diagnosis, monitoring, and/or treatment of a calcium disorder comprising steps of: (a) providing an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product; and (b) testing the effect of the agent in a system that serves as a model for a calcium disorder, wherein the agent is identified as a candidate agent for treatment of a calcium disorder if the agent produces an effect in the system that is indicative of potential therapeutic efficacy for treatment of a calcium disorder. In some embodiments, the calcium disorder is characterized by abnormal bone formation, abnormal bone resorption, abnormal bone density, or a combination thereof, as compared to that of a normal subject. In some embodiments, the calcium disorder is a disorder for which nitrogenous bisphosphonate therapy is effective. In some embodiments, the calcium disorder is a disorder for which nitrogenous bisphosphonate therapy is effective, when compared to treatment with a non-nitrogenous bisphosphonate. In some embodiments, the calcium disorder is osteoporosis, osteitis deformans (Paget's disease), hyperparathyroidism, hypercalcemia of malignancy, arthritis, osteolytic bone lesion, osteolytic bone metastasis, osteopenia, osteogenesis imperfecta, or diffuse sclerosing osteomyelitis.

In some embodiments, the agent is not a bisphosphonate. In some embodiments, the agent is a nitrogenous bisphosphonate. In some embodiments, the agent is not C2orf28 (ARP3), NELL1, or NELL2 or a biologically active fragment or variant of C2orf28 (ARP3), NELL1, or NELL2. In some embodiments, the agent comprises a small molecule, antibody, polypeptide, lipid, nucleic acid or combinations thereof.

In some embodiments, the agent comprises an antibody. In some embodiments, the agent comprises a monoclonal antibody, antibody fragment, single chain antibody, bispecific antibody, diabody, tribody, tetrabody, nanobody, single domain antibody, VHH domain, human antibody, fully humanized antibody, partially humanized antibody, or chimeric antibody. In some embodiments, the agent is a polypeptide. In some embodiments, the polypeptide comprises an affibody, anticalin, or adnectin.

In some embodiments, the system comprises a cell culture comprising osteoclasts, osteoblasts, osteocytes, or a combination thereof. In some embodiments, the system comprises a non-human animal that serves as a model of a calcium disorder.

In some embodiments, the an effect indicative of potential therapeutic efficacy is an effect that would be produced in the system by a nitrogenous bisphosphonate present at a concentration that corresponds to a concentration that is therapeutically useful for treatment of a calcium disorder in a mammalian subject.

In some embodiments, providing an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product comprises identifying or generating an agent that binds to or modulates expression, level, modification, localization, or activity of said gene product.

In some embodiments, identifying an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product comprises screening at least 100, at least $10^3$, at least $10^4$, at least $10^5$, or at least $10^6$ agents.

In some embodiments, the agents are small molecules, wherein the small molecules are optionally members of a compound library. In some embodiments, the agents are antibodies, wherein an antibody is optionally a monoclonal antibody, antibody fragment, single chain antibody, bispecific antibody, diabody, tribody, tetrabody, nanobody, single domain antibody, VHH domain, human antibody, fully humanized antibody, partially humanized antibody, or chimeric antibody.

In some embodiments, identifying an agent that binds to a C2orf28 (APR3), NELL1, NELL2, Phospholipase C-like 1(PLCL-1), Ephrin receptor B1 (EPHB1), or Syntrophin Gamma 1(SNTG1) gene product comprises performing virtual screening using a library of small molecule structures and a three dimensional structure of at least a portion of a C2orf28 (APR3), NELL1, NELL2, Phospholipase C-like 1(PLCL-1), Ephrin receptor B1 (EPHB1), or Syntrophin Gamma 1(SNTG1) protein, thereby identifying a small molecule that binds to a C2orf28 (APR3), NELL1, or NELL2 protein.

In some aspects, the present invention provides for a pharmaceutically acceptable composition comprising an agent identified according to the method of: identifying a candidate agent for diagnosis, monitoring, and/or treatment of a calcium disorder comprising steps of: (a) providing an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product; and (b) testing the effect of the agent in a system that serves as a model for a calcium disorder, wherein the agent is identified as a candidate agent for treatment of a calcium disorder if the agent produces an effect in the system that is indicative of potential therapeutic efficacy for treatment of a calcium disorder. In some embodiments, the calcium disorder is characterized by abnormal bone formation, abnormal bone resorption, abnormal bone density, or a combination thereof, as compared to that of a normal subject. In some embodiments, the calcium disorder is a disorder for which nitrogenous bisphosphonate therapy is effective. In some embodiments, the calcium disorder is a disorder for which nitrogenous bisphosphonate therapy is effective, when compared to treatment with a non-nitrogenous bisphosphonate. In some embodiments, the calcium disorder is osteoporosis, osteitis deformans (Paget's disease), hyperparathyroidism, hypercalcemia of malignancy, arthritis, osteolytic bone lesion, osteolytic bone metastasis, osteopenia, osteogenesis imperfecta, or diffuse sclerosing osteomyelitis.

In some embodiments, the agent is not a bisphosphonate. In some embodiments, the agent is a nitrogenous bisphosphonate. In some embodiments, the agent is not C2orf28 (ARP3), NELL1, or NELL2 or a biologically active fragment or variant of C2orf28 (ARP3), NELL1, or NELL2. In some embodiments, the agent comprises a small molecule, antibody, polypeptide, lipid, nucleic acid or combinations thereof.

In some embodiments, the agent comprises an antibody. In some embodiments, the agent comprises a monoclonal antibody, antibody fragment, single chain antibody, bispecific antibody, diabody, tribody, tetrabody, nanobody, single domain antibody, VHH domain, human antibody, fully humanized antibody, partially humanized antibody, or chimeric antibody. In some embodiments, the agent is a polypeptide. In some embodiments, the polypeptide comprises an affibody, anticalin, or adnectin.

In some embodiments, the system comprises a cell culture comprising osteoclasts, osteoblasts, osteocytes, or a combination thereof. In some embodiments, the system comprises a non-human animal that serves as a model of a calcium disorder.

In some embodiments, the an effect indicative of potential therapeutic efficacy is an effect that would be produced in the system by a nitrogenous bisphosphonate present at a concentration that corresponds to a concentration that is therapeutically useful for treatment of a calcium disorder in a mammalian subject.

In some embodiments, providing an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product comprises identifying or generating an agent that binds to or modulates expression, level, modification, localization, or activity of said gene product.

In some embodiments, identifying an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product comprises screening at least 100, at least $10^3$, at least $10^4$, at least $10^5$, or at least $10^6$ agents.

In some embodiments, the agents are small molecules, wherein the small molecules are optionally members of a compound library. In some embodiments, the agents are antibodies, wherein an antibody is optionally a monoclonal antibody, antibody fragment, single chain antibody, bispecific antibody, diabody, tribody, tetrabody, nanobody, single domain antibody, VHH domain, human antibody, fully humanized antibody, partially humanized antibody, or chimeric antibody.

In some embodiments, identifying an agent that binds to a C2orf28 (APR3), NELL1, NELL2, Phospholipase C-like 1(PLCL-1), Ephrin receptor B1 (EPHB1), or Syntrophin Gamma 1(SNTG1) gene product comprises performing virtual screening using a library of small molecule structures and a three dimensional structure of at least a portion of a C2orf28 (APR3), NELL1, NELL2, Phospholipase C-like 1(PLCL-1), Ephrin receptor B1 (EPHB1), or Syntrophin Gamma 1(SNTG1) protein, thereby identifying a small molecule that binds to a C2orf28 (APR3), NELL1, or NELL2 protein. In some embodiments, the agent binds to or modulates expression, level, modification, localization, or activity of a C2orf28 (APR3) gene product.

In some embodiments, the pharmaceutically acceptable composition is produced using a method which comprises producing or purifying the agent or preparing a composition comprising the agent, wherein the produced or purified agent or composition is pharmaceutically acceptable for administration to a human or veterinary subject. In some embodiments, the In some embodiments, the gene, gene product or protein is a C2orf28 (APR3) gene, gene product, or protein.

In some aspects, the present invention provides for a composition comprising a plurality of test cells and a plurality of control cells, wherein the test cells and the control cells are genetically matched but differ with regard to their level of expression of C2orf28 (APR3), NELL1, NELL2, Phospholipase C-like 1(PLCL-1), Ephrin receptor B1 (EPHB1), or Syntrophin Gamma 1(SNTG1), and wherein the test cells and control cells are distinguishable based on expression or activity of one or more detectable labels.

In some embodiments, the composition further comprises an agent, wherein the agent is optionally selected from the group consisting of small molecules, polypeptides, lipids, nucleic acids, antibodies and/or combinations thereof.

In some embodiments, the test cells and control cells comprise different detectable labels, wherein at least one of the detectable labels is optionally a fluorescent protein.

In some aspects, the present invention provides for a method of identifying a candidate agent for diagnosis, monitoring, and/or treatment of a calcium disorder comprising contacting a composition comprising a plurality of test cells, with an agent for a suitable time period, measuring the relative number of test cells and control cells, and identifying the agent as a candidate agent for diagnosis, monitoring, and/or treatment of a calcium disorder if the agent differentially affects the number of test cells and control cells present in the composition.

In some embodiment, the composition comprising the plurality of test cells comprises both test cells and control cells which are genetically matched but differ with regard to their level of expression of C2orf28 (APR3), NELL1, NELL2, Phospholipase C-like 1(PLCL-1), Ephrin receptor B1 (EPHB1), or Syntrophin Gamma 1(SNTG1), and wherein the test cells and control cells are distinguishable based on expression or activity of one or more detectable labels. In some embodiments, the test cells and control cells comprise different detectable labels, wherein at least one of the detectable labels is optionally a fluorescent protein.

In some embodiments, the test cells have reduced or absent expression of C2orf28 (APR3), NELL1, NELL2, Phospholipase C-like 1(PLCL-1), Ephrin receptor B1 (EPHB1), or Syntrophin Gamma 1(SNTG1) as compared to the control cells, and wherein the agent is identified as a candidate agent for diagnosis, monitoring, and/or treatment of a calcium disorder if the agent affects survival and/or proliferation of the test cells to a lesser extent than the extent to which it affects survival or proliferation of the control cells.

In some aspects, the present invention provides for a kit comprising one or more reagents for measuring level, form, or activity of one or more biomarkers selected from the group consisting of C2orf28 (APR3), NELL1, NELL2, and combinations thereof; and a control level, or control sample for determining the control level, form or activity of the one or more biomarkers, wherein a comparison between the level, form, or activity of the one or more biomarkers in a sample obtained from a subject as compared with the control level is indicative of a subject's ability to respond to therapy with a nitrogenous bisphosphonate agent, for treating a calcium disorder. In some embodiments, the calcium disorder is characterized by abnormal bone formation, abnormal bone resorption, abnormal bone density, or a combination thereof, as compared to that of a normal subject. In some embodiments, the calcium disorder is a disorder for which nitrogenous bisphosphonate therapy is effective. In some embodiments, the calcium disorder is selected from the group consisting of osteoporosis, osteitis deformans (Paget's disease), hyperparathyroidism, hypercalcemia of malignancy, arthritis, osteolytic bone lesion, osteolytic bone metastasis, osteopenia, osteogenesis imperfecta, or diffuse sclerosing osteomyelitis.

In some embodiments, the one or more reagents comprises one or more antibodies that specifically bind to the one or more biomarkers. In some embodiments, the one or more reagents are of use to measure nucleic acid expression level of the one or more biomarkers. In some embodiments, the one or more reagents comprise one or more oligonucleotide probes or primers that specifically hybridize to the mRNA (or a complement thereof) of the one or more biomarkers.

In yet another aspect, the invention provides for a method of identifying a subject responsive to nitrogenous bisphosphonate treatment for treating a calcium disorder comprising providing a subject having or suspected of having a calcium disorder; collecting a biological sample from the subject; and measuring level, form, modification state, and/or activity of one or more biomarkers in the sample, wherein the level, form, modification state, and/or activity of the one or more biomarkers is indicative of a subject's ability to respond to nitrogenous bisphosphonate treatment. In some embodiments, the calcium disorder is characterized by abnormal bone formation, abnormal bone resorption, abnormal bone density, or a combination thereof, as compared to that of a normal subject. In some embodiments, the calcium disorder is a disorder for which nitrogenous bisphosphonate therapy is effective. In some embodiments, the calcium disorder is selected from the group consisting of osteoporosis, osteitis deformans (Paget's disease), hyperparathyroidism, hypercalcemia of malignancy, arthritis, osteolytic bone lesion, osteolytic bone metastasis, osteopenia, osteogenesis imperfecta, or diffuse sclerosing osteomyelitis.

In some embodiments, the one or more biomarkers comprise at least one biomarker selected from C2orf28 (APR3), NELL1, NELL2, Phospholipase C-like 1(PLCL-1), Ephrin receptor B1 (EPHB1), and Syntrophin Gamma 1(SNTG1). In some embodiments, the one or more biomarkers comprise at least two biomarker selected from C2orf28 (APR3), NELL1, NELL2, Phospholipase C-like 1(PLCL-1), Ephrin receptor B1 (EPHB1), and Syntrophin Gamma 1(SNTG1). In some embodiments, the one or more biomarkers comprise at least three biomarker selected from C2orf28 (APR3), NELL1, NELL2, Phospholipase C-like 1(PLCL-1), Ephrin receptor B1 (EPHB1), and Syntrophin Gamma 1(SNTG1). In some embodiments, the one or more biomarkers comprise C2orf28 (APR3).

In some embodiments, the protein expression level of the one or more biomarkers is measured. In some embodiments, the protein expression level is measured by performing an immunoassay using one or more antibodies that specifically bind the one or more biomarkers. In some embodiments, the protein expression level is measured by performing gel electrophoresis or mass spectrometry. In some embodiments, the nucleic acid expression level of the one or more biomarkers is measured. In some embodiments, the nucleic acid expression level of the one or more biomarkers is measured by hybridization. In some embodiments, the nucleic acid expression level of the one or more biomarkers is measured by RT-PCR amplification. In some embodiments, the biological sample comprises or is derived from cells or tissue.

BRIEF DESCRIPTION OF THE DRAWING

The drawing is for illustration purposes only, and not for limitation.

DEFINITIONS

Figure 1:
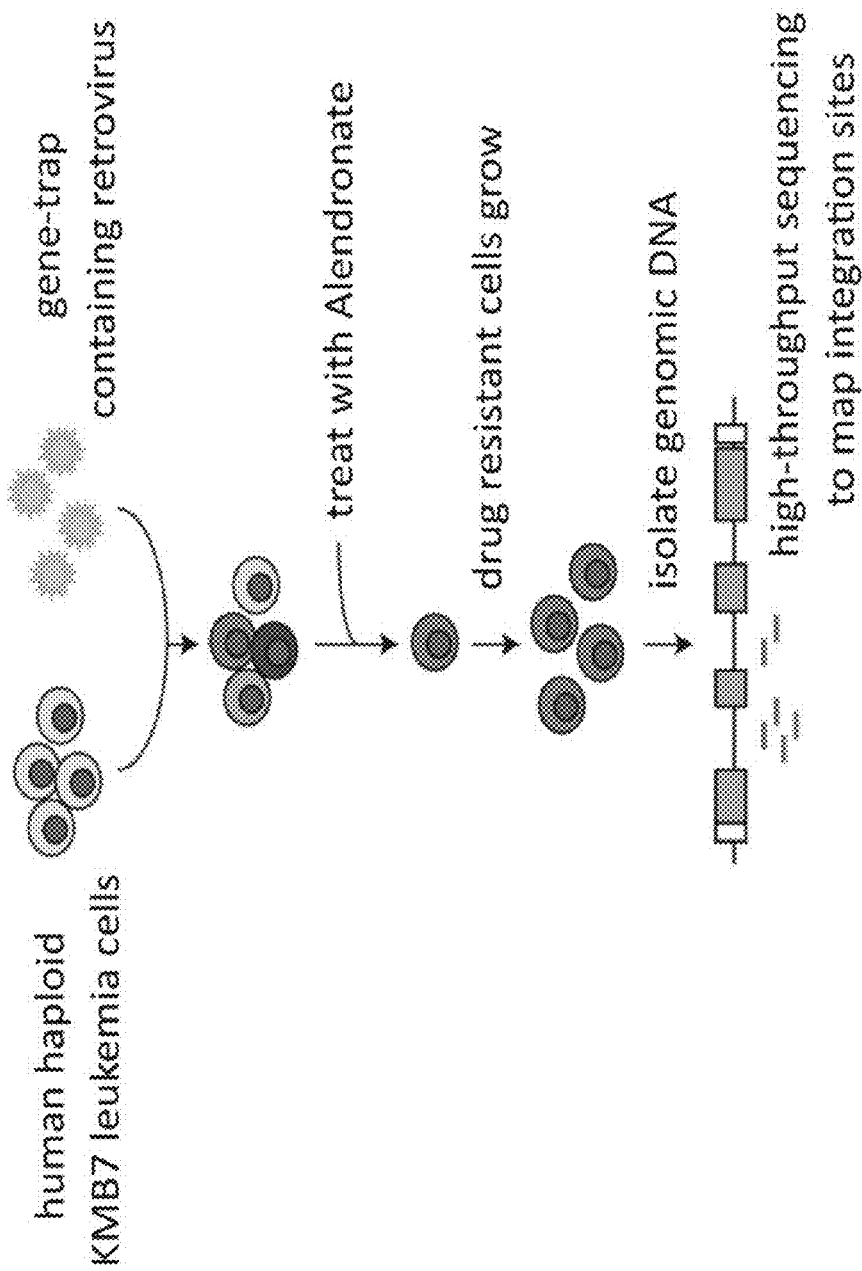
FIG. 1. High-throughput Screen for Gene Identification. Schematic representation of a high-throughput screen for identifying genes involved in subject response to NBP treatment.

In order for the present invention to be more readily understood, certain terms are first defined. Additional definitions for the following terms and other terms are set forth throughout the specification.

Agent: The term "agent" refers to any entity, whether naturally occurring or non-naturally occurring (e.g., synthetic, recombinant, or otherwise produced or modified using the hand of man) that has designated structural and/or functional attributes. An agent may comprise a single molecule, or a complex of individual molecules, typically in physical association with one another. In some embodiments, an agent is or comprises a biological macromolecule (e.g., a nucleic acid, polypeptide or protein, lipid, or carbohydrate); alternatively or additionally, in some embodiments, an agent is or comprises one or more small organic or inorganic molecules. In some embodiments, an agent is or comprises an extract of a material such as bacterial, plant, fungal, or animal (particularly mammalian, including human) cells or tissues.

Amplify: The term "amplify" is used herein in the broad sense to mean generating or increasing. In some embodiments, the term "amplify", refers to production of multiple copies of an agent or signal. In some embodiments, the agent is a nucleic acid. In some embodiments, the agent or signal is other than a nucleic acid (e.g., is or comprises a fluorescent signal).

Antibody: As used herein, the term "antibody" has its art-understood meaning and refers to an immunoglobulin polypeptide or complex. An antibody may be of any immunoglobulin class such as, for example, IgG, IgM, IgA, IgD and IgE. An antibody may be monoclonal or polyclonal. Human antibodies reproduced in nature as tetramers of two "light" chains (about 25 kD) and two "heavy" chains (about 50-70 kD). The N-terminus of each chain defines a variable region of about 100 to 110 or more amino acids primarily responsible for antigen recognition. The terms "variable light chain" (VL) and "variable heavy chain" (VH) refer to these variable regions of light and heavy chains, respectively. An antibody is typically specific for a particular antigen or set of antigens. In some embodiments, the term "antibody" encompasses or refers to a fragment of an antibody tetramer. Examples of antibody fragments include, but are not limited to, Fab, Fab', F(ab')2, scFv, Fv, dsFv diabody, and Fd fragments. An antibody fragment in accordance with the present invention may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. An antibody or antibody fragment may optionally comprise a single polypeptide chain. Alternatively or additionally, an antibody fragment may comprise multiple chains that are linked together, for example, by disulfide linkages. In some embodiments, antibodies are single chain antibodies, such as single chain Fv (scFv) antibodies in which a variable heavy and a variable light chain are joined together (directly or through a peptide linker) to form a continuous polypeptide. A single chain Fv ("scFv") polypeptide is a covalently linked VH::VL heterodimer which may be expressed from a nucleic acid including VH- and VL-encoding sequences either joined directly or joined by a peptide-encoding linker. (See, e.g., Huston, et al. (1988) Proc. Nat. Acad. Sci. USA, 85:5879-5883, the entire contents of which are herein incorporated by reference.) A number of strategies exist for converting naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778. In some embodiments, an antibody is or comprises a VHH (i.e., an antigen-specific VHH) antibody that comprises only a heavy chain. In some embodiments, a provided binding agent is or comprises one or more "mini-antibodies" or "minibodies", which are sFv polypeptide chains that include oligomerization domains at their C-termini, separated from the sFv by a hinge region. In some embodiments, the hinge region comprises a self-associating alpha-helix or leucine zipper, which may or may not be further stabilized by additional disulfide bonds. In some embodiments, an antibody fragment shares one or more functional attributes (e.g., binding specificity and/or affinity) of a corresponding complete or intact antibody. Typically, an antibody fragment, as that term is used herein, comprises at least about 50 amino acids and more typically comprises at least about 200 amino acids. In some embodiments, an antibody may be a human antibody. In some embodiments, an antibody may be a humanized antibody.

Array: The terms "array", "micro-array", and "biochip" are used herein to refer to an arrangement, on a substrate surface, of hybridizable array elements, such as multiple nucleic acid molecules or proteins of known sequences. Each nucleic acid molecule or protein is immobilized to a discrete spot (i.e., a defined location or assigned position) on the substrate surface. The term "micro-array" more specifically refers to an array that is miniaturized so as to require microscopic examination for visual evaluation.

Associated with: As defined herein, the term "associated with" refers to an entity that is statistically correlated with one or more attributes of a disease, disorder or condition such as, for example, presence of and/or susceptibility to the disease, disorder, or condition. In some embodiments, the attributes of a disease, disorder or condition may include, for example, successful outcome, incidence or severity of a particular side effect, extent of progress, presence of and/or susceptibility to the disease, disorder or condition, and/or likelihood of a particular response or reaction to therapy.

Bisphosphonate Agent: As defined herein, the term "bisphosphonate Agent" refers to a class of compounds characterized by two C—PO3-2 bonds and having the general structure:

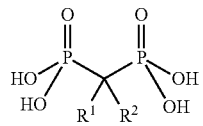

wherein R1 and R2 are independently selected from the group consisting of hydrogen, hydroxy, halogen, amino, SH, phenyl, alkyl, mono- or dialkylamino, mono- or dialkylaminoalkyl, alkoxy, thioalkyl, thiophenyl, and aryl or heteroaryl moieties selected from the group consisting of phenyl, pyridyl, furanyl, pyrrolidinyl, imidazolyl, and benzyl, wherein the aryl or heteroaryl moiety is optionally substituted with alkyl. It some embodiments the term "bisphosphonate" as used herein encompasses diphosphonates, biphosphonic acids, and diphosphonic acids, as well as salts and derivative of these materials. In some embodiments, the term "bisphosphonate" denotes a class of pharmaceutical compounds which resemble pyrophosphate analogues and are active in reducing bone resorption. "Non-Nitrogenous Bisphosphonates" lack nitrogen and include, but are not limited to, etidronate, clodronate, tiludronate and pharmaceutically acceptable salts thereof "Nitrogenous Bisphosphonates" (NBPs), contain nitrogen and include, but are not limited to, Alendronate, Cimadronate, Ibandronate, Risedronate, Piridronate, Pamidronate, Zolendronate, Neridronate, Olpadronate, and pharmaceutically acceptable salts thereof. In some embodiments, NBPs include pharmaceutical agents described, for example, in U.S. Pat. No. 4,509,612, U.S. Pat. No. 4,666,895, U.S. Pat. No. 4,719,203, EP-A-252,504, EP-A-252,505, U.S. Pat. No. 4,777,163, U.S. Pat. No. 5,002,937, U.S. Pat. No. 4,971,958 and U.S. Pat. No. 4,958,839, each of which is incorporated herein by reference in its entirety.

Biomarker. As defined herein, the term "biomarker" refers to an agent whose level, form, and/or activity is "associated with" a disease, disorder, or condition. In some embodiments, a biomarker is a protein whose level, form, and/or activity correlates with one or more attributes of the disease; in some embodiments a biomarker is a nucleic acid; in some embodiments the biomarker is deoxyribonucleic acid; in some embodiments the biomarker is ribonucleic acid. In many embodiments, a biomarker has at least one characteristic that can be objectively measured and/or evaluated (e.g., quantified). In some embodiments, a biomarker is an organic biomolecule which is differentially present and/or active in a sample taken from a subject of one phenotypic status (e.g., having a disease) as compared with another phenotypic status (e.g., not having the disease). In some embodiments, a biomarker is considered to be differentially present and/or active between different phenotypic statuses if the mean or median expression and/or activity level of the biomarker in the different groups is calculated to be statistically significant. Common tests for statistical significance include, among others, t-test, ANOVA, Kruskal-Wallis, Wilcoxon, Mann-Whitney, odds ratio, Linear Discriminant Analysis, Quadratic Discriminant Analysis and K-nearest neighbor. Biomarkers, alone or in combination, provide measures of relative risk that a subject belongs to one phenotypic status or another. Therefore, they are useful as markers for disease (diagnostics), therapeutic effectiveness of a drug (theranostics), predicting the likelihood of developing a disease (prognostic) and drug toxicity.

In some embodiments, a biomarker is or comprises a mutant version of a gene or protein, which mutant version is associated with a calcium disorder. In some embodiments, such a mutant version is (or encodes) a mutant protein kinase that shows reduced activity as compared to the wild-type version. In some embodiments, such a mutant version is (or encodes) a mutant protein phosphatase that shows reduced phosphatase activity as compared to the wild-type version. In some embodiments, such a mutant version is (or encodes) a protein that is differently modified (e.g., glycosylated, phosphorylated, lapidated, disulfide bonded, etc) as compared to the wild-type version. In some embodiments, such a mutant version is (or encodes) a protein that is differently localized within a cell as compared to the wild-type version.

Binding agent: As used herein, the term "binding agent" refers to any agent that binds to, and in some embodiments binds specifically to, a designated target (e.g., an antigen or a target protein or peptide). In some embodiments, a binding agent forms a complex with its target and elicits a biological response (e.g., agonize or antagonize a particular biological activity). In some embodiments, a binding agent is or comprises a polypeptide, or portion thereof. In some embodiments, a binding agent is or comprises an antibody or antibody fragment. In some embodiments, a binding agent is a scaffold protein such as, but is not limited to, protein A, lipoclins, ankryin consensus repeat domain, thioredoxin, adnectin, anticalins, affibodies, centyrin, avimer domains, ubiquitin, zinc finger DNA-binding proteins (ZEPs), or IgNARs. In some embodiments, a binding agent is a scaffold protein, in which the scaffold protein is engineered to display one or more CDRs. In some embodiments, a provided binding agent is or comprises a cystine-knot miniprotein. In some embodiments, a provided binding agent is or comprises an avibody (diabody, tribody, tetrabody). In some embodiments, a provided binding agent is or comprises a Scorpion, wherein the Scorpion structure comprises two binding moieties separated by an immunoglobulin Fc domain. In some embodiments, a provided binding agent is or comprises a peptidomimetic. In some embodiments, a binding agent is or comprises a nucleic acid. In some embodiments, a binding agent is or comprises a nucleic acid, such as DNA or RNA. In some embodiments, a binding agent comprises one or more oligonucleotides. In some embodiments, a binding agent is or comprises one or more oligonucleotides comprising a secondary structure such as loop, hairpin, fold or combinations thereof. In some embodiments, a binding agent is or comprises one or more oligonucleotides comprising a higher ordered (tertiary or quaternary) structure. In some embodiments a binding agent is or comprises a nucleic acid that forms a structure designed to mimic an epitope found within its target. In some embodiments, a binding agent is or comprises an aptamer. In some embodiments, a binding agent is or comprises a glycan. In some embodiments, a binding agent is or comprises a small molecule.

Biological Sample: As used herein, the term "biological sample" is or comprises tissue, cells, bodily fluid, or components thereof. I some embodiments, a biological sample is a primary sample obtained from a subject. In some embodiments, a biological sample is prepared from a primary sample, for example, by separating and/or amplifying (e.g., by culturing or otherwise duplicating) one or more components of the primary sample. In some embodiments, a primary sample is or comprises amniotic fluid, blood (e.g., whole blood, serum, plasma), cerebrospinal fluid ("CSF"), saliva, stool, tears, urine, and combinations thereof. In some embodiments, a primary sample is obtained by biopsy or other needle extraction, swab, and/or other sampling methodology. In some embodiments, primary samples are obtained by, for example, scraping cells from the surface of the buccal cavity. In some embodiments, a "sample" is prepared by processing (i.e., manipulating by the hand of man) a primary sample, for example by separating different components present in the primary sample, culturing cells present in the primary sample, etc. In some embodiments, such processing includes releasing or otherwise making available a nucleic acid for detection as described herein. Suitable samples may be obtained from a stage of life such as a fetus, young adult, adult (e.g., pregnant women), and the like. Alternatively or additionally, fixed or frozen tissues may be used.

Calcium disorder: The terms "calcium disorder" and "calcium disease" are used herein to refer to diseases, disorders or conditions associated with and/or affected by activity of bisphosphonate agents. In some embodiments, a calcium disorder is characterized by abnormal calcium and/or phosphate metabolism. For example, in some embodiments, a calcium disorder is characterized by anomalous mobilization of calcium and/or phosphate. Such anomalous mobilization can lead to general or specific bone loss or excessive high calcium and/or phosphate levels, for example in the fluids and/or tissues of the body. In some embodiments, anomalous mobilization can result in pathological hard tissue demineralization. Particular examples of certain calcium disorders that may involve anomalous mobilization include, but are not limited to, osteoporosis, osteopenia, osteitis deformans (Paget's disease), hyperparathyroidism, hypercalcemia of malignancy, arthritis, rheumatoid arthritis, cancer therapy, osteolytic bone metastasis, breast cancer and periodontal disease. Alternatively or additionally, in some embodiments a calcium disorder is characterized by deposition of calcium and/or phosphate anomalously in the body. In some embodiments, such calcium disorders may be described as involving pathologic calcification. Particular examples of such conditions include, but are not limited to, myositis ossificans progressive, calcinosis univeralis, arthritis, neuritis, bursitis, tendonitis, kidney and renal calculus, bioprosthetic and prosthetic heart valves, artherosclerosis, and/or other inflammatory conditions which predispose involved tissue to deposition of calcium phosphates. In some embodiments a calcium disorder is characterized by abnormal bone formation, abnormal bone resorption, abnormal bone density, or a combination thereof, as compared to a normal level of bone formation, bone resorption, or bone density. In some embodiments a calcium disorder is osteogenesis imperfecta, a heterogeneous genetic disease resulting from mutations within the collagen type 1 genes (COL1a1 and COL1a2). Osteogenesis imperfect is characterized by bone fragility, skeletal deformity, growth retardation, and in some instances, death. In some aspects, OI has a prenatal onset and may be diagnosed prenatally. In some embodiments a calcium disorder is diffuse sclerosing osteomyelitis, a condition that causes sclerosis, predominantly in the long bones and mandible, and is characterized by excess bone deposition. Alternatively or additionally, in some embodiments a calcium disorder is characterized by diseases, disorders or conditions associated with and/or affected by activity of bisphosphonate agents. Particular examples of such conditions included, but are not limited to, multiple myeloma and metastatic carcinoma. In some embodiments, the metastatic carcinoma is from a primary site such as, but not limited to, prostate, breast, skin, lung, kidney, intestine and thyroid, and has metastasized to the bone. In some embodiments a calcium disorder is any disorder, disease, or condition that may be effectively treated using a nitrogenous bisphosphonate.

Characteristic portion: As used herein, the phrase a "characteristic portion" of a protein or polypeptide is one that contains a continuous stretch of amino acids, or a collection of continuous stretches of amino acids, that together are characteristic (i.e., are a "characteristic sequence") of a protein or polypeptide. Each such continuous stretch generally will contain at least two amino acids. Furthermore, those of ordinary skill in the art will appreciate that typically at least 5, 10, 15, 20 or more amino acids are required to be characteristic of a protein. In general, a characteristic portion is one that, in addition to sharing the characteristic sequence, shares at least one functional characteristic with the relevant intact protein.

Characteristic sequence: A "characteristic sequence" is a sequence that is found in all members of a family of polypeptides or nucleic acids, and therefore can be used by those of ordinary skill in the art to define members of the family.

Combination Therapy: The term "combination therapy", as used herein, refers to those situations in which two or more different agents are administered in overlapping regimens so that the subject is simultaneously exposed to both agents.

Control: As used herein, the term "control" has its art-understood meaning of being a standard against which results are compared. In some embodiments, a control is a reaction or assay that is performed simultaneously with a test reaction or assay to provide a comparator. In one assay, the "test" (i.e., the variable being tested) is applied. In another assay, the "control," the variable being tested is not applied. In some embodiments, a control is or comprises a historical control (i.e., of a test or assay performed previously, or an amount or result that is previously known). In some embodiments, a control is or comprises a printed or otherwise saved record. A control may be a positive control or a negative control. In some embodiments, a "control individual" is an individual afflicted with the same form of calcium disorder as the individual being treated, who is about the same age as the individual being treated (to ensure that the stages of the disease in the treated individual and the control individual(s) are comparable).

Diagnosis: As used herein, the term "diagnosis" refers to a process aimed at determining if an individual is afflicted with a disease or ailment. In the context of the present invention, "diagnosis" of a "calcium disorder" refers to a process aimed at determining if an individual is afflicted with a disease associated with or resulting from a disruption in calcium metabolism. Any appropriate technique(s) may be utilized to achieve diagnosis. In some embodiments, one or more of the following is utilized: physical observation, blood based test, enzyme based test, imaging based test, functional imaging based test, x-ray based assay, antibody based test, nucleic acid based test, protein based test, chemical analysis of a biological fluid or tissue and any other methods know to those skilled in the art.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses.

Effective amount: As used herein, the term "effective amount" refers to an amount or concentration of a compound or agent that is sufficient to fulfill its intended purpose(s). In the context of the present invention, the purpose(s) may be, for example: to modulate the levels of calcium metabolism in a subject suffering from a calcium disorder to, alter the state of the disorder in a subject, reduce progression of the disorder in a subject, prevent or delay onset of the disorder in a subject, reduce incidence and/or severity of one or more symptoms associated with the disorder in a subject, or completely ameliorate the disorder in the subject.

Hybridizing: The term "hybridizing" refers to the binding of two single stranded nucleic acids via complementary base pairing. The term "specific hybridization" refers to a process in which a nucleic acid molecule preferentially binds, duplexes, or hybridizes to a particular nucleic acid sequence under stringent conditions (e.g., in the presence of competitor nucleic acids with a lower degree of complementarity to the hybridizing strand). In certain embodiments of the present invention, these terms more specifically refer to a process in which a nucleic acid fragment (or segment) from a test sample preferentially binds to a particular probe and to a lesser extent or not at all, to other probes, for example, when these probes are immobilized on an array.

Improve, increase, or reduce: As used herein, the terms "improve," "increase" or "reduce," or grammatical equivalents, indicate values that are relative to a baseline, reference, or control measurement, such as a measurement in the same individual prior to initiation of the treatment described herein, or a measurement in a control individual (or multiple control individuals) in the absence of the treatment described herein.

In combination: The phrase "in combination", as used herein, refers to agents that are simultaneously administered to a subject. It will be appreciated that two or more agents are considered to be administered "in combination" whenever a subject is simultaneously exposed to both (or more) of the agents. Each of the two or more agents may be administered according to a different schedule; it is not required that individual doses of different agents be administered at the same time, or in the same composition. Rather, so long as both (or more) agents remain in the subject's body, they are considered to be administered "in combination".

Kit: As used herein, the term "kit" refers to a set of materials provided together, typically for use in a common context. In some embodiments, a kit may comprise reaction reagents (e.g., nucleic acids, enzymes, buffers, etc), one or more systems that allow for the storage, transport, or delivery of reaction reagents (e.g., tubes, boxes, or other containers) and/or supporting materials (e.g., written instructions for performing assays etc.). For example, in some embodiments, kits include one or more enclosures (e.g., boxes) containing relevant reaction reagents and/or supporting materials. As used herein, the term "fragmented kit" refers to comprising set of two or more separate containers that each contain a sub portion of the total kit components. In some embodiments, such containers are delivered to an intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contain a sub portion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Label: As used herein, the term "label" as used herein refers to any entity that provides a detectable (preferably quantifiable) signal. In some embodiments, a label has a structure that permits attachment to an agent to be detected (e.g., a nucleic acid, protein, drug, etc). In some embodiments, a label provides a signal selected from the group consisting of fluorescence, radioactivity, color, enzymatic activity, magnetism, charge, etc. In some embodiments, a label is detectable, for example, by gravimetry, X-ray diffraction or absorption, fluorescence microscopy, etc. In some embodiments, a label is or comprises a charged moiety (positive or negative charge); in some embodiments, a label is charge neutral. In some embodiments, a label is or comprises a particular nucleic acid or protein sequence.

Normal: As used herein, the term "normal," when used to modify the term "individual" or "subject" refers to an individual or group of individuals who does not have a particular disease or condition and is also not a carrier of the disease or condition. In some embodiments, the term "normal" is used herein to qualify a biological specimen or sample isolated from a normal or wild-type individual or subject, for example, a "normal biological sample." In some embodiments, a normal individual or sample is used as a reference or control against which other samples are compared.

Nucleic Acid: As used herein refers to an oligonucleotide, nucleotide or polynucleotide. In some embodiments, a nucleic acid is or comprises DNA; in some embodiments, a nucleic acid is or comprises RNA. In some embodiments, a nucleic acid is or has a sequence identical to a genomic nucleic acid. In some embodiments, nucleic acid is prepared chemically or synthetically. In some embodiments, a nucleic acid is double stranded. In some embodiments, a nucleic acid is or comprises one or more single stranded regions. In some embodiments, a nucleic acid has one or more nicks. In some embodiments, the nucleic acid is double stranded in a continuous circular plasmid. In some embodiments, the nucleic acid is a double stranded vector for incorporating exogenous nucleic acid and transfecting into a host cell. In some embodiments, a nucleic acid is a polymer comprising at least 3 nucleotide residues. In some embodiments, a nucleic acid is a polymer comprising at least 5, 6, 7, 8, 9, 10, 11, 12, 13, 14, 15, 16, 17, 18, 19, 20, etc. nucleotide residues. In some embodiments, the nucleic acid comprises known analogs of natural nucleotides that can function in a similar manner as naturally occurring nucleotides. In some embodiments, nucleic acid comprises nucleic acid-like structures with synthetic backbones, as well as amplification products.

Organism: An "organism", as that term is used herein, is a multicellular living entity comprised of a plurality of tissues. In some embodiments, an organism is a human. In some embodiments, an organism is a non-human mammal. In some embodiments, a non-human mammal is selected from the group consisting of consisting of mouse, rat, rabbit, dog, cat, cattle, swine, sheep, horse or primate.

Patient: A "patient", as that term is used herein, is a subject who presents or has presented to a medical provider for diagnosis or treatment of a disease.

Polypeptide (and "Protein"): As is understood by those skilled in the art, a "polypeptide" is a string of at least two amino acids linked to one another by peptide bonds). As is further understood by those skilled in the art, proteins are or comprise polypeptides. Polypeptides may include moieties other than amino acids (e.g., may be glycoproteins) and/or may be otherwise processed or modified. In some embodiments, a protein has an amino acid sequence identical to that of a polypeptide produced in nature (e.g., by cells in an organism); in some such embodiments, the "polypeptide produced in nature" is a complete polypeptide chain as exists in nature and/or is produced by cells in an organism (with or without a signal sequence), or can be a functional portion thereof. In some embodiments, a protein includes more than one polypeptide chain; in some embodiments two or more chains are covalently linked together, for example by one or more disulfide bonds or associated by other means. In some embodiments, a polypeptide has or includes an amino acid sequence identical to that found in a cell or a virus. In some embodiments, a polypeptide has an amino acid sequence not found in nature. In some embodiments, a polypeptide is comprised of natural amino acids. In other embodiments, a polypeptide comprises one or more unnatural amino acids. In some embodiments, a polypeptide is comprised of a combination of natural and unnatural amino acids.

Probe: The term "probe", as used herein, refers to a nucleic acid molecule of known sequence. In some embodiments, a probe has a length within the range of 5 to 100 nucleotides; in some embodiments, a probe has a length bounded by a lower limit selected from the group consisting of 5, 10, 15, 20, and 25 nucleotides, and an upper limit selected from the group consisting of 100 nucleotides. In some embodiments, a probe is prepared by isolation from a natural source, by chemical synthesis, by PCR, etc. In general probes are specific DNA sequences to which nucleic acid fragments from a test sample are hybridized. Probes specifically bind to nucleic acids of complementary or substantially complementary sequence through one or more types of chemical bonds, usually through hydrogen bond formation. Probes may be prepared by any available method.

A reagent that specifically detects expression levels: As used herein, the term "a reagent that specifically detects expression levels" refers to one or more entities that directly or indirectly detect or reveal expression and/or activity levels of one or more biomarkers. Examples of suitable such reagents include, but are not limited to, antibodies that specifically bind to a marker protein of interest (or to a substance generated by or otherwise reflective of level, form, and/or activity of such marker protein), nucleic acid probes that specifically hybridizing to a polynucleotide sequence of interest, or PCR primers capable of specifically amplifying a polynucleotide sequence of interest.

Small Molecule: As is understood in the art, the term "small molecule" typically refers to an organic molecule that is less than about 2 kilodaltons (kDa) in mass. In some embodiments, a small molecule is less than about 1.5 kDa, or less than about 1 kDa. In some embodiments, a small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. In some embodiments a small molecule comprises one or more cyclic carbon or heterocyclic structures and/or aromatic or polyaromatic structures, optionally substituted with one or more of the above functional groups.

System: The terms "system" and "biological system" as used herein may be or comprise any composition, cell, organism, or entity that can express or comprise at least one biomarker for use in accordance with the present invention. In the context of the present invention, in vitro, in vivo, and ex vivo systems are considered; and the system may be a cell, a biological fluid, a biological tissue, or an animal. For example, a system may originate from a living subject (e.g., it may be obtained by drawing blood, or by performing needle biopsy), or from a deceased subject (e.g., it may be obtained at autopsy).

Suffering from: An individual who is "suffering from" a disease, disorder, and/or condition has been diagnosed with and/or displays one or more symptoms of the disease, disorder, and/or condition.

Therapeutic agent: As used herein, the phrase "therapeutic agent" refers to any agent that elicits a desired biological or pharmacological effect.

Therapeutic concentration: As used herein the term "therapeutic concentration" refers a level of agent administered to a subject that is sufficient to elicit a desired biological or pharmacological effect. In some embodiments, a therapeutic concentration is achieved through administration of a single dose; in some embodiments, a therapeutic concentration is achieved through administration of a plurality of doses, optionally spaced apart from one another for example in accordance with a designated regimen.

Tracking Sequence: As used herein the term "tracking sequence" refers to any portion of nucleic acid that is incorporated into the genome of a cell or organism and can be detected using any means known to those in the art.

Treatment: As used herein, the term "treatment" refers to any method used to alleviate, delay onset, reduce severity or incidence, or yield prophylaxis of one or more symptoms or aspects of a disease, disorder, or condition (e.g., calcium disorder). For the purposes of the present invention, treatment can be administered before, during, and/or after the onset of symptoms.

Unit dose: The expression "unit dose" as used herein refers to a physically discrete unit of a pharmaceutical composition, formulated for administration to a subject. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple doses is required, or expected to be required, in order to achieve an intended effect. The unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present disclosure will often be decided by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

DETAILED DESCRIPTION OF CERTAIN EMBODIMENTS

Calcium Disorders

The present invention relates to calcium disorders, and to their treatment with bisphosphonate agents, particularly NBPs. In some embodiments, a calcium disorder may be a condition characterized by anomalous mobilization of calcium and/or phosphate leading to general or specific bone loss. In some embodiment a calcium disorder may result from excessively high calcium and/or phosphate levels in the fluids and/or tissues of the body. Such high levels of calcium in the body may lead to pathological hard tissue demineralization in a subject. Examples of such conditions include, but are not limited to, osteoporosis, osteitis deformans (Paget's disease), hyperparathyroidism, hypercalcemia of malignancy, arthritis and osteolytic bone metastasis.

In some embodiments, a calcium disorder may result from deposition of calcium and/or phosphate anomalously in the body. Such conditions can be referred to as pathologic calcification and be associated with conditions such as, but are not limited to, myositis ossificans progressive, calcinosis univeralis, arthritis, neuritis, bursitis, tendonitis, kidney and renal calculus, bioprostetic and prosthetic heart valves, artherosclerosis, and other inflammatory conditions which predispose involved tissue to deposition of calcium phosphates.

In some embodiments, a calcium disorder may result from an environmental factor. For example, such conditions may include, but are not limited to, increased/decreased calcium and/or phosphate in a subjects diet, exposure to heavy metals, medical treatment (e.g., with a glucocorticoid or antiretroviral agent), exposure to a carcinogen and exposure to chelating agents. In some embodiments, a calcium disorder may result from a non-environmental factor. For example, such conditions may include, but are not limited to, somatic mutation, germline mutation, a subject's age, a subject's sex, a subject's gender and change in hormone level. In one particular embodiment, a calcium disorder may result from an increase and/or decrease in the level of estrogen in a subject. In some embodiments a calcium disorder may result from excessive endogenous production of a glucocorticoid. It will be appreciated that multiple factors may contribute to development or progression of a calcium disorder in a subject.

Bisphosphonate Agents

The present invention relates, among other things, to bisphosphonate agents, and their use in the treatment of a calcium disorder. In some embodiments, bisphosphonate agents may be used for the prevention of bone loss and/or pathological calcification in a subject suffering from a calcium disorder. In some embodiment, bisphosphonate agents may be used in the prophylaxis and treatment of osteoporosis (e.g., post-menopausal osteoporosis and/or corticosteroid-induced osteoporosis). In some embodiments, bisphosphonate agents may be used for the treatment of a subject suffering from metastatic cancer.

In some embodiments, a bisphosphonate agent comprises the general structure ("P—C—P"), where the bisphosphonate belongs to the geminal type, in which the two phosphoryl groups are bound to the same carbon. Optionally, in some embodiments the bisphosphonate agent comprises substituted methylene groups ranging from 2-100 methylene units. In some embodiments, the introduction of modifications and/or elongation of the polyalkylene chain increases the cation binding ability of these compounds and inhibits ectopic calcification better.

In some embodiments the bisphosphonate agent is a non-nitrogenous bisphosphonate. In some embodiments, the bisphosphonate agent is a nitrogenous bisphosphonate (NBP). In some embodiments, the bisphosphonate has a first group ($R_1$) and a second group ($R_2$) attached to the central carbon. In some embodiments, $R_1$ and $R_2$ are independently selected from the group consisting of hydrogen, hydroxy, halogen, amino, SH, phenyl, alkyl, mono- or dialkylamino, mono- or dialkylaminoalkyl, alkoxy, thioalkyl, thiophenyl, and aryl or heteroaryl moieties selected from the group consisting of phenyl, pyridyl, furanyl, pyrrolidinyl, imidazolyl, and benzyl, wherein the aryl or heteroaryl moiety is optionally substituted with alkyl. In some embodiments, a bisphosphonate agent is a diphosphonates, biphosphonic acids, and diphosphonic acids, as well as salts and derivative of these materials.

In some embodiments, a bisphosphonate agent is an NBP selected from the group consisting of pharmaceutical agents described, for example, in U.S. Pat. No. 4,509,612, U.S. Pat. No. 4,666,895, U.S. Pat. No. 4,719,203, EP-A-252,504, EP-A-252,505, U.S. Pat. No. 4,777,163, U.S. Pat. No. 5,002,937, U.S. Pat. No. 4,971,958 and U.S. Pat. No. 4,958,839. In some embodiments, the bisphosphonate agent is at least one or more agents selected from those listed in Table 1.

TABLE 1

| Bisphosphonate (Non-Nitrogenous) | Nitrogenous Bisphosphonate (NBP) |
|---|---|
| Etidronate (Didronel) | Pamidronate (APD, Aredia) |
| Clodronate (Bonefos, Loron) | Alendronte (Fosamax) |
| Tiludronate (Skelid) | Ibandronate (Boniva) |
|  | Risedronate (Actonel) |
|  | Zoledronate (Zometa, Aclasta) |
|  | Incadronate |
|  | Neridronate |
|  | Olpadronate |

Biomarkers Associated with Calcium Disorders

Among other things, the present invention identifies various genes and/or gene products (i.e., "biomarkers") whose level, form, and/or activity is associated with a calcium disorder and/or response to NBP therapy. In particular, for example, the present invention identifies certain genes and/or gene products whose level, form, and/or activity correlates with resistance to one or more negative effects observed with certain NBP therapeutic regimens. In some embodiments, the relevant level, form, and/or activity of such genes and/or gene products does not correlate with and/or is not affected by therapy with bisphosphonate agents other than NBPs. In some embodiments, the relevant level, form and/or activity may be used to indicate how a subject may respond to a treatment regimen. In some embodiments, the relevant level, form and/or activity may be used to indicate the cytotoxic effects of NBP treatment on a subject. In some embodiments, the relevant level, form and/or activity may be used to indicate the bioavailability and/or pharmacological properties of the NBP agent in the subject. In some embodiments, the relevant level, form and/or activity may be used to identify and/or characterize the mechanism of action for a NBP agent. In some embodiments, the relevant level, form and/or activity may be used to characterize, diagnose and/or predict resistance to treatment with an NBP agent.

In some embodiments, a biomarker as provided herein is selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL1), NEL-like protein 2 (NELL2) and combination thereof. In some embodiments, individual biomarkers may be used. In some embodiments, at least two, three, four, five, or six, may be used in combination as a panel.

In some embodiments, a biomarker may be nucleic acid (e.g., gene, mRNA and/or cDNA). In some embodiments, a biomarker may be a nucleic acid sequence from the group consisting of SEQ ID NO's: 1, 2, 3, 4, 5, 6, 7, and 8. In some embodiments, the biomarker may be a nucleic acid sequence comprising at least 15 to 100 bases selected from the group consisting of SEQ ID NO's: 1, 2, 3, 4, 5, 6, 7, and 8. In some embodiments, nucleic acid sequence of SEQ ID NO's: 1, 2, 3, 4, 5, 6, 7, or 8 represents the wild-type and/or reference sequence.

*Homo sapiens* C2orf28; variant 1, mRNA (Genbank Accession No. NM_016085.4)

```
                                                      (SEQ ID NO: 1)
GCACCAAGGGAACGGAAAATGGCGCCTCACGACCCGGGTAGTCTTACGA

CCCTGGTGCCCTGGGCTGCCGCCCTGCTCCTCGCTCTGGGCGTGGAAAG

GGCTCTGGCGCTACCCGAGGTACAGAAGCAAGTTTGAGGTCGGGCTGAA

GCAGGGTCGCTGGCCAGCCGTGCGTCGCGCTCGCCAGCGGCTCCCCCTT

CTCCTCGGCGGGCCTGCGGTTCTGATTTCGTCCCTGACGCTTCCCGACC

CTGCCCAGCCAGATATGCACCCAATGTCCAGGGAGCGTGCAAAATTTGT

CAAAAGTGGCCTTTTATTGTAAAACGACACGAGAGCTAATGCTGCATGC

CCGTTGCTGCCTGAATCAGAAGGGCACCATCTTGGGGCTGGATCTCCAG

AACTGTTCTCTGGAGGACCCTGGTCCAAACTTTCATCAGGCACATACCA

CTGTCATCATAGACCTGCAAGCAAACCCCCTCAAAGGTGACTTGGCCAA

CACCTTCCGTGGCTTTACTCAGCTCCAGACTCTGATACTGCCACAACAT

GTCAACTGTCCTGGAGGAATTAATGCCTGGAATACTATCACCTCTTATA

TAGACAACCAAATCTGTCAAGGGCAAAAGAACCTTTGCAATAACACTGG

GGACCCAGAAATGTGTCCTGAGAATGGATCTTGTGTACCTGATGGTCCA

GGTCTTTTGCAGTGTGTTTGTGCTGATGGTTTCCATGGATACAAGTGTA

TGCGCCAGGGCTCGTTCTCACTGCTTATGTTCTTCGGGATTCTGGGAGC

CACCACTCTATCCGTCTCCATTCTGCTTTGGGCGACCCAGCGCCGAAAA

GCCAAGACTTCATGAACTACATAGGTCTTACCATTGACCTAAGATCAAT

CTGAACTATCTTAGCCCAGTCAGGGAGCTCTGCTTCCTAGAAAGGCATC

TTTCGCCAGTGGATTCGCCTCAAGGTTGAGGCCGCCATTGGAAGATGAA

AAATTGCACTCCCTTGGTGTAGACAAATACCAGTTCCCATTGGTGTTGT

TGCCTATAATAAACACTTTTTTCTTTTTTTTCCTCTCTTTCTTTTTAA

AAAAAAAAAAAAAAAAAA
```

*Homo sapiens* C2orf28; variant 2, mRNA (Genbank Accession No. NM_080592.3)

```
                                                      (SEQ ID NO: 2)
GGAGGGGCCCGAGTTTCTGCGAAGCCGCGACCTCGGCGTCCGGACGCGG

GGAACACCGGGCTGAGGGAGTCTGCAGTCGGCTCCGGGAAGCCGCGCGG

CGACGGGGGAGGCCTTCACTAAAGGGGAAAAGGAAGAGGGGGTCGGCCA
```

```
GTATCCCCGAAAGAGGGCTAGGGCGCATGAAGACCAGCGCAGAGCTCCA

CGAGCAGGAAAAGCCCCCAAGCAGCCCCAGGGCGACTGGACCGGGCCGC

TTAGGCCACGCCCGGGGAAGAGGGCCTGACGCGCTGCGGGGCGGGCCG

CGGGGCCGGGTCGCGCGAGCAGCGGAGCACCAAGGGAACGGAAAATGGC

CGCCTCACGACCCGGGTAGTCTTACGACCCTGGTGCCCTGGGCTGCGCC

CTGCTCCTCGCTCTGGGCGTGGAAAGGGCTCTGGCGCTACCCGAGATAT

GCACCCAATGTCCAGGGAGCGTGCAAAATTTGTCAAAAGTGGCCTTTTA

TTGTAAAACGACACGAGAGCTAATGCTGCATGCCCGTTGCTGCCTGAAT

CCAGAAGGGCACCATCTTGGGGTGGATCTCCAGAACTGTTCTCTGGAGG

ACCCTGGTCCAAACTTTCATCAGGCACATACCACTGTCATCATAGACCT

GCAAGCAAACCCCCTCAAAGGTGACTTGGCCAACACCTTCCGTGGCTTT

TACTCAGCTCCAGACTCTGATACTGCCACAACATGTCAACTGTCCGGAG

GAATTAATGCCTGGAATACTATCACCTCTTATATAGACAACCAAATCTG

TCAAGGGCAAAAGAACCTTTGCAATAACACTGGGGACCCAGAAATGTGT

CCTGAGAATGGATCTTGTGTACCTGATGGTCCAGGTCTTTTGCAGTGTG

TTTGTGCTGATGGTTTCCATGGATACAAGTGTATGCGCCAGGGCTCGTT

CTCACTGCTTATGTTCTTCGGGATTCTGGGAGCCACCACTCTATCCGTC

TCCATTCTGCTTTGGGCGACCCAGCGCCGAAAAGCCAAGACTTCATGAA

CTACATAGGTCTTACCATTGACCTAAGATCAATCTGAACTATCTTAGCC

CAGTCAGGGAGCTCTGCTTCCTAGAAAGGCATCTTTCGCCAGTGGATTC

GCCTCAAGGTTGAGGCCGCCATTGGAAGATGAAAAATTGCACTCCCTTG

GTGTAGACAAATACCAGTTCCCATTGGTGTTGTTGCCTATAATAAACAC

TTTTTTCTTTTTTTTCCTCTCTTTCTTTTTAAAAAAAAAAAA
```

*Homo sapiens* C2orf28; variant 3, mRNA (Genbank Accession No. NM_001170795.1)

```
                                                      (SEQ ID NO: 3)
GCACCAAGGGAACGGAAAATGGCGCCTCACGACCCGGGTAGTCTTACGAC

CCTGGTGCCCTGGGCTGCCGCCCTGCTCCTCGCTCTGGGCGTGGAAAGGG

CTCTGGCGCTACCCGAGATATGCACCCAATGTCCAGGGAGCGTGCAAAATT

TGTCAAAAGTGGCCTTTTATTGTAAAACGACACGAGAGCTAATGCTGCAT

GCCCGTTGCTGCCTGAATCAGAAGGGCACCATCTTGGGGCTGGATCTCCA

GAACTGTTCTCTGGAGGACCCTGGTCCAAACTTTCATCAGGCACATACCA

CTGTCATCATAGACCTGCAAGCAAACCCCCTCAAAGGTGACTTGGCCAAC

ACCTTCCGTGGCTTTACTCAGCTCCAGACTCTGATACTGCCACAACATGT

CAACTGTCCTGGAGGAATTAATGCCTGGAATACTATCACCTCTTATATAG

ACAACCAAATCTGTCAAGGGCAAAAGAACCTTTGCAATAACACTGGGGAC

CCAGAAATGTGTCCTGAGAATGGATCTTGTGTACCTGATGGTCCAGGTCT

TTTGCAGTGTGTTTGTGCTGATGGTTTCCATGGATACAAGTGTATGCGCC

AGGGCTCGTTCTCACTGCTTATGTTCTTCGGGATTCTGGGAGCCACCACT

CTATCCGTCTCCATTCTGCTTTGGGCGACCCAGCGCCGAAAAGCCAAGAC

TTCATGAACTACATAGGTCTTACCATTGACCTAAGATCAATCTGAACTAT
```

-continued

CTTAGCCCAGTCAGGGAGCTCTGCTTCCTAGAAAGGCATCTTTCGCCAGT

GGATTCGCCTCAAGGTTGAGGCCGCCATTGGAAGATGAAAAATTGCACTC

CCTTGGTGTAGACAAATACCAGTTCCCATTGGTGTTGTTGCCTATAATAA

ACACTTTTTCTTTTTTTTTCCTCTCTTTCTTTTTAAAAAAAAAAAAAAAA

AAAAAAA

*Homo sapiens* Phospholipase C-like 1, mRNA (Genbank Accession No. NM_006226.3)

(SEQ ID NO: 4)
ATCGGGCCGCCGGCGTCCGGGCTCCAGAGGCCGCCTGGCTGGGCGCCCGG

TGCCTTTTGTCTGGCGCAGGGCCGGCGTTTGCATCACATTTCGGATACCT

CCCTCTCTTTTTCGCCTCTCCTTCTGCCTCCCGCTCACATCGCCTCCCCA

CTCCCGCCACCGTCCCCGCCGGACTGCTAGCCTCCTAGACCGAAGCCCG

AGGACGTCTCTGCCCGAGCGATGTCCCCTCTCCAGAAAGTTGCCGCCGCC

GCCGCCGCCGCCGCCACTGCCGCCGCTGGGCGGTGAAACAAAGTCTGGCG

GGGCCGCCTCCCGGTGCAGGAGCGCACCGGTGCCTAGCGGCTGGACTCCG

CTGCCGGGCGTCCCGCTTTCCCCCGGGGAGCCCTAAACGCTCCAGGCCAT

GGCCGAGGGCGCGGCCGGCAGGGAGGATCCGGCGCCGCCCGACGCGGCGG

GGGGCGAAGACGACCCCCGAGTGGGCCCGGATGCCGCCGGGGACTGCGTG

ACGGCGGCCTCTGGGGGCCGGATGAGGGACCGTCGCAGCGGGGTCGCACT

GCCAGGCGCCGCGGGACCCCAGCGGACAGCGAGGCGGGCCTCCTGGAGG

CAGCACGGGCGACCCCCCGGCGCAGCAGCATCATCAAGGATCCTTCAAAC

CAAAAATGTGGTGGAAGAAAGAAAACCGTGTCTTTCAGCAGCATGCCATC

GGAAAAGAAAATTAGCAGTGCAAATGACTGCATCAGCTTCATGCAAGCTG

GCTGTGAGTTGAAGAAAGTCCGGCCAAATTCTCGCATTTACAACCGTTTT

TTCACTCTGGACACAGACCTTCAAGCTCTTCGCTGGGAACCTTCAAAGAA

AGACCTCGAGAAAGCCAAGCTTGATATTTCTGCCATAAAAGAGATCAGAC

TGGGGAAAAACACGGAAACATTTAGAAACAATGGCCTTGCTGACCAGATC

TGTGAGGACTGTGCCTTTTCCATACTCCACGGGGAAAACTATGAGTCTCT

GGACCTAGTTGCCAATTCAGCAGATGTGGCAAACATCTGGGTGTCTGGGT

TACGGTACCTGGTTTCTCGAAGTAAGCAGCCTCTTGATTTTATGGAGGGC

AACCAGAACACACCACGGTTCATGTGGTTGAAAACAGTGTTTGAAGCAGC

AGATGTTGATGGGAATGGGATTATGTTGGAAGACACCTCTGTAGAGTTAA

TAAAACAACTCAACCCTACTCTGAAGGAAGCCAAGATCAGGTTAAAGTTT

AAAGAAATCCAGAAGAGCAAGGAAAAACTAACCACCCGCGTGACCGAAGA

GGAATTTTGTGAAGCTTTTTGTGAACTTTGCACCAGGCCAGAAGTGTATT

TCTTACTTGTACAGATATCTAAAAACAAAGAATATTTGGATGCCAATGAT

CTCATGCTCTTTTTAGAAGCTGAGCAAGGAGTCACCCATATCACCGAGGA

TATATGCTTAGACATCATAAGGAGATACGAACTTTCTGAAGAGGGACGTC

AAAAAGGGTTTCTTGCAATTGATGGCTTTACCCAGTATTTATTGTCATCA

GAATGTGACATTTTTGATCCTGAGCAAAAGAAGGTTGCCCAAGATATGAC

CCAGCCATTATCTCACTACTATATCAATGCCTCTCATAACACCTATCTAA

TAGAAGACCAGTTCAGGGGGCCAGCTGACATCAATGGGTACATTAGAGCT

TTGAAAATGGGCTGTCGAAGCGTTGAACTCGATGTAAGTGATGGTTCAGA

TAATGAACCAATCCTTTGTAATCGAAATAACATGACAACCCATGTTTCCT

TTCGAAGTGTCATAGAGGTAATAAATAAATTTGCCTTTGTTGCTTCTGAA

TACCCACTCATTCTTTGCTTGGGAAATCACTGCTCCTTGCCGCAGCAGAA

GGTAATGGCTCAACAGATGAAAAAGGTCTTTGGCAATAAACTCTATACTG

AAGCACCTTTGCCCTCAGAATCCTACCTCCCATCACCAGAAAAATTAAAA

AGAATGATCATTGTGAAAGGAAAGAAGTTGCCTTCTGATCCAGATGTGTT

AGAAGGAGAAGTAACAGATGAAGATGAAGAAGCTGAAATGTCTCGAAGGA

TGTCGGTAGATTACAATGGTGAGCAGAAGCAAATCCGACTCTGTAGGGAG

CTCTCTGATTTGGTGTCTATTTGTAAATCTGTTCAATACAGGGATTTTGA

ACTATCTATGAAAAGCCAAAACTATTGGGAAATGTGTTCATTTAGTGAAA

CAGAGGCCAGCCGCATTGCAAATGAGTACCCAGAGGATTTTGTTAATTAT

AATAAGAAGTTCTTATCAAGAATCTATCCAAGTGCCATGAGGATCGATTC

CAGTAACTTGAATCCACAGGACTTTTGGAATTGTGGCTGTCAGATTGTAG

CAATGAATTTTCAGACTCCGGGTCCAATGATGGACCTTCACACGGGCTGG

TTTCTTCAAAACGGGGGATGTGGTTATGTTCTAAGGCCGTCTATAATGCG

AGATGAAGTTTCTTACTTCAGCGCAAATACAAAGGGCATTCTACCTGGGG

TGTCTCCTCTAGCTCTTCATATCAAGATCATCAGTGGTCAGAATTTCCCA

AAGCCCAAGGGAGCTTGTGCCAAAGGGGATGTCATAGATCCCTATGTTTG

TATAGAGATACACGGAATTCCAGCGGATTGTTCGGAACAAAGAACTAAAA

CTGTACAGCAAAACAGTGATAATCCTATTTTTGATGAAACTTTTGAGTTC

CAAGTAAACCTACCTGAGCTGGCCATGATCCGTTTTGTTGTTCTGGATGA

TGACTACATTGGGGATGAGTTTATAGGGCAATATACGATACCATTTGAAT

GTTTGCAGCCTGGATATCGGCATGTTCCCCTGCGTTCTTTTGTGGGTGAC

ATCATGGAGCACGTAACCCTTTTTGTCCACATAGCAATAACTAATCGAAG

TGGAGGAGGAAAGGCACAGAAGCGCAGTCTTTCAGTGAGAATGGGGAAGA

AAGTTCGGAATATACCATGCTCAGGAATATCGGTCTTAAAACCATTGAT

GACATCTTTAAAATAGCGGTTCATCCATTACGAGAAGCCATAGATATGAG

AGAAAATATGCAGAATGCAATCGTGTCTATTAAGGAACTATGTGGACTCC

CTCCAATTGCCAGTCTGAAGCAGTGCCTGTTAACTCTGTCATCTCGGCTC

ATCACCAGTGACAATACTCCTTCAGTCTCACTTGTGATGAAAGACAGCTT

TCCTTACCTGGAGCCTCTGGGTGCAATTCCAGATGTGCAGAAAAAGATGC

TGACTGCTTATGATCTGATGATTCAAGAGAGCCGGTTTCTCATAGAAATG

GCGGACACAGTCCAGGAAAGATTGTACAGTGTCAGAAAGCAGGGATGGA

GTTCCATGAAGAACTTCATAATTTGGGGGCAAAAGAAGGCTTGAAGGGAA

GAAAACTCAACAAAGCAACTGAGAGCTTTGCTTGGAACATTACAGTATTG

AAGGGCCAAGGAGATCTGTTGAAGAATGCCAAGAATGAAGCTATAGAAAA

CATGAAGCAGATCCAGCTGGCATGCCTGTCCTGTGGACTGAGTAAAGCCC

CCAGCAGCAGTGCTGAGGCCAAGAGCAAGCGCAGCCTGGAAGCCATAGAG

-continued

```
GAGAAGGAAAGTAGTGAGGAGAATGGGAAGCTGTGACTCTGGGCATTATC
GACACGTTCACCCATCTTATCAAGGACTCTGGTTTCTCATTCTTGTTTTC
TTTCTTTAAATGTTTTATAAGTTCACAAAATGGTGCCCTATATGGGTAT
TGGACATAGATATTTTCACAATGTCAGTATTTCAGTGTAGTTAATTTATC
TAAATTAAAGCCTTTAGTATCAGTGTTTTAAATTCTGAGACATGTGTCAA
CACCCCTGTGTGGATGCCTGTGGAAGAGTGTGTGTGTGTGTGTGTGTG
TGTGTGTGGCAGAGAGAGAGAAAGAGAGAGAGAGAGAGAAATTCTGTTAA
AATCTATTCTGTGTTGCATTATTCATTTAGTGAGTTATTCCTTGATCATT
TTGGGACAATTGTTTTAATCTGAAATTCTAAAGAGCACTTACTGTAACCT
GTTGCTGTGTTTAATTTGACTTCTCTGCCTTTGACATTTAATTTAGTGAT
CTTAGCATAGCTTATTATTGAAGGAAGCCAAATTTATCAAAGCATAGATG
TTTTGGTAGATTAAATATAGATTAGAAAAATTCCTAAGAATCAGAGTAGA
AATAAAAGTGAATGAAAGATTAAACAGATGATGAGAATTTCTAAAAAGAT
TAGCAAGGTCATTTCTTCAGTCAGAAAACTTTAAAAAATATTTATTAAAT
AAAATCAATTTTTAGGAAGTTTTCTGTAGTCATTTACTAAACATATGATT
TCACTAGAAAAGCTGATCATAAGTGAATTTATACCTACCTGTGTGGTACT
CTGAAACACACTGAAAGCTCTGTTGCAATTAGGATTTTGATGTGACAATA
ATATTGTTGTATAATTTCGAGATTTGTAGGAAGGTCTCATTCTTCCAAGC
TGAGAGTCTAGCACTCATTTTCTATAACAGATATGGCAGCTTAGAGGTGT
TGGCTTTGTTTGGATGTAATTTAGGGTACTAAATTTAAATTTAAAGATAT
TGTTCAAACAATATCATATCATCACATTGAGCTGATATAAATTCTGTGGG
TCCGATAATATCTTTGTGATAATTTAAGAGCTAACCAGTTACCACACATC
TATGATATAACCCTAACACACACAGAAAAGCATACATGCAAAAGAAATG
ACTAATTAGGGTACATTTATAATTGCATCTAGGTAATTTTTACCCTAATG
TCTTCATAAAGTACTTGAGTGTAATGTTTGTTACCTCCAACAGAACTAAA
TGTTCTATGGTTATGAAAGAATATATTTATTTAAAGCATTGCTTTTATTT
TGAAAAGCTTCTTAATTAATTTGATTAACAAATATGCTAATTTGGGGAAA
CCTAGAGAAGATAATTGTTGAAATTTTGCAAATATAAACATCTCCTATAG
CTTCTGTGTTATTTCTGACTTCTTAACACTATTATGTTTATGTTGCACAT
TACTGAAAGAGTAAAGATATGAAAAAAACACTTATTGTTTTCTTTTATTG
TGAATTGAAAAGCAAAGCTAATGAAAATGGGTTACTACATCAAAAATAT
CTTAAAGAGTTTGCTATTTCCATGGACCAGATATGATGAAATTATTCCCT
GGGTTTAAAACTGGGCACTCGAGGAGGAGGTACCTGAAGTCATTTGAAGG
CAAGTTTCCAATGATGCTACAATGGCCTGAAAAAATTTCTTTACCCTCTG
TTATATTTAACTTGCTGGTAGGAGGAATAGTGGAATGCAGGTGTTAAGCC
CTTTGTGGTGAAAAAGAGGTTCTATAGACAGAAACAAAACCCACCTTACA
TCAGCTGATTGGTTGATTTACTAGTGTACCTCTTCATCTACTTGAATTC
TATTTGGTAAATCCATGTCTTTACTGGATATACAGTTAGGTGGGAAGAGG
AGATAAAGGATGACAAACTCTCAAACAATATTTATACATTTATTTACTCC
AGGGTCAAATCCAATCCTTGGAAGTAGCTTCTCTAGTTTATTTTATTTGT
CCCAGAGCTCTACTCACACTTAGGACCCACCCAAAAATTCTCAAAAACGT
AATATGGATTCTGCCTCATCTGATGCTATTTCTGGCAGTGGGTTGTCAGC
CATACTCTGCTTCATTCCACTGGGTGTCCTTGCTAGATGGGAGTGAGAT
GTGGAGCAGGGAGGAGCTTTGGATTCTGGGAGTGGAGGTGGCAAGGGAAA
AGTCTCCTAGTCTCCTGTGATGTTCCTGCCTCCAGATAGAATAGCAAAAA
CAAACAATTTTTTTTGTGTATTATGCCTCCATGACATTGTTACATTCTA
TGAGGAGCATCTGTCTCCTTTCTAGACTTGAACTGTGGTAGAAAAAGCCC
CCTTCTCTCTTCTATCTACTTAGATTTGGTGATGCTAGGAATGTAGTGTT
TTAGATATTAATTCTATTTTTATTTATTCATTTTTACATCACCAATAGGA
TCTGAGGTGGAGATGGCGGGTATTATCACTGGCATTTTACAGGTGAGAAA
GCCCAAAGCCACTGAGGTAATTAATGGAATAATTGATTTTGAACTTGGGT
CTGTCTGATTTCATGTGCAAGATTATATACTTAGTGATTTTGATTTTAAG
TTTATTCTTAACATTTTAAACCAGACTATTAACTCTTACCTTTATAACCA
CAGATACAAAGAACTGTATCATTTATTTTCTGAATATAAAATATTAATGG
TCAATATAAAAATACAAAAATAGAGAACTATATACAACAGAAAAGCAAAA
TTACCCACTAATAACATTTTGATTTATATCCCTTTAGACACTGTTTAGAG
TTTATACATATATGTAAATATGCTTGTATTTTAACAAAATTGAGATATTA
TATAAACTGTTTGTAGCAGGGTGTTTAAAATTTTAACAATATGTTATGGA
TATCTTTCTGTGTCAATAAATGTGTATTTACATTAGAGTTCCAAGCATTT
GAACTGAA
```

*Homo sapiens* Ephrin Receptor B1, mRNA (Genbank Accession No. NM_004441.4)

(SEQ ID NO: 5)
```
GTCAGTCTGGCCGGCTCCGTCCTCCCGTAGGCTCCGCTGTAGCTAGCAAT
GTGACACCAGGACGCACTCGCTCTCGCGCGCTCTCCCAGGCTCGTTCTCC
CTCGCCCTCTCTCTCTCACACACGCACGCACACACCCACCTCTCCCATAA
ACACACACACACACATGCACACCCACACCCACGCGCGCCCGCACCGCCCC
ACGCGCACACACTCCTGCCCACGCCCACGCAGCGCTCCGGGAAGTCCGGT
CCGGGCGAGAGCGCGAAAGGATACCGAGAAGCCACCCGCGGAGAGCGCAG
CGGCGCCCTGGGACGCGGCGCTCTCCCGGCGCTGCTGCCTCGGCTTGGTC
TCGGCCTGCGGGCCGTCGGCCGGCGATGGCCCTGGATTATCTACTACTGC
TCCTCCTGGCATCCGCAGTGGCTGCGATGGAAGAAACGTTAATGGACACC
AGAACGGCTACTGCAGAGCTGGGCTGGACGGCCAATCCTGCGTCCGGGTG
GGAAGAAGTCAGTGGCTACGATGAAAACCTGAACACCATCCGCACCTACC
AGGTGTGCAATGTCTTCGAGCCCAACCAGAACAATTGGCTGCTCACCACC
TTCATCAACCGGCGGGGGCCCATCGCATCTACACAGAGATGCGCTTCAC
TGTGAGAGACTGCAGCAGCCTCCCTAATGTCCCAGGATCCTGCAAGGAGA
CCTTCAACTTGTATTACTATGAGACTGACTCTGTCATTGCCACCAAGAAG
TCAGCCTTCTGGTCTGAGGCCCCCTACCTCAAAGTAGACACCATTGCTGC
AGATGAGAGCTTCTCCCAGGTGGACTTTGGGGGAAGGCTGATGAAGGTAA
ACACAGAAGTCAGGAGCTTTGGGCCTCTTACTCGGAATGGTTTTTACCTC
```

-continued

```
GCTTTTCAGGATTATGGAGCCTGTATGTCTCTTCTTTCTGTCCGTGTCTT
CTTCAAAAAGTGTCCCAGCATTGTGCAAAATTTTGCAGTGTTTCCAGAGA
CTATGACAGGGGCAGAGAGCACATCTCTGGTGATTGCTCGGGGCACATGC
ATCCCCAACGCAGAGGAAGTGGACGTGCCCATCAAACTCTACTGCAACGG
GGATGGGGAATGGATGGTGCCTATTGGGCGATGCACCTGCAAGCCTGGCT
ATGAGCCTGAGAACAGCGTGGCATGCAAGGCTTGCCCTGCAGGGACATTC
AAGGCCAGCCAGGAAGCTGAAGGCTGCTCCCACTGCCCCTCCAACAGCCG
CTCCCCTGCAGAGGCGTCTCCCATCTGCACCTGTCGGACCGGTTATTACC
GAGCGGACTTTGACCCTCCAGAAGTGGCATGCACTAGCGTCCCATCAGGT
CCCCGCAATGTTATCTCCATCGTCAATGAGACGTCCATCATTCTGGAGTG
GCACCCTCCAAGGGAGACAGGTGGGCGGGATGATGTGACCTACAACATCA
TCTGCAAAAAGTGCCGGGCAGACCGCCGGAGCTGCTCCCGCTGTGACGAC
AATGTGGAGTTTGTGCCCAGGCAGCTGGGCCTGACGGAGTGCCGCGTCTC
CATCAGCAGCCTGTGGGCCCACACCCCCTACACCTTTGACATCCAGGCCA
TCAATGGAGTCTCCAGCAAGAGTCCCTTCCCCCCACAGCACGTCTCTGTC
AACATCACCACAAACCAAGCCGCCCCCTCCACCGTTCCCATCATGCACCA
AGTCAGTGCCACTATGAGGAGCATCACCTTGTCATGGCCACAGCCGGAGC
AGCCCAATGGCATCATCCTGGACTATGAGATCCGGTACTATGAGAAGGAA
CACAATGAGTTCAACTCCTCCATGGCCAGGAGTCAGACCAACACAGCAAG
GATTGATGGCTGCGGCCTGGCATGGTATATGTGGTACAGGTGCGTGCCC
GCACTGTTGCTGGCTACGGCAAGTTCAGTGGCAAGATGTGCTTCCAGACT
GCTGACTGACGATGATTACAAGTCAGAGCTAGGGAGCAGCTGCCCCTGAT
TGCTGGCTCGGCAGCGGCCGGGGTCGTGTTCGTTGTGTCCTTGGTGGCCA
TCTCTATCGTCTGTAGCAGGAAACGGGCTTATAGCAAAGAGGCTGTGTAC
AGCGATAAGCTCCAGCATTACAGCACAGGCCGAGGCTCCCCAGGGATGAA
GATCTACATTGACCCCTTCACTTACGAGGATCCCAACGAAGCTGTCCGGG
AGTTTGCCAAGGAGATTGATGTATCTTTTGTGAAAATTGAAGAGGTCATC
GGAGCAGGGGAGTTTGGAGAAGTGTACAAGGGGCGTTTGAAACTGCCAGG
CAAGAGGGAAATCTACGTGGCCATCAAGACCCTGAAGGCAGGGTACTCGG
AGAAGCAGCGTCGGGACTTTCTGAGTGAGGCGAGCATCATGGGCCAGTTC
GACCATCCTAACATCATTCGCCTGGAGGGTGTGGTCACCAAGAGTCGGCC
TGTCATGATCATCACAGAGTTCATGGAGAATGGTGCATTGGATTCTTTCC
TCAGGCAAAATGACGGGCAGTTCACCGTGATCCAGCTTGTGGGTATGCTC
AGGGGCATCGCTGCTGGCATGAAGTACCTGGCTGAGATGAATTATGTGCA
TCGGGACCTGGCTGCTAGGAACATTCTGGTCAACAGTAACCTGGTGTGCA
AGGTGTCCGACTTTGGCCTCTCCCGCTACCTCCAGGATGACACCTCAGAT
CCCACCTACACCAGCTCCTTGGGAGGGAAGATCCCTGTGAGATGGACAGC
TCCAGAGGCCATCGCCTACCGCAAGTTCACTTCAGCCAGCGACGTTTGGA
GCTATGGGATCGTCATGTGGGAAGTCATGTCATTTGGAGAGAGACCCTAT
TGGGATATGTCCAACCAAGATGTCATCAATGCCATCGAGCAGGACTACCG
GCTGCCCCCACCCATGGACTGTCCAGCTGCTCTACACCAGCTCATGCTGG
ACTGTTGGCAGAAGGACCGGAACAGCCGGCCCCGGTTTGCGGAGATTGTC
AACACCCTAGATAAGATGATCCGGAACCCGGCAAGTCTCAAGACTGTGGC
AACCATCACCGCCGTGCCTTCCCAGCCCCTGCTCGACCGCTCCATCCCAG
ACTTCACGGCCTTTACCACCGTGGATGACTGGCTCAGCGCCATCAAAATG
GTCCAGTACAGGGACAGCTTCCTCACTGCTGGCTTCACCTCCCTCCAGCT
GGTCACCCAGATGACATCAGAAGACCTCCTGAGAATAGGCATCACCTTGG
CAGGCCATCAGAAGAAGATCCTGAACAGCATTCATTCTATGAGGGTCCAG
ATAAGTCAGTCACCAACGGCAATGGCATGAGAACTCTTGTTTCTTGGGGA
AGGAGAGGAGGGAAAAGGACCAGGGTCAAGGGGGACCAGAGGTTGACCAC
TGTGGAATGTACTGGAGAGACTGGCTTCTCAGCTGAGGAATGCATTTCCA
TCAGTGAAGAATCAACCGGACCTGTTGCTAGCAGGCAATCTCCATTTCTC
AGTGACAGAAGCATGTTTGAGATGCCGTGGGAAACCAAATATATAATAAT
AAAAATATAAAAAGGTGATGTTCAACAGAAGTGAAGACAAAACAATATGC
ATCAGGAGAACAAGAGTAAACCCAGCTCCCACTCTCAGTGGGCTGCAGTT
GCCCAACCACAGGAAGAAAGGGAAGGAGGTAGAGGGAAGAAACAGAAGCA
GTGTTCCATTTTCTTCCTCACCAATGACATTCTTTTCTTTTCTCCTTTCG
TACTCCTCCCTGAGAGTCCCCTCCCTTCTCCCACACTCGTTTCCCTTTGC
TCATGACTCCTGTAGGGAAGTTTCTTCAAACAAAACCCAGCTCCTGAGTC
TCCAGATGTTGTTCTGTCAGTTGCCAAAGGACTTTGCTGACCACTGCATG
GGGATCCAACCAATTCAATTAATGTCTTCATATTGAAGAAGAGATGTACC
TTCAATTGAAAACCTCGTTTTTCTTTTGTTTGCATTTTCTGCAAAAAGGA
AAAAGAAACCACAAATTGGGGAAAAAAAAGAAGAAAAACCTGTTTCCGT
GTGCAAAAGCACACATATGTATGTCTGTGTTATAAAATGACTGTGCTTGT
TCGTAACAGATGCAAACAAGAAAGAAGAACTGGGAAGTCTTTGTCCCTAG
GAAATCCAAAGGGGCTGGAATATGGTGTTGGTTTGGCTTTCTGGTTGGCC
CAATCGGCCTATTGGCTCAATGGGAAGAGAGGAGAGGGAGAAAAATAAAA
TGAAAGGAAAAAAAAAGTTTGCAAATTCAGACAGGAAACAGGTGAGTGG
TTTGAATTGGATGCAGTGTGGGCCATCCTGGAATGATACTGACTGATTAA
TTATTCCTGATAACATCTCAAGAAAAGGAGAAGGAAAGTGTTTCTGGAGA
ATGTTCTTTCACATCACTGGAATCTGCAATTCAAGAAGTGACAAGGGAGA
ATTCTTGCTTTACCTATGGACTGGCTTAAGCCGTGTGGCATCCGAGGAAT
GTTTCAAATGTGTCTGTGTTTCTCTTTACATTCCTTGTTGTACCTCATTG
TTCAATTCACTTTTGTAAATTCCACCTAACATTTAATTATTTTAAATTTC
TCCTTTTACCTTAATCTCCTTGCTAATTTTATCTGTCTAATTAAAAAGAG
CAGAAGCATGTCTGGGTTTACGTAAAAAAAAAAAAAAAAAA
```

*Homo sapiens* Syntrophin, Gamma 1, mRNA (Genbank Accession No. NM_018967.2)

(SEQ ID NO: 6)
```
TTAGAAGCTCTGAGAAATCATGGGCCGTGCGGTAGGGGTTGAAATGCTCA
AAGGTCCACACTTCTTGAAATAAACAGAATGGTCTTGAGTGGATTGCAAC
```

```
TGTTTTGGAAATAGCTTTGTGAAAAGAGGGTGGAGAGCTACTCAAAATTC
TACGTTAGAGAGACTGAAAAGACATCTAATTTCATTGCTCGGCAGACTGC
TCTCCAGAATGTTGAGATTGCCCGAGAAGTGACCCCAGCAAAAGAAAAT
ATTGCTGTACCTAAATTCAAACGACATCCTTTGTGGTGCCACAGCACATG
GATTTCAGAACCGCCTGTGAGGAGACAAAGACAGGAATTTGTTTGCTGCA
GGATGGTAACCAGGAGCCTTTCAAAGTGCGGCTGCACCTAGCCAAAGACA
TTTTGATGATCCAGGAACAGGATGTGATATGTGTGTCTGGTGAGCCTTTC
TATTCTGGTGAAAGAACGGTGACCATCAGAAGACAAACAGTAGGAGGATT
TGGATTAAGCATAAAGGGAGGAGCAGAACATAACATTCCAGTTGTCGTTT
CAAAAATCTCCAAGGAACAAAGAGCGGAACTTTCAGGACTACTTTTTATT
GGAGATGCAATTCTACAGATAAATGGCATTAATGTGAGAAAATGTAGACA
TGAAGAAGTGGTTCAGGTTCTTCGGAATGCTGGAGAAGAGTGACTCTAAC
AGTGTCATTTTTAAAAAGAGCACCTGCTTTCCTCAAACTCCCATTGAATG
AAGATTGTGCATGTGCTCCAAGTGACCAGAGCAGTGGCACCTCCTCTCCT
CTCTGTGACAGTGGCTTACATCTCAACTACCATCCCAACAATACAGACAC
ATTATCATGCTCGTCGTGGCCGACGTCTCCAGGCTTGAGGTGGGAGAAGC
GATGGTGCGACCTCAGACTGATCCCTCTACTTCATTCGCGCTTCTCTCAG
TATGTGCCCGGCACAGATTTGAGTCGGCAGAATGCCTTTCAAGTCATTGC
TGTGGATGGGGTCTGCACTGGGATTATTCAGTGCCTCTCTGCTGAAGACT
GCGTTGACTGGCTACAAGCAATAGCAACTAACATTTCAAATCTCACAAAG
CACAATATTAAAAAAATCAACAGAAACTTTCCTGTAAACCAGCAGATTGT
CTACATGGGCTGGTGTGAAGCCCGGGAGCAAGACCCCCTCCAGGACAGAG
TGTACTCCCCGACCTTCCTGGCCCTGAGGGGCTCATGTCTCTACAAGTTT
CTGGCACCTCCAGTGACCACCTGGGACTGGACGAGAGCAGAGAAAACATT
CTCAGTTTATGAGATTATGTGCAAGATCCTCAAGGACAGTGACCTGCTGG
ACCGACGGAAACAGTGCTTCACCGTGCAGTCTGAGTCTGGGGAGGACCTG
TACTTCTCAGTGGAGCTGGAAAGTGACCTCGCCCAGTGGGAAAGAGCCTT
CCAGACAGCAACCTTTCTAGAAGTAGAACGGATACAGTGCAAGACCTATG
CATGTGTGCTAGAAAGTCATCTAATGGGACTCACAATTGATTTCAGCACA
GGATTTATCTGCTTTGATGCTGCAACAAAGGCTGTCCTTTGGAGGTATAA
ATTCTCTCAGCTTAAAGGTTCTTCAGATGATGGCAAGAGCAAAATCAAAT
TTTTGTTTCAGAATCCAGATACTAAACAGATTGAAGCAAAGGAGTTGGAA
TTTTCTAATTTATTTGCTGTTCTTCACTGCATTCATTCCTTCTTTGCTGC
CAAGGTAGCTTGTTTGGACCCTCTATTTTAGGCAATCAAGCTACTGCTT
CTACTGCTGCCAGCTCTGCTACCACGAGCAAAGCAAAGTATACAACTTGA
CATACTGAACTCTTCATTGACACACCCCATGACTGTAT
```

Homo sapiens NELL1, mRNA (Genbank Accession No. BC096102)

(SEQ ID NO: 7)
```
TCCAGGCTCATTTGCTTCCACCTAGCTTCGGTGCCCCCTGCTAGGCGGGG
ACCCTCGAGAGCGATGCCGATGGATTTGATTTTAGTTGTGTGGTTCTGTG
TGTGCACTGCCAGGACAGTGGTGGGCTTTGGGATGGACCCTGACCTTCAG
ATGGATATCGTCACCGAGCTTGACCTTGTGAACACCACCCTTGGAGTTGC
TCAGGTGTCTGGAATGCACAATGCCAGCAAAGCATTTTTATTTCAAGACA
TAGAAAGAGAGATCCATGCAGCTCCTCATGTGAGTGAGAAATTAATTCAG
CTGTTCCGGAACAAGAGTGAATTCACCATTTTGGCCACTGTACAGCAGAA
GCCATCTACTTCAGGAGTGATACTGTCCATTCGAGAACTGGAGCACAGCT
ATTTTGAACTGGAGAGCAGTGGCCTGAGGGATGAGATTCGGTATCACTAC
ATACACAATGGGAAGCCAAGGACAGAGGCACTTCCTTACCGCATGGCAGA
TGGACAATGGCACAAGGTTGCACTGTCAGTTAGCGCCTCTCATCTCCTGC
TCCATGTCGACTGTAACAGGATTTATGAGCGTGTGATAGACCCTCCAGAT
ACCAACCTTCCCCCAGGAATCAATTTATGGCTTGGCCAGCGCAACCAAAA
GCATGGCTTATTCAAAGGGATCATCCAAGATGGGAAGATCATCTTTATGC
CGAATGGATATATAACACAGTGTCCAAATCTAAATCACACTTGCCCAACC
TGCAGTGATTTCTTAAGCCTGGTGCAAGGAATAATGGATTTACAAGAGCT
TTTGGCCAAGATGACTGCAAAACTAAATTATGCAGAGACAAGACTTAGTC
AATTGGAAAACTGTCATTGTGAGAAGACTTGTCAAGTGAGTGGACTGCTC
TATCGAGATCAAGACTCTTGGGTAGATGGTGACCATTGCAGGAACTGCAC
TTGCAAAAGTGGTGCCGTGGAATGCCGAAGGATGTCCTGTCCCCCTCTCA
ATTGCTCCCCAGACTCCCTCCCAGTGCACATTGCTGGCCAGTGCTGTAAG
GTCTGCCGACCAAAATGTATCTATGGAGGAAAAGTTCTTGCAGAAGGCCA
GCGGATTTTAACCAAGAGCTGTCGGGAATGCCGAGGTGGAGTTTTAGTAA
AAATTACAGAAATGTGTCCTCCTTTGAACTGCTCAGAAAAGGATCACATT
CTTCCTGAGAATCAGTGCTGCCGTGTCTGTAGAGGTCATAACTTTTGTGC
AGAAGGACCTAAATGTGGTGAAAACTCAGAGTGCAAAAACTGGAATACAA
AAGCTACTTGTGAGTGCAAGAGTGGTTACATCTCTGTCCAGGGAGACTCT
GCCTACTGTGAAGATATTGATGAGTGTGCAGCTAAGATGCATTACTGTCA
TGCCAATACTGTGTGTGTCAACCTTCCTGGGTTATATCGCTGTGACTGTG
TCCCAGGATACATTCGTGTGGATGACTTCTCTTGTACAGAACACGATGAA
TGTGGCAGCGGCCAGCACAACTGTGATGAGAATGCCATCTGCACCAACAC
TGTCCAGGGACACAGCTGCACCTGCAAACCGGGCTACGTGGGGAACGGGA
CCATCTGCAGAGCTTTCTGTGAAGAGGGCTGCAGATACGGTGGAACGTGT
GTGGCTCCCAACAAATGTGTCTGTCCATCTGGATTCACAGGAAGCCACTG
CGAGAAAGATATTGATGAATGTTCAGAGGGAATCATTGAGTGCCACAACC
ATTCCCGCTGCGTTAACCTGCCAGGGTGGTACCACTGTGAGTGCAGAAGC
GGTTTCCATGACGATGGGACCTATTCACTGTCCGGGGAGTCCTGTATTGA
CATTGATGAATGTGCCTTAAGAACTCACACCTGTTGGAACGATTCTGCCT
GCATCAACCTGGCAGGGGGTTTTGACTGTCTCTGCCCCTCTGGGCCCTCC
TGCTCTGGTGACTGTCCTCATGAAGGGGGCTGAAGCACAATGGCCAGGT
GTGGACCTTGAAAGAAGACAGGTGTTCTGTCTGCTCCTGCAAGGATGGCA
AGATATTCTGCCGACGGACAGCTTGTGATTGCCAGAATCCAAGTGCTGAC
```

-continued

CTATTCTGTTGCCCAGAATGTGACACCAGAGTCACAAGTCAATGTTTAGA

CCAAAATGGTCACAAGCTGTATCGAAGTGGAGACAATTGGACCCATAGCT

GTCAGCAGTGTCGGTGTCTGGAAGGAGAGGTAGATTGCTGGCCACTCACT

TGCCCCAACTTGAGCTGTGAGTATACAGCTATCTTAGAAGGGGAATGTTG

TCCCCGCTGTGTCAGTGACCCCTGCCTAGCTGATAACATCACCTATGACA

TCAGAAAAACTTGCCTGGACAGCTATGGTGTTTCACGGCTTAGTGGCTCA

GTGTGGACGATGGCTGGATCTCCCTGCACAACCTGTAAATGCAAGAATGG

AAGAGTCTGTTGTTCTGTGGATTTTGAGTGTCTTCAAAATAATTGAAGTA

TTTACAGTGGACTCAACGCAGAAGAATGGACGAAATGACCA

*Homo sapiens* NELL2, mRNA (Genbank Accession No. BC020544.1)

(SEQ ID NO: 8)
CCCCGACGGAGCCGCGCCGGGGCGAGTCCGACCCCTCCCTCCGGGCCCCC

TCCGGGCCGCGCTGCCGCCTCGGCCCTGCGTGTGGGAATGATGTGCGCAT

TGGAGGGTCTAAGTTCTTCACGCGCCTGGGGAGGCCTCCCTTTTCTTTCT

TAGGCAACCAAAGCGTATTAATCCTACTGATCAGTAAATCCGAGGCAGCA

GCAGGAGAGACAAACGTTATTTTCCCGCTTGATTCCAAGAACCTCTTCGA

TTTTTATTTTTATTTTTAAAGAGGGAGACGATGGACTGAGCTGATCCGCA

CCATGGAGTCTCGGGTCTTACTGAGAACATTCTGTTTGATCTTCGGTCTC

GGAGCAGTTTGGGGGCTTGGTGTGGACCCTTCCCTACAGATTGACGTCTT

AACAGAGTTAGAACTTGGGGAGTCCACGACCGGAGTGCGTCAGGTCCGG

GGCTGCATAATGGGACGAAAGCCTTTCTCTTTCAAGATACTCCCAGAAGC

ATAAAAGCATCCACTGCTACAGCTGAACAGTTTTTTCAGAAGCTGAGAAA

TAAACATGAATTTACTATTTTGGTGACCCTAAAACAGACCCACTTAAATT

CAGGAGTTATTCTCTCAATTCACCACTTGGATCACAGGTACCTGGAACTG

GAAAGTAGTGGCCATCGGAATGAAGTCAGACTGCATTACCGCTCAGGCAG

TCACCGCCCTCACACAGAAGTGTTTCCTTACATTTTGGCTGATGACAAGT

GGCACAAGCTCTCCTTAGCCATCAGTGCTTCCCATTTGATTTTACACATT

GACTGCAATAAAATTTATGAAAGGGTAGTAGAAAAGCCCTCCACAGACTT

GCCTCTAGGCACAACATTTTGGCTAGGACAGAGAAATAATGCGCATGGAT

ATTTTAAGGGTATAATGCAAGATGTCCAATTACTTGTCATGCCCCAGGGA

TTTATTGCTCAGTGCCCAGATCTTAATCGCACCTGTCCAACTTGCAATGA

CTTCCATGGACTTGTGCAGAAAATCATGGAGCTACAGGATATTTTAGCCA

AAACATCAGCCAAGCTGTCTCGAGCTGAACAGCGAATGAATAGATTGGAT

CAGTGCTATTGTGAAAGGACTTGCACCATGAAGGGAACCACCTACCGAGA

ATTTGAGTCCTGGATAGACGGCTGTAAGAACTGCACATGCCTGAATGGAA

CCATCCAGTGTGAAACTCTAATCTGCCCAAATCCTGACTGCCCACTTAAG

TCGGCTCTTGCGTATGTGGATGGCAAATGCTGTAAGGAATGCAAATCGAT

ATGCCAATTTCAAGGACGAACCTACTTTGAAGGAGAAAGAAATACAGTCT

ATTCCTCTTCTGGAGTATGTGTTCTCTATGAGTGCAAGGACCAGACCATG

AAACTTGTTGAGAGTTCAGGCTGTCCAGCTTTGGATTGTCCAGAGTCTCA

TCAGATAACCTTGTCTCACAGCTGTTGCAAAGTTTGTAAAGGTTATGACT

TTTGTTCTGAAAGGCATAACTGCATGGAGAATTCCATCTGCAGAAATCTG

AATGACAGGGCTGTTTGTAGCTGTCGAGATGGTTTTAGGGCTCTTCGAGA

GGATAATGCCTACTGTGAAGACATCGATGAGTGTGCTGAAGGGCGCCATT

ACTGTCGTGAAAATACAATGTGTGTCAACACCCCGGGTTCTTTTATGTGC

ATCTGCAAAACTGGATACATCAGAATTGATGATTATTCATGTACAGAACA

TGATGAGTGTATCACAAATCAGCACAACTGTGATGAAAATGCTTTATGCT

TCAACACTGTTGGAGGACACAACTGTGTTTGCAAGCCGGGCTATACAGGG

AATGGAACGACATGCAAAGCATTTTGCAAAGATGGCTGTAGGAATGGAGG

AGCCTGTATTGCCGCTAATGTGTGTGCCTGCCCACAAGGCTTCACTGGAC

CCAGCTGTGAAACGGACATTGATGAATGCTCTGATGGTTTTGTTCAATGT

GACAGTCGTGCTAATTGCATTAACCTGCCTGGATGGTACCACTGTGAGTG

CAGAGATGGCTACCATGACAATGGGATGTTTTCACCAAGTGGAGAATCGT

GTGAAGATATTGATGAGTGTGGACCGGGAGGCACAGCTGTGCCAATGAT

ACCATTTGCTTCAATTTGGATGGCGGATATGATTGTCGATGTCCTCATGG

AAAGAATTGCACAGGGGACTGCATCCATGATGGAAAAGTTAAGCACAATG

GTCAGATTTGGGTGTTGGAAAATGACAGGTGCTCTGTGTGCTCATGTCAG

AATGGATTCGTTATGTGTCGACGGATGGTCTGTGACTGTGAGAATCCCAC

AGTTGATCTTTTTTGCTGCCCTGAATGTGACCCAAGGCTTAGTAGTCAGT

GCCTCCATCAAAATGGGGAAACTTTGTATAACAGTGGTGACACCTGGGTC

CAGAATTGTCAACAGTGCCGCTGCTTGCAAGGGGAAGTTGATTGTTGGCC

CCTGCCTTGCCCAGATGTGGAGTGTGAATTCAGCATTCTCCCAGAGAATG

AGTGCTGCCCGCGCTGTGTCACAGACCCTTGCCAGGCTGACACCATCCGC

AATGACATCACCAAGACTTGCCTGGACGAAATGAATGTGGTTCGCTTCAC

CGGGTCCTCTTGGATCAAACATGGCACTGAGTGTACTCTCTGCCAGTGCA

AGAATGGCCACATCTGTTGCTCAGTGGATCCACAGTGCCTTCAGGAACTG

TGAAGTTAACTGTCTCATGGGAGATTTCTGTTAAAAGAATGTTCTTTCAT

TAAAAGACCAAAAAGAAGTTAAAACTTAAATTGGGTGATTTGTGGGCAGC

TAAATGCAGCTTTGTTAATAGCTGAGTGAACTTTCAATTATGAAATTTGT

GGAGCTTGACAAAATCACAAAAGGAAAATTACTGGGGCAAAATTAGACCT

CAAGTCTGCCTCTACTGTGTCTCACATCACCATGTAGAAGAATGGGCGTA

CAGTATATACCGTGACATCCTGAACCCTGGATAGAAAGCCTGAGCCCATT

GGATCTGTGAAAGCCTCTAGCTTCACTGGTGCAGAAAATTTTCCTCTAGA

TCAGAATCTTCAAGAATCAGTTAGGTTCCTCACTGCAAGAAATAAAATGT

CAGGCAGTGAATGAATTATATTTTCAGAAGTAAAGCAAAGAAGCTATAAC

ATGTTGTGTACAGTACACTCTGAAAAGAAATCTGAAACAAGTTATTGTAA

TGATAAAAATAATGCACAGGCATGGTTACTTAATATTTTCTAACAGGAAA

AGTCATCCCTATTTCCTTGTTTTACTGCACTTAATATTATTTGGTTGAAT

TTGTTCAGTATAAGCTCGTTCTTGTGCAAAATTAAATAAATATTTCTCTT

ACCTTATAAAAAAAAAAAAAAA

In some embodiments, a biomarker may be a protein. In some embodiments, a biomarker may be an amino acid encoding a protein selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL1), and NEL-like protein 2 (NELL2). In some embodiments, the amino acid sequence is selected from the group consisting of SEQ ID NO's: 9, 10, 11, 12, 13, 14, 15, and 16.

*Homo sapiens* C2orf28; variant 1, Protein (Genbank Accession No. NP_057169)

(SEQ ID NO: 9)
MLHARCCLNQKGTILGLDLQNCSLEDPGPNFHQAHTTVIIDLQANPLKGD

LANTFRGFTQLQTLILPQHVNCPGGINAWNTITSYIDNQICQGQKNLCNN

TGDPEMCPENGSCVPDGPGLLQCVCADGFHGYKCMRQGSFSLLMFFGILG

ATTLSVSILLWATQRRKAKTS

*Homo sapiens* C2orf28; variant 2, Protein (Genbank Accession No. NP_542159.3)

(SEQ ID NO: 10)
MKTSAELHEQEKPPSSPRATGPGRLGHARGRGPDALRGGAAGPGRASSGA

PRERKMAPHDPGSLTTLVPWAAALLLALGVERALALPEICTQCPGSVQNL

SKVAFYCKTTRELMLHARCCLNQKGTILGLDLQNCSLEDPGPNFHQAHTT

VIIDLQANPLKGDLANTFRGFTQLQTLILPQHVNCPGGINAWNTITSYID

NQICQGQKNLCNNTGDPEMCPENGSCVPDGPGLLQCVCADGFHGYKCMRQ

GSFSLLMFFGILGATTLSVSILLWATQRRKAKTS

*Homo sapiens* C2orf28; variant 3, mRNA (Genbank Accession No. NP_001164266.1)

(SEQ ID NO: 11)
MAPHDPGSLTTLVPWAAALLLALGVERALALPEICTQCPGSVQNLSKVAF

YCKTTRELMLHARCCLNQKGTILGLDLQNCSLEDPGPNFHQAHTTVIIDL

QANPLKGDLANTFRGFTQLQTLILPQHVNCPGGINAWNTITSYIDNQICQ

GQKNLCNNTGDPEMCPENGSCVPDGPGLLQCVCADGFHGYKCMRQGSFSL

LMFFGILGATTLSVSILLWATQRRKAKTS

*Homo sapiens* Phospholipase C-like 1, Protein (Genbank Accession No. NP_006217.3)

(SEQ ID NO: 12)
MAEGAAGREDPAPPDAAGGEDDPRVGPDAAGDCVTAASGGRMRDRRSGVA

LPGAAGTPADSEAGLLEAARATPRRSSIIKDPSNQKCGGRKKTVSFSSMP

SEKKISSANDCISFMQAGCELKKVRPNSRIYNRFFTLDTDLQALRWEPSK

KDLEKAKLDISAIKEIRLGKNTETFRNNGLADQICEDCAFSILHGENYES

LDLVANSADVANIWVSGLRYLVSRSKQPLDFMEGNQNTPRFMWLKTVFEA

ADVDGNGIMLEDTSVELIKQLNPTLKEAKIRLKFKEIQKSKEKLTTRVTE

EEFCEAFCELCTRPEVYFLLVQISKNKEYLDANDLMLFLEAEQGVTHITE

DICLDIIRRYELSEEGRQKGFLAIDGFTQYLLSSECDIFDPEQKKVAQDM

TQPLSHYYINASHNTYLIEDQFRGPADINGYIRALKMGCRSVELDVSDGS

DNEPILCNRNNMTTHVSFRSVIEVINKFAFVASEYPLILCLGNHCSLPQQ

KVMAQQMKKVFGNKLYTEAPLPSESYLPSPEKLKRMIIVKGKKLPSDPDV

LEGEVTDEDEEAEMSRRMSVDYNGEQKQIRLCRELSDLVSICKSVQYRDF

ELSMKSQNYWEMCSFSETEASRIANEYPEDFVNYNKKFLSRIYPSAMRID

SSNLNPQFWNCGCQIVAMNFQTPGPMMDLHTGWFLQNGGCGYVLRPSIMR

DEVSYFSANTKGILPGVSPLALHIKIISGQNFPKPKGACAKGDVIDPYVC

IEIHGIPADCSEQRTKTVQQNSDNPIFDETFEFQVNLPELAMIRFVVLDD

DYIGDEFIGQYTIPFECLQPGYRHVPLRSFVGDIMEHVTLFVHIAITNRS

GGGKAQKRSLSVRMGKKVREYTMLRNIGLKTIDDIFKIAVHPLREAIDMR

ENMQNAIVSIKELCGLPPIASLKQCLLTLSSRLITSDNTPSVSLVMKDSF

PYLEPLGAIPDVQKKMLTAYDLMIQESRFLIEMADTVQEKIVQCQKAGME

FHEELHNLGAKEGLKGRKLNKATESFAWNITVLKGQGDLLKNAKNEAIEN

MKQIQLACLSCGLSKAPSSSAEAKSKRSLEAIEEKESSEENGKL

*Homo sapiens* Ephrin Receptor B1, Protein (Genbank Accession No. NP_004432.1)

(SEQ ID NO: 13)
MALDYLLLLLLASAVAAMEETLMDTRTATAELGWTANPASGWEEVSGYDE

NLNTIRTYQVCNVFEPNQNNWLLTTFINRRGAHRIYTEMRFTVRDCSSLP

NVPGSCKETFNLYYYETDSVIATKKSAFWSEAPYLKVDTIAADESFSQVD

FGGRLMKVNTEVRSFGPLTRNGFYLAFQDYGACMSLLSVRVFFKKCPSIV

QNFAVFPETMTGAESTSLVIARGTCIPNAEEVDVPIKLYCNGDGEWMVPI

GRCTCKPGYEPENSVACKACPAGTFKASQEAEGCSHCPSNSRSPAEASPI

CTCRTGYYRADFDPPEVACTSVPSGPRNVISIVNETSIILEWHPPRETGG

RDDVTYNIICKKCRADRRSCSRCDDNVEFVPRQLGLTECRVSISSLWAHT

PYTFDIQAINGVSSKSPFPPQHVSVNITTNQAAPSTVPIMHQVSATMRSI

TLSWPQPEQPNGIILDYEIRYYEKEHNEFNSSMARSQTNTARIDGLRPGM

VYVVQVRARTVAGYGKFSGKMCFQTLTDDDYKSELREQLPLIAGSAAAGV

VFVVSLVAISIVCSRKRAYSKEAVYSDKLQHYSTGRGSPGMKIYIDPFTY

EDPNEAVREFAKEIDVSFVKIEEVIGAGEFGEVYKGRLKLPGKREIYVAI

KTLKAGYSEKQRRDFLSEASIMGQFDHPNIIRLEGVVTKSRPVMIITEFM

ENGALDSFLRQNDGQFTVIQLVGMLRGIAAGMKYLAEMNYVHRDLAARNI

LVNSNLVCKVSDFGLSRYLQDDTSDPTYTSSLGGKIPVRWTAPEAIAYRK

FTSASDVWSYGIVMWEVMSFGERPYWDMSNQDVINAIEQDYRLPPPMDCP

AALHQLMLDCWQKDRNSRPRFAEIVNTLDKMIRNPASLKTVATITAVPSQ

PLLDRSIPDFTAFTTVDDWLSAIKMVQYRDSFLTAGFTSLQLVTQMTSED

LLRIGITLAGHQKKILNSIHSMRVQISQSPTAMA

*Homo sapiens* Syntrophin, Gamma 1, Protein (Genbank Accession No. NP_061840.1)

(SEQ ID NO: 14)
MDFRTACEETKTGICLLQDGNQEPPFKVRLHLAKDILMIQEQDVICVSGEP

FYSGERTVTIRRQTVGGFGLSIKGGAEHNIPVVVSKISKEQRAELSGLLF

IGDAILQINGINVRKCRHEEVVQVLRNAGEEVTLTVSFLKRAPAFLKLPL

NEDCACAPSDQSSGTSSPLCDSGLHLNYHPNNTDTLSCSSWPTSPGLRWE

KRWCDLRLIPLLHSRFSQYVPGTDLSRQNAFQVIAVDGVCTGIIQCLSAE

DCVDWLQAIATNISNLTKHNIKKINRNFPVNQQIVYMGWCEAREQDPLQD

RVYSPTFLALRGSCLYKFLAPPVTTWDWTRAEKTFSVYEIMCKILKDSDL

LDRRKQCFTVQSESGEDLYFSVELESDLAQWERAFQTATFLEVERIQCKT

YACVLESHLMGLTIDFSTGFICFDAATKAVLWRYKFSQLKGSSDDGKSKI

KFLFQNPDTKQIEAKELEFSNLFAVLHCIHSFFAAKVACLDPLFLGNQAT

ASTAASSATTSKAKYTT

*Homo sapiens* NELL1, Protein (Genbank Accession No. AAH96102.1)

(SEQ ID NO: 15)
MPMDLILVVWFCVCTARTVVGFGMDPDLQMDIVTELDLVNTTLGVAQVSG

MHNASKAFLFQDIEREIHAAPHVSEKLIQLFRNKSEFTILATVQQKPSTS

GVILSIRELEHSYFELESSGLRDEIRYHYIHNGKPRTEALPYRMADGQWH

KVALSVSASHLLLHVDCNRIYERVIDPPDTNLPPGINLWLGQRNQKHGLF

KGIIQDGKIIFMPNGYITQCPNLNHTCPTCSDFLSLVQGIMDLQELLAKM

TAKLNYAETRLSQLENCHCEKTCQVSGLLYRDQDSWVDGDHCRNCTCKSG

AVECRRMSCPPLNCSPDSLPVHIAGQCCKVCRPKCIYGGKVLAEGQRILT

KSCRECRGGVLVKITEMCPPLNCSEKDHILPENQCCRVCRGHNFCAEGPK

CGENSECKNWNTKATCECKSGYISVQGDSAYCEDIDECAAKMHYCHANTV

CVNLPGLYRCDCVPGYIRVDDFSCTEHDECGSGQHNCDENAICTNTVQGH

SCTCKPGYVGNGTICRAFCEEGCRYGGTCVAPNKCVCPSGFTGSHCEKDI

DECSEGIIECHNHSRCVNLPGWYHCECRSGFHDDGTYSLSGESCIDIDEC

ALRTHTCWNDSACINLAGGFDCLCPSGPSCSGDCPHEGGLKHNGQVWTLK

EDRCSVCSCKDGKIFCRRTACDCQNPSADLFCCPECDTRVTSQCLDQNGH

KLYRSGDNWTHSCQQCRCLEGEVDCWPLTCPNLSCEYTAILEGECCPRCV

SDPCLADNITYDIRKTCLDSYGVSRLSGSVWTMAGSPCTTCKCKNGRVCC

SVDFECLQNN

*Homo sapiens* NELL2, Protein (Genbank Accession No. AAH20544.1)

(SEQ ID NO: 16)
MESRVLLRTFCLIFGLGAVWGLGVDPSLQIDVLTELELGESTTGVRQVPG

LHNGTKAFLFQDTPRSIKASTATAEQFFQKLRNKHEFTILVTLKQTHLNS

GVILSIHHLDHRYLELESSGHRNEVRLHYRSGSHRPHTEVFPYILADDKW

HKLSLAISASHLILHIDCNKIYERVVEKPSTDLPLGTTFWLGQRNNAHGY

FKGIMQDVQLLVMPQGFIAQCPDLNRTCPTCNDFHGLVQKIMELQDILAK

TSAKLSRAEQRMNRLDQCYCERTCTMKGTTYREFESWIDGCKNCTCLNGT

IQCETLICPNPDCPLKSALAYVDGKCCKECKSICQFQGRTYFEGERNTVY

SSSGVCVLYECKDQTMKLVESSGCPALDCPESHQITLSHSCCKVCKGYDF

CSERHNCMENSICRNLNDRAVCSCRDGFRALREDNAYCEDIDECAEGRHY

CRENTMCVNTPGSFMCICKTGYIRIDDYSCTEHDECITNQHNCDENALCF

NTVGGHNCVCKPGYTGNGTTCKAFCKDGCRNGGACIAANVCACPQGFTGP

SCETDIDECSDGFVQCDSRANCINLPGWYHCECRDGYHDNGMFSPSGESC

EDIDECGTGRHSCANDTICFNLDGGYDCRCPHGKNCTGDCIHDGKVKHNG

QIWVLENDRCSVCSCQNGFVMCRRMVCDCENPTVDLFCCPECDPRLSSQC

LHQNGETLYNSGDTWVQNCQQCRCLQGEVDCWPLPCPDVECEFSILPENE

CCPRCVTDPCQADTIRNDITKTCLDEMNVVRFTGSSWIKHGTECTLCQCK

NGHICCSVDPQCLQEL

In some embodiments, the amino acid sequence encodes a truncated version of the full length proteins selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL1), and NEL-like protein 2 (NELL2). In some embodiments, the amino acid sequence encodes a fragment at least 15-100 amino acids in length. In some embodiments the amino acid sequence encodes a splice variant of a protein selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL1), and NEL-like protein 2 (NELL2). In some embodiments, the amino acid sequence of SEQ ID NO's: 9, 10, 11, 12, 13, 14, 15, or 16 represents the wild-type and/or reference sequence for the protein.

Diagnosing and/or Characterizing Calcium Disorders

In accordance with the present invention, biomarkers are useful, among other things, to diagnose and/or characterize one or more aspects of calcium disorders and/or subjects suffering from, susceptible to and/or receiving treatment for them.

Detect and/or Quantify Gene or Gene Products

The present invention, among other things, provides systems for detection and/or quantification of a gene and or gene products (i.e., "biomarkers") whose level, form and/or activity can be objectively measured, evaluated and/or quantified to diagnose and/or characterize a calcium disorder in a subject. In particular, for example, the present invention identifies certain genes and/or gene products whose level, form, and/or activity correlates with resistance to one or more negative effects observed with certain NBP therapeutic regimens. Alternatively or additionally, in some embodiments, the present invention identifies certain genes and/or gene products whose level, form, and/or activity correlates with one or more positive effects observed with certain NBP therapeutic regimens. In some embodiments, the present invention identifies certain genes and/or gene products whose level, form, and/or activity correlates with resistance to cytotoxic effects of one or more bisphosphonate agent(s). In some embodiments, identified genes and/or gene products provide selective resistance to a specific class of bisphosphonate agent. In some embodiments, class of bisphosphonate agent comprises non-nitrogenous bisphosphonates. In some embodiments, the class of bisphosphonate agent comprises nitrogenous bisphosphonates.

In some embodiments, the present invention identifies certain genes and/or gene products (i.e., "biomarkers") whose level, form and/or activity can be objectively measured, evaluated and/or quantified.

In some embodiments, genes may be identified by characterizing nucleic acid extracted from a sample. In some embodiments, the nucleic acid comprises a deoxyribonucleic acid or a ribonucleic acid. In some embodiments, the nucleic acid comprises DNA, RNA, mRNA or cDNA. In some embodiments, nucleic acid may be extracted from the sample prior to analysis. In some embodiments, nucleic acid may be extracted from the subject using and extraction method know to those of skill in the art. (see, for example, J. Sambrook et al., "Molecular Cloning: A Laboratory Manual", 1989, $2^{nd}$ Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNases. Isolated total RNA may then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.). In some embodiments an antibody may be an anti-peptide antibody. In some embodiments an antibody may be recombinantly produced or chemically synthesized, or produced by a hybridoma or other engineered cell line; in some embodiments, an antibody may be obtained from a natural source. In some embodiments an antibody is identified using a display technique such as phage display.

In some embodiments, after extraction, mRNA is amplified, and transcribed into cDNA, which can then serve as template for multiple rounds of transcription by an appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, $2^{nd}$ Ed., Cold Spring Harbour Laboratory Press: New York; "Short Protocols in Molecular Biology", F. M. Ausubel (Ed.), 2002, $5^{th}$ Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each probe being monitored, or using thermostable DNA polymerases (such as avian myeloblastosis virus reverse transcriptase or Moloney murine leukemia virus reverse transcriptase).

In some embodiments, nucleic acid probes may be used for the detection of polynucleotide sequences in a sample. In some embodiments, the nucleic acid probe may be produced synthetically, or from an existing nucleic acid sample, using conventional methods known to those skilled in the art. Suitable probes may be based on nucleic acid sequences encoding at least 5 sequential amino acids from regions of nucleic acids encoding a biomarker, and may comprise about 15 to about 50 nucleotides. A nucleic acid probe may be labeled with a detectable moiety or label. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well known in the art (for a review of labeling protocols, label detection techniques and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153).

In some embodiments, nucleic acid probes may be used for hybridization techniques to detect polynucleotides encoding biomarkers. The technique generally involves contacting and incubating nucleic acid molecules in a sample obtained from a subject with the nucleic acid probes under conditions such that specific hybridization takes place between the nucleic acid probes and the complementary sequences in the nucleic acid molecules. Typically, stringent hybridization conditions are used. In some embodiments, "stringent hybridization conditions" refer to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In some embodiments, stringent hybridization conditions should not allow for hybridization of two nucleic acids which differ over a stretch of 20 contiguous nucleotides by more than two bases. After incubation, the non-hybridized nucleic acids are removed, and the presence and amount of nucleic acids that have hybridized to the probes are detected and quantified.

In some embodiments, nucleic acid molecules comprising polynucleotide sequences coding for a gene or gene product may be used for amplification of specific polynucleotide sequences using an amplification method such as PCR (e.g., RT-PCR), followed by analysis of the amplified molecules using techniques known in the art. Suitable primers can be routinely designed by one skilled in the art. In order to maximize hybridization under assay conditions, primers and probes employed in the methods of the invention generally have at least 60%, preferably at least 75% and more preferably at least 90% identity to a portion of nucleic acids encoding a biomarker.

In some embodiments, identification of one or more single nucleotide polymorphisms (SNP), using one or more of the techniques described above, may be used to is identify a gene. In some embodiments, the nucleic acid sequence may be interrogated, using one or more of the techniques described above, to identify insertions, deletions, frame shifts or silent mutations in the gene or gene product.

In some embodiments, the gene or gene product may be differentially expressed between a subject with a calcium disorder and normal healthy subject. In some embodiments, "differential expression profiling" may be used to identify gene or gene products of a calcium disorder. As used herein, the term "differential expression profiling" refers to methods of comparing the gene or protein expression levels or patterns in two or more samples (e.g., samples obtained from a subject with a calcium disorder vs. control samples obtained from a healthy control subject). Typically, a gene or gene product is differentially expressed if the difference (e.g., increase or decrease) in the expression level or pattern between two samples is statistically significant (i.e., the difference is not caused by random variations). In some embodiments, a gene or protein is differentially expressed if the difference in the expression level between two samples is more than 20%, 30%, 40%, 50%, 60%, 70%, 80%, 90%, 1-fold, 1.2-fold, 1.5-fold, 1.75-fold, 2-fold, 2.25-fold, 2.5-fold, 2.75-fold, or 3-fold.

In some embodiments, expression levels of nucleic acids in a sample may be performed by any suitable method, including, but not limited to, hybridization (e.g., Southern or Northern analysis), polymerase chain reaction (PCR) (see, for example, U.S. Pat. Nos., 4,683,195; 4,683,202, and 6,040, 166; "*PCR Protocols: A Guide to Methods and Applications*", Innis et al. (Eds.), 1990, Academic Press: New York), reverse transcriptase PCR (RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

In some embodiments, hybridization and amplification techniques described herein may be used to assay qualitative and quantitative aspects of expression of nucleic acid molecules comprising polynucleotide sequences coding for genes or gene products described herein. In some embodiments, oligonucleotides or longer fragments from nucleic acids encoding each gene or gene product may be used as targets in a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

In some embodiments, gene products may be identified by characterizing protein extracted from a sample. In some embodiments, protein may be extracted from the sample prior to analysis. In some embodiments, protein may be extracted without or with limited processing of the sample. For example, protein extract may be prepared from a sample. In some embodiments, a protein extract contains the total protein content. In some embodiments, protein extracts containing one or more of membrane proteins, nuclear proteins, and cytosolic proteins may be prepared. Methods of protein extraction are well known in the art (see, for example "*Protein Methods*", D. M. Bollag et al., 2$^{nd}$ Ed., 1996, Wiley-Liss; "*Protein Purification Methods: A Practical Approach*", E. L. Harris and S. Angal (Eds.), 1989; "*Protein Purification Techniques: A Practical Approach*", S. Roe, 2$^{nd}$ Ed., 2001, Oxford University Press; "*Principles and Reactions of Protein Extraction, Purification, and Characterization*", H. Ahmed, 2005, CRC Press: Boca Raton, Fla.). Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kit(s) most appropriate for a particular situation. After the protein extract has been obtained, the protein concentration of the extract is preferably standardized to a value being the same as that of the control sample in order to allow signals of the protein markers to be quantitated. Such standardization can be made using photometric or spectrometric methods or gel electrophoresis.

In some embodiments, protein expression levels may be used to identify gene products in a sample, using any suitable method know in the art. (see, for example, E. Harlow and A. Lane, "*Antibodies: A Laboratories Manual*", 1988, Cold Spring Harbor Laboratory: Cold Spring Harbor, N.Y.). In general, protein expression levels are determined by contacting a biological sample obtained from a subject with binding agents for one or more of proteins; detecting, in the sample, the levels of one or more proteins that bind to the binding agents; and comparing the levels of one or more proteins in the sample with the levels of the corresponding proteins in a control sample. In some embodiments, a binding agent may comprise an entity such as a polypeptide or antibody that specifically binds to a protein. An entity "specifically binds" to a polypeptide if it reacts/interacts at a detectable level with the polypeptide but does not react/interact detectably with peptides containing unrelated sequences or sequences of different polypeptides.

In some embodiments, a suitable binding agent is an antibody specific for a protein selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL-1) and NEL-like protein 2 (NELL-2). In some embodiments, a suitable antibody can specifically bind to a particular form of a protein, for example, a phosphorylated protein. Suitable antibodies for use in the methods of the present invention include monoclonal and polyclonal antibodies, immunologically active fragments (e.g., Fab or (Fab)$_2$ fragments), antibody heavy chains, humanized antibodies, antibody light chains, and chimeric antibodies. Antibodies, including monoclonal and polyclonal antibodies, fragments and chimeras, may be prepared using methods known in the art (see, for example, R.G. Mage and E. Lamoyi, in "*Monoclonal Antibody Production Techniques and Applications*", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czernik et al., Neuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S, Neuberger et al., Nature, 1984, 312: 604-608; S. Takeda et al., Nature, 1985, 314: 452-454). Antibodies to be used in the systems of the invention can be purified by methods well known in the art (see, for example, S. A. Minden, "*Monoclonal Antibody Purification*", 1996, IBC Biomedical Library Series: Southbridge, Mass.). For example, antibodies can be affinity-purified by passage over a column to which a protein marker or fragment thereof is bound. The bound antibodies can then be eluted from the column using a buffer with a high salt concentration and/or low pH. In some embodients, antibodies to may be used which are obtained from scientific or commercial sources (e.g., Cayman Chemical).

In certain embodiments, binding agents are directly or indirectly labeled with a detectable moiety. In some embodiment, the role of the detectable agent is to facilitate the detection step of the diagnostic method by allowing visualization of the complex formed by binding of the binding agent to the protein (or analog or fragment thereof). In some embodiments, it is preferred that the detectable agent is selected such that it generates a signal which can be measured and whose intensity is related (preferably proportional) to the amount of protein marker present in the sample being analyzed. Methods for labeling biological molecules such as polypeptides and antibodies are well-known in the art (see, for example, "*Affinity Techniques. Enzyme Purification: Part B*", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Any of a wide variety of detectable agents can be used in the practice of the present invention. In some embodiments, detectable agents may include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In some embodiments, binding agents (e.g., antibodies) may be immobilized on a carrier or support (e.g., a bead, a magnetic particle, a latex particle, a microtiter plate well, a cuvette, or other reaction vessel). Examples of suitable carrier or support materials include, but are not limited to, agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinyl-ether-maleic acid copolymer, amino acid copolymer, ethylene-maleic acid copolymer, nylon, silk, and the like. Binding agents may be indirectly immobilized using second binding agents specific for the first binding agents (e.g., mouse antibodies specific for the protein markers may be immobilized using sheep anti-mouse IgG Fc fragment specific antibody coated on the carrier or support).

In some embodiments, protein expression levels in a biological sample may be determined using immunoassays. Examples of such assays are time resolved fluorescence immunoassays (TR-FIA), radioimmunoassays, enzyme immunoassays (e.g., ELISA), immunofluorescence immunoprecipitation, latex agglutination, hemagglutination, Western blot, and histochemical tests, which are conventional methods well-known in the art. As will be appreciated by one skilled in the art, the immunoassay may be competitive or non-competitive. Methods of detection and quantification of the signal generated by the complex formed by binding of the binding agent with the protein marker will depend on the nature of the assay and of the detectable moiety (e.g., fluorescent moiety).

In some embodiments, protein expression levels may be determined using mass spectrometry based methods or image (including use of labeled ligand) based methods known in the art for the detection of proteins. In some embodiments, detection methods include, but are not limited to, 2D-gel electrophoresis and proteomics-based methods. Proteomics, which studies the global changes of protein expression in a sample, can include the following steps: (1) separation of individual proteins in a sample by electrophoresis (1-D PAGE), (2) identification of individual proteins recovered from the gel (e.g., by mass spectrometry or N-terminal sequencing), and (3) analysis of the data using bioinformatics.

In some embodiments, expression levels may be determined for a sample being analyzed, by comparing its expression level to the expression levels in one or more control samples. Correction may be carried out using different methods well known in the art. For example, the protein concentration of a sample may be standardized using photometric or spectrometric methods or gel electrophoresis (as already mentioned above) before the sample is analyzed. In case of samples containing nucleic acid molecules, correction may be carried out by normalizing the levels against reference genes (e.g., housekeeping genes) in the same sample. Alternatively or additionally, normalization can be based on the mean or median signal (e.g., Ct in the case of RT-PCR) of all assayed genes or a large subset thereof (global normalization approach).

Kits

The present invention, among other things, provides kits comprising various reagents and materials useful for carrying out systems and/or methods according to the present invention. The diagnosis/characterization/staging/monitoring procedures described herein may be performed by diagnostic laboratories, experimental laboratories, or practitioners. The invention provides kits that may be used in these different settings.

For example, materials and reagents for characterizing samples, measuring gene and gene products (e.g., protein or nucleic acid levels), diagnosing a calcium disorder, characterizing severity, staging the disease, and/or monitoring treatment response in a subject may be assembled together in a kit. In some embodiments, kits comprise at least one or more reagents that specifically detect protein or nucleic acid expression levels of one or more biomarkers (e.g., Phospholipase C-like 1(PLCL-1), Ephrin receptor B1 (EPHB1), Syntrophin Gamma 1(SNTG1), C2orf28 (APR3), NEL-like 1 (NELL-1) and NEL-like 2 (NELL-2), and instructions for using the kit according to the systems of the invention.

Each kit may preferably comprise the reagent which renders the procedure specific. In some embodiments, for detecting/quantifying a protein (or an analog or fragment thereof) the reagent that specifically detects expression levels of the protein may be an antibody that specifically binds to the protein (or analog or fragment thereof). In some embodiments, for detecting/quantifying a nucleic acid molecule, a polynucleotide sequence coding a biomarker, the reagent that specifically detects expression levels may be a nucleic acid probe complementary to the polynucleotide sequence (e.g., cDNA or an oligonucleotide). In some embodiments, the nucleic acid probe may or may not be immobilized on a substrate surface (e.g., beads, a microarray, and the like).

In some embodiments, kits or other articles of manufacture may include one or more containers to hold various reagents. Suitable containers include, for example, bottles, vials, syringes (e.g., pre-filled syringes), ampoules. The container may be formed from a variety of materials such as glass or plastic.

In some embodiments, kits may include suitable control levels or control samples for determining control levels as described herein. In some embodiments, kits may include instructions for using the kit according to one or more methods of the invention and may comprise instructions for processing the biological sample obtained from the subject and/or for performing the test, instructions for interpreting the results as well as a notice in the form prescribed by a governmental agency (e.g., FDA) regulating the manufacture, use or sale of pharmaceuticals or biological products.

Identifying and/or Characterizing Agents that Treat Disorders, and Uses Thereof

The present invention, among other things, provides systems for identifying and/or characterizing agents useful in treatment of calcium disorders and/or calcium disorder therapy. In some embodiments, such agents are identified and/or characterized based on an effect on one or more biomarkers as described herein and/or one or more other aspects of a calcium disorder or response to therapy in a subject. In some embodiments compositions, methods, and/or reagents useful for identifying and/or characterizing agents are provided.

In some embodiments, systems may be used to identify genes encoding proteins involved in the cellular pathway associated with the NBP treatment. In some embodiments, systems may be used to identify and/or characterize agents that interact (e.g. bind to, increase/decrease expression, alter transcription, alter subcellular localization) with gene or gene products within a subject suffering from a calcium disorder. In some embodiments, systems may be used to identify and/or characterize agents that bind to proteins that provide resistance to cytotoxic effects of NPB therapy. In some embodiments, systems may be used to identify and/or characterize agents that alleviate the side effects of NBP therapy. In some embodiments, systems may be used to identify and/or characterize agents that bind to proteins that are differentially expressed in a subject suffering from a calcium disorder. In some embodiment, systems may be used to identify and/or characterize agents that bind to a protein selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL1) and NEL-like protein 2 (NELL2). In some embodiments, systems may be used to identify and/or characterize agents that interact (e.g. bind to, increase/decrease expression, alter transcription, alter subcellular localization), with a protein associated with one or more of the proteins selected from the group consisting of C2orf28 (APR3), Phospholipase C-like 1(PLCL-1), Ephrin receptor B1 (EPHB1), Syntrophin Gamma 1(SNTG1), NEL-like protein 1 (NELL1), NEL-like protein 2 (NELL2), such as, for example, LLP (Stelzl et. al., Cell, 2005, 122:957-968; Zou et. al., 2011, FEBS Letters, 585:2410-2418; both of which are hereby incorporated by reference). In some embodiments, systems may be used to identify and/or characterize agents with direct binding interaction with any one of the proteins selected form the group consisting of C2orf28 (APR3), Phospholipase C-like 1(PLCL-1), Ephrin receptor B1 (EPHB1), Syntrophin Gamma 1(SNTG1), NEL-Like 1 (NELL1), NEL-like 2 (NELL2) and combinations thereof.

In some embodiments, the present invention provides methodologies for identifying and/or characterizing agents of interest by a method that involves analyzing, in silico and/or in situ, interaction of the agent with crystal structure of a biomarker described herein (e.g., TBONE). In some embodiments, crystals are prepared with and without agent of interest, and one or more features of the agent-biomarker interaction are defined. In some embodiments, a crystal structure of a biomarker alone (i.e., not interacting with an agent) is obtained or provided, and potential interactions with agent structures are modeled in silico. In some embodiments, a crystal structure of a biomarker with a reference agent is obtained or provided, and potential interactions between the biomarker and one or more agent structures are compared with those between the biomarker and the reference agent. In some embodiments, crystal structures of a biomarker and one or more agents are obtained or provided and are compared with one another and/or with that of the biomarker with a reference agent and/or with that of the biomarker alone. In some embodiments, results of crystal structure analyses are considered when designing or selecting agent structures.

In some embodiments, systems may be used to identify and/or characterize agents by screened from large libraries of synthetic or natural compounds. For example, numerous means are available for random and directed synthesis of saccharide, peptide, small molecule and/or nucleic acid based compounds. Alternatively, libraries of natural agents from bacterial, fungal, plant and animal extracts are available or readily producible. Additionally, natural and synthetically produced libraries and compounds are readily modified through conventional chemical, physical, and biochemical means.

In some embodiments, agents may be modified to enhance efficacy, stability, pharmaceutical compatibility, and the like. In some embodiments, structural identification of an agent may be used to identify and/or characterize, generate, and/or screen additional agents. For example, where peptide agents are identified, they may be modified in a variety of ways to enhance their stability, such as using an unnatural amino acid, such as a D-amino acid, particularly D-alanine, by functionalizing the amino or carboxyl terminus, e.g., for the amino group, acylation or alkylation, and for the carboxyl group, esterification or amidification, or the like. Other methods of stabilization may include encapsulation, for example, in liposomes, etc.

Agents may be prepared in a variety of ways known to those skilled in the art. For example, peptides under about 60 amino acids can be readily synthesized today using conventional commercially available automatic synthesizers. In some embodiments, DNA sequences may be prepared encoding the desired peptide and inserted into an appropriate expression vector for expression in a prokaryotic or eukaryotic host. A wide variety of expression vectors are available today and may be used in conventional ways for transformation of a competent host for expression and isolation. In some embodiments, an open reading frame encoding the desired peptide may be joined to a signal sequence for secretion, so as to permit isolation from the culture medium. Methods for preparing the desired sequence, inserting the sequence into an expression vector, transforming a competent host, and growing the host in culture for production of the product may be found in U.S. Pat. Nos. 4,710,473, 4,711,843 and 4,713,339.

In some embodiments, systems may be used to identify and/or characterize agents that mimic the binding action of a agent known to treat a calcium disorder, such as, for example, those agents listed in Table 1. In some embodiments, systems may be used to identify and/or characterize agents that can mimic the cellular effects, binding affinity or binding specificity of an NBP. In some embodiments, systems may be used for identifying and/or characterize an agent that results in reduced or increased function (e.g., expression and/or secretion of bone remodeling related proteins: alkaline phosphatase for osteoblasts; tartrate acid resistant phosphate for osteoclasts) or cellular death (e.g. apoptosis) in an osteoblast, osteoclast or osteocyte. In some embodiments, systems may be used to identify and/or characterize agents that prevent cell division. In some embodiments, systems may be used to identify and/or characterize agents that may result in an increase and/or decrease in one or more of bone density, bone mass, membrane ossification, accumulation of hydroxyapatite and collagen in a subject. In some embodiments, systems may be used to identify and/or characterize nucleic acid agents for treating a calcium disorder. In some embodiments, the nucleic acid is a ribonucleic acid, such as, for example, siRNA, that is able to increase/decrease expression, alter transcription or subcellular localization of gene or gene products associated with a calcium disorder. In some embodiments, agents may comprises a nucleic acid sequence selected from the group consisting of SEQ ID NO's.: 1, 2, 3, 4, 5, 6, 7, and 8. In some embodiments, agents may comprises a protein and/or fragment, encoded by the amino acid sequence selected from the group consisting of SEQ ID NO's.: 9, 10, 11, 12, 13, 14, 15, and 16.

In some embodiments, agents (e.g., antibody agents) may be used that binds to a protein that is differentially expressed in a subject suffering from a calcium disorder. In some embodiments, agents (e.g., antibody agents) may be used that bind to a protein selected from the group consisting of C2orf28 (APR3), Phospholipase C-like 1(PLCL-1), Ephrin receptor B1 (EPHB1), Syntrophin Gamma 1(SNTG1), NEL-Like 1 (NELL1), and NEL-like 2 (NELL2). In some embodiments, agents (e.g., antibody agents) may be used that bind to an extracellular target (e.g., an extracellular domain of a target protein). In some particular embodiments, agents (e.g., antibody agents) may be used that bind to an extracellular portion of C2orf28 (ARP3).

As will be appreciated by those skilled in the art, the present invention provides, in some embodiments, various cells and cell lines, for example, that are engineered or selected to have altered expression, level, sequence, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product as compared with cells or cell lines that are not so engineered or selected (e.g., parental cells or cells of comparable cell lines of the same cell type). Cells may be engineered, e.g., to have increased expression of a gene product, by introduction of a nucleic acid, e.g., an expression vector, comprising a sequence that encodes a C2orf28 (APR3), NELL1, NELL2, Phospholipase C-like 1(PLCL-1), Ephrin receptor B1 (EPHB1), or Syntrophin Gamma 1(SNTG1) mRNA or protein. Cells may be engineered, e.g., to have decreased expression of a gene product, by introduction of a nucleic acid, e.g., an expression vector, comprising a sequence that encodes a short hairpin RNA (shRNA) or other RNAi agent that inhibits expression of C2orf28 (APR3), NELL1, NELL2, Phospholipase C-like 1(PLCL-1), Ephrin receptor B1 (EPHB1), or Syntrophin Gamma 1(SNTG1) or by at least partial deletion or by disruption of a C2orf28 (APR3), NELL1, NELL2, Phospholipase C-like 1(PLCL-1), Ephrin receptor B1 (EPHB1), or Syntrophin Gamma 1(SNTG1) gene.

In some embodiments, engineered cells contain or comprise a modification that is transient (e.g., transient transfection); in some embodiments, engineered cells contain or comprise a modification that is stable. A stable modification may comprise heritable alteration of the genome (e.g., integration/insertion of a nucleic acid into the genome) or introduction of a stable episome that is inherited with high fidelity by daughter cells. In some embodiments a provided engineered cell or cell line expresses a tagged or detectably labeled version of a C2orf28 (APR3), NELL1, NELL2, Phospholipase C-like 1(PLCL-1), Ephrin receptor B1 (EPHB1), or Syntrophin Gamma 1(SNTG1) protein. Examples of tags include polyhistidine-tag (e.g., 6×-His tag), glutathione-S-transferase, maltose binding protein, NUS tag, SNUT tag, Strep tag, epitope tags such as V5, HA, Myc, or FLAG. In some embodiments a tag or label is useful for detecting a protein that comprises it. For example, localization of the protein may be assessed.

In some embodiments engineered or selected cells or cell lines are useful to identify or characterize an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product. For example, in some embodiments an agent capable of selectively killing or inducing apoptosis or inhibiting proliferation of cells that express C2orf28 (APR3), NELL1, NELL2, Phospholipase C-like 1(PLCL-1), Ephrin receptor B1 (EPHB1), or Syntrophin Gamma 1(SNTG1) as compared with cells that do not express or have reduced expression of C2orf28 (APR3), NELL1, NELL2, Phospholipase C-like 1(PLCL-1), Ephrin receptor B1 (EPHB1), or Syntrophin Gamma 1(SNTG1) may be identified. In some embodiments cell viability and/or proliferation may be assessed using, e.g., a cell membrane integrity assay, a cellular ATP-based viability assay, a, a BrdU, EdU, or H3-Thymidine incorporation assay, a DNA content assay using a nucleic acid dye, such as Hoechst Dye, DAPI, Actinomycin D, 7-aminoactinomycin D or propidium iodide, a cellular metabolism assay such as AlamarBlue, MTT, XTT, and CellTitre Glo, etc. In some embodiments apoptosis may be assessed, e.g., using TUNEL or detecting a marker of apoptosis such as annexin V or phosphatidylserine on the cell surface.

In some embodiments an agent capable of selectively modulating (e.g., increasing or decreasing) one or more indicators of calcium metabolism, tissue mineralization, cell signaling, and/or NBP activity in cells that express C2orf28 (APR3), NELL1, NELL2, Phospholipase C-like 1(PLCL-1), Ephrin receptor B1 (EPHB1), or Syntrophin Gamma 1(SNTG1) as compared with cells that do not express or have reduced expression of C2orf28 (APR3), NELL1, NELL2, Phospholipase C-like 1(PLCL-1), Ephrin receptor B1 (EPHB1), or Syntrophin Gamma 1(SNTG1) (e.g., wild type cells) may be identified. In some embodiments, e.g., embodiments relating to comparison between cells or cell lines, a first cell or cell population may be considered test cell(s) and a second cell or cell population may be considered control cell(s). In some embodiments an agent capable of selectively modulating one or more indicators of calcium metabolism, tissue mineralization, cell signaling, and/or NBP activity in cells that express increased levels of C2orf28 (APR3), NELL1, NELL2, Phospholipase C-like 1(PLCL-1), Ephrin receptor B1 (EPHB1), or Syntrophin Gamma 1(SNTG1) as compared with control cells may be identified. In some embodiments, expression levels differ by a factor of between 1.1 and 100-fold, or more. For example, in some embodiments a first cell or cell line expresses a mRNA or protein at a level at least 2, 3, 5, 10, 20, or 50-fold as great as the level at which such mRNA or protein is expressed by a second cell or cell line.

In some embodiments co-cultures comprising cells having different levels of expression of C2orf28 (APR3), NELL1, NELL2, Phospholipase C-like 1(PLCL-1), Ephrin receptor B1 (EPHB1), or Syntrophin Gamma 1(SNTG1) are provided. For example, a first population of cells may have increased or decreased expression of C2orf28 as compared with a second population of cells. Such co-cultures are contacted with one or more agents for a suitable time period. In some embodiments, agents that differentially affect survival or proliferation (e.g., as assessed by cell number) may thereby be identified.

In some embodiments first and second cells or cell populations (e.g., cell lines) are genetically matched. In some embodiments first and second cell populations originate from the same subject, sample, or cell line, so that the first and second cell populations are genetically matched. One or both cell populations comprises a genetic modification that alters expression, level, sequence, form, or activity of C2orf28 (APR3), NELL1, NELL2, Phospholipase C-like 1(PLCL-1), Ephrin receptor B1 (EPHB1), or Syntrophin Gamma 1(SNTG1). In some embodiments the ratio of first to second cell populations in a co-culture is between 1:99 and 99:1, e.g., between 10:90 and 90:10, e.g., between 25:75 and 75:25, e.g., 50:50.

In some embodiments a composition comprising an isolated or purified C2orf28 (APR3), NELL1, NELL2, Phospholipase C-like 1(PLCL-1), Ephrin receptor B1 (EPHB1), or Syntrophin Gamma 1(SNTG1) protein is provided. In some embodiments the composition comprises an aqueous medium, e.g., water. In some embodiments the composition comprises a lipid. In some embodiments the composition comprises a detergent. In some embodiments the protein is recombinantly produced. In some embodiments the protein is crystallized or present at a concentration suitable for structure determination or crystallization. In some embodiments the composition further comprises an NBP. In some embodiments a structure is determined using NMR or X-ray crystallography.

In some embodiments agents are contacted with C2orf28 (APR3), NELL1, NELL2, Phospholipase C-like 1(PLCL-1), Ephrin receptor B1 (EPHB1), or Syntrophin Gamma 1(SNTG1) protein, and the ability of the agent to bind to the protein is determined, e.g., in order to identify one or more agents that bind to the protein. In some embodiments the protein, agent, or both, is in solution. In some embodiments the protein, agent, or both, is attached to a support, e.g., a bead, microparticle, etc.

In some embodiments agents are contacted with cells that express C2orf28 (APR3), NELL1, NELL2, Phospholipase C-like 1(PLCL-1), Ephrin receptor B1 (EPHB1), or Syntrophin Gamma 1(SNTG1) protein and the ability of the agent to bind to or modulate expression, activity, level, or form of the protein is determined, e.g., in order to identify one or more agents that bind to or modulate expression, activity, level, or form the protein.

In some embodiments a high throughput screen is performed. In some embodiments agents are contacted with protein or cells in individual wells of a microwell plate, e.g., a 96, 384, 1536, or 3456-well microwell plate.

In some embodiments an agent is not a cell culture medium component, e.g., for cells of the cell type of the mammalian cell with which the agent is contacted. One of ordinary skill in the art will be aware of agents that are cell culture medium components. In some embodiments, e.g., if the agent is a cell culture medium component, the agent is present at a non-standard concentration. Any one or more agent(s) may be explicitly excluded.

In some embodiments, cells used in a screen, system, composition, assay, or method of identifying and/or characterizing agents are mammalian cells, e.g., human cells. In some embodiments cells are bone cells, e.g., osteoblasts, osteoclasts, osteocytes, or a combination thereof.

In some embodiments an agent is tested (e.g., by contacting the agent with protein or cells or administering the agent to a non-human animal) in the presence of an NBP. The ability of the agent to enhance or inhibit one or more effects of the NBP is assessed. In some embodiments, agents that may enhance the therapeutic efficacy of an NBP or may reduce the likelihood of one or more deleterious effects of an NBP may be identified. In some embodiments, agents whose effect(s) of interest are specific to NBPs as compared with BPs are identified, characterized, and/or used. In some embodiments agents identified, characterized, or used may be useful for combined therapy with an NBP.

In some embodiments an agent described herein or identified as described herein, e.g., an agent that binds to or modulates expression, level, modification, form, or activity of a biomarker selected from the group consisting of C2orf28 (APR3), NELL1, NELL2, Phospholipase C-like 1(PLCL-1), Ephrin receptor B1 (EPHB1), or Syntrophin Gamma 1(SNTG1) and combinations thereof is tested in an ex vivo (outside the body) system that may serve as a model of a calcium disorder. In some embodiments an ex vivo system comprises bone cells in culture. In some embodiments bone cells comprise osteoblasts, osteoclasts, osteocytes, or combinations thereof. In some embodiments bone cells are cells of a cell line. In some embodiments a model system comprises a three dimensional (3-D) scaffold, which may be seeded with bone cells or precursors thereof, and may serve as a template for bone formation. In some embodiments the 3-D scaffold may be composed at least in part of calcium or a calcium-containing substance, such as hydroxyapatite. In some embodiments an ex vivo system comprises an explant of bone tissue. In some embodiments a culture system comprises one or more growth or survival factors for one or more bone cell types. In some embodiments a culture system comprises one or more extracellular matrix (ECM) components, such as collagen, proteoglycan, or fibronectin, and/or comprises cells that produce a growth or survival factor or ECM component. In some embodiments such cells comprise fibroblasts.

In some embodiments an agent is administered to a non-human animal that serves as a model for a calcium disorder. Numerous non-human animal models for calcium disorders are known in the art. Non-human animals useful as models include, e.g., non-human mammals such as sheep, dogs, cats, rodents (e.g., rat, mouse, hamster, guinea pig), rabbits, goats, and non-human primates. Examples of animal models for disorders characterized by low bone density, such as osteopenia or osteoporosis include, e.g., female mammals that lack or have dysfunctional ovaries or otherwise lack ovarian function, e.g., ovariectomized mammals. In some embodiments a non-human mammal is subjected to a low calcium diet. In some embodiments a non-human mammal is administered steroids (e.g., glucocorticoids) or other agents that result in reduced bone density or other bone changes characteristic of one or more calcium disorders. In some embodiments a non-human animal is implanted with an isogenic, allogeneic, or xenogeneic bone fragment or bone cells. In some embodiments the bone fragment or bone cells originate from a human. In some embodiments the non-human animal is immunocompromised, such that it does not reject non-isogenic implanted or grafted cells or tissues. In some embodiments the effect of an agent on the implanted bone fragment or bone cells is assessed. The Brtl/+ mouse is a heterozygous model for osteogenesis imperfecta (01) which contains a Gly349Cys substitution in one COL1A1 allele. The oim mouse model (B6C3fe-a/a-colla2$^{oim}$) shows biochemical and phenotypic features of human OI with reduced bone strength, multiple fractures, and skeletal deformities resulting from a spontaneous COL1a2 chain gene mutation, resulting in the absence of normal heterotrimeric collagen COL1(a1)$_2$(a2)$_1$ and replacement by homotrimeric COL1 (a1)$_3$.

Numerous models for bone metastasis and/or osteolytic, osteoblastic, or mixed bone lesions (e.g., caused by tumor metastasis to bone), are known in the art. See, e.g., Rosol, T J, et al., Animal models of bone metastasis. Cancer. 2003; 97(3 Suppl):748-57. In some embodiments an animal model for an osteolytic, osteoblastic, or mixed bone lesion is generated by introducing tumor cells into the animal. In some embodiments tumor cells are introduced into bone, e.g., a long bone such as the tibia or femur. In some embodiments tumor cells are introduced into the vascular system, e.g., intravenously or into the heart. In some embodiments tumor cells are introduced into an orthotopic location (e.g., prostate cancer cells into the prostate gland; breast tumor cells into the breast, etc.) A murine model of induced tumor osteolysis to the distal femur may be generated by introducing cancer cells directly into the femur (Arrington S A, et al., Temporal changes in bone mass and mechanical properties in a murine model of tumor osteolysis. Bone. 2006; 38:359-367). In some embodiments the ability of an agent to inhibit development of or reduce the number or size of osteolytic bone lesions is assessed.

In some embodiments the effect of an agent that binds to or modulates expression, on an indicator of bone cell viability, proliferation, death (e.g., apoptosis), metabolism, or function or at least one indicator of bone turnover, bone formation, or bone resorption is assessed. In some embodiments an indicator comprises induction of osteoclast apoptosis or alteration in osteoblast viability or signaling. In some embodiments an indicator comprises a bone cell-specific activity. In some embodiments an indicator comprises an alteration in a marker of bone turnover that can be detected in blood or a blood fraction such as plasma or serum, or in urine. Examples of such markers include, e.g., alkaline phosphatase, ostase, osteocalcin, or crosslaps. In some embodiments a marker of bone turnover is serum osteocalcin, bone specific alkaline phosphatase, the N-terminal propeptide of type I collagen for bone formation, and/or the crosslinked C-(CTX) and N-(NTX) telopeptides of type I collagen for bone resorption. In some embodiments, an agent that has an effect indicative of potential therapeutic efficacy in treating a calcium disorder is identified. In some embodiments the effect of an agent in a test system is compared with that of a NBP that is approved by the FDA (or a similar government agency responsible for regulating medical products) for administration to human subjects for treating a calcium disorder. In some embodiments, the agent may be identified as a candidate agent useful for treating one or more calcium disorders if the agent has an effect that is similar to that of the approved NBP.

In some embodiments, the effect of an agent identified as described herein may be compared with the effect of a bisphosphonate, e.g., a NBP, in a similar system. In some embodiments an agent that has a greater effect on an indicator of NBP efficacy than that produced by an NBP may be identified. In some embodiments an agent that has a lesser effect on an indicator of NBP toxicity than that produced by an NBP may be identified.

Agents identified using methods described herein may, in some embodiments, be useful for diagnosing and/or treating a subject, e.g., a subject suspected of having or having a calcium disorder calcium disorder. In some embodiments an agent described or identified as described herein is used to treat a subject in need of treatment of a calcium disorder.

An agent or composition may be administered using any suitable route such as, but not limited to, intravenous, intraarterial, oral, intranasal, subcutaneous, intramuscular, intraosseus, intrasternal, intraperitoneal, intrathecal, intratracheal, intraocular, sublingual, vaginal, rectal, dermal, or pulmonary administration.

Treating Calcium Disorders

The present invention provides agents for treating a subject suffering from a calcium disorder. In some embodiments, the agent may comprise a therapeutic agent as described herein (or a prodrug, pharmaceutically acceptable salt or other pharmaceutically acceptable derivative thereof), and optionally comprise a pharmaceutically acceptable carrier. In some embodiments, therapeutic agents as described herein, further comprise one or more additional therapeutic agents. Alternatively, therapeutic agent of this invention may be administered to a patient in need thereof in combination with the administration of one or more other therapeutic agents. For example, additional therapeutic agents for conjoint administration or inclusion in a pharmaceutical composition with an agent of this invention may be an approved anti-inflammatory agent, chemotherapeutic agent, opiate, non-steroidal anti-inflammatory drug, steroid, calcium supplement, or it may be any one of a number of agents undergoing approval in the Food and Drug Administration that ultimately obtain approval for the treatment of any calcium disorder.

Monitoring Calcium Disorder Therapy

The present invention, among other things, provides systems for identifying and/or characterizing agents useful in monitoring the treatment of calcium disorders and/or calcium disorder therapy. In some embodiments, systems may be used to evaluate the effectiveness of a treatment therapy, drug regimen, responsiveness to therapy, prognosis for a disease state, drug toxicity and measurement of disease progression in a subject. Typically, in such systems, level and/or activity of a gene or gene product may be determined from a sample obtained from the subject, from one or more time points, which are compared to the levels from the subject from one or more other time points. For example, gene or gene product expression levels may be measured before or at the beginning of a treatment course. Gene or gene product levels may be measured at one or more time points throughout the course of treatment and compared with the level before the treatment or from an earlier time point of a treatment course. Identification or selection of appropriate treatment, determining if a patient has positive response to a treatment and/or optimization of the treatment can be guided using the information obtained by these systems.

For example, using systems described herein, skilled physicians may select and prescribe treatments adapted to each subject based on the diagnosis and disease staging provided to the subject through determination of the level, form, and/or activity of one or more biomarkers described herein. In some embodiments, an appropriate therapeutic regimen for a given patient may be made based solely on the diagnosis/staging provided by the systems described herein. In some embodiment, a physician may also consider other clinical or pathological parameters used in existing methods to treat a calcium disorder and assess its advancement.

In some embodiments, systems described herein may be used for monitoring treatment response in a patient suffering from a calcium disorder. Typically, for example, the levels of one or more biomarkers in a patient are measured after receiving treatment for a calcium disorder. The level, form, and/or activity of one or more biomarkers are then compared to a control level to determine if the subject has had a positive response to the treatment. As used herein, a "positive response" to a treatment includes reduced severity of disease symptoms, slowed progression, abatement or cure of a calcium disorder. In some embodiments, control level may be the level of the one or more biomarkers obtained from the same patient before receiving the treatment or measured at an earlier time point of the treatment. In some embodiments, a suitable control level is the level of the one or more biomarkers in a control patient without the treatment. In some embodiments, such a control level may be determined from a significant number of control patients, and an average or mean is obtained. Typically, a control patient is at a comparable disease or developmental stage. Typically, a diminished or elevated level, form, and/or activity with statistical significance of the one or more biomarkers as compared to a suitable control level indicates that the subject has positive response to the treatment. Various statistical methods and techniques such as those described herein may be used to determine statistical significance. In some embodiments, a biomarker has a diminished level if the level, form, and/or activity of the biomarker measured in a sample obtained at a relevant time point of interest is reduced by more than 10%, 20%, 30%, 40%, 50%, 60%, 70%, 80%, 90%, 95% as compared to a control level. In some embodiments, a biomarker has an elevated level if the level, form, and/or activity of the biomarker measured in the samples is more than 20%, 30%, 40%, 50%, 60%, 70%, 80%, 90%, 1-fold, 1.2-fold, 1.5-fold, 1.75-fold, 2-fold, 2.25-fold, 2.5-fold, 2.75-fold, or 3-fold higher as compared to a control level.

As used herein, the term "therapeutically effective amount" generally refers to an amount that is sufficient to achieve a meaningful benefit to the patient suffering from the calcium disorder, such as an amount sufficient to increase bone mass, achieve normal calcium levels in the body, maintain calcium homeostasis, increase calcium uptake within the body, reduce the number/type/severity of fractures, increase/decrease osteoblast and/or osteoclast function, e.g., by stimulating or inhibiting osteoblast or osteoclast differentiation or apoptosis. In some embodiments, biomarker level, form, and/or activity may be used as a factor for determining a suitable therapeutically effective amount. In some embodiments, biomarker level, form, and/or activity may be used in combination with other characteristics of the subject. Such characteristics include the condition, disease severity, general health, age, sex and body weight of the subject. In some embodiment, biomarker level, form, and/or activity may be used as a factor for determining administration route and/or intervals. In some embodiments, biomarker level, form, and/or activity may be used in combination with other factors such as the nature, severity of the disease and extent of the subject's condition. For example, a physician may recommend therapeutic agents be administered periodically at regular intervals (e.g., once every year, once every six months, once every five months, once every three months, bimonthly (once every two months), monthly (once every month), biweekly (once every two weeks), weekly) depending on biomarker level, form, and/or activity measured according to the present invention, with or without considering other factors such as the nature, severity of the disease and extent of the subject's condition.

The invention will be more fully understood by reference to the following examples. They should not, however, be construed as limiting the scope of the invention. All literature citations are incorporated by reference.

EXAMPLES

Example 1

Identification of Genes Involved in Nitrogenous Bisphosphonate Resistance

Rationale

As access to medical care has improved people are living longer. Yet, aging-associated diseases still present a barrier to increases in life expectancy as well as improvements in quality of life. Osteoporosis is the most common aging-associated bone condition. Despite its importance to human health, there remain few approved treatments for osteoporosis. Nitrogenous Bisphosphonates (NBPs) are the major treatment and have been utilized to prevent bone loss and pathological calcifications (Fleisch et. al., 1969, Science, 165:1262-1264; Fleisch et. al., 1969, Science, 165:1264-1266; both of which are hereby incorporated by reference.) long before it was feasible to interrogate their molecular target(s). As NBPs became more frequently used in the clinic, considerable effort was made to understand the molecular basis for their action on bone. Currently, it is believed that inhibition of cholesterol synthesis in osteoclasts, and in particular inhibition of the activities of farnesyl diphosphate synthase (FDPS) and geranyl geranyl phosphate synthase (GGPS) is key to the anti-osteoporotic effects of NBPs (Fisher et. al., 1999, *Proc Natl Acad Sci USA*, 96:133-138; Van Beek, 1999, *Journal of bone and mineral research: the official journal of the American Society for Bone and Mineral Research*, 14:722-729; both of which are hereby incorporated by reference). The work of many groups has established that NBPs inhibit FDPS and GGPS activity by binding to the active sites of these enzymes (Hosfield et. al., 1999, *The Journal of Biological Chemistry*, 279:8526-8529; Kavanagh et. al, 2006, *Proc Natl Acad Sci USA*, 103:7829-7834; both of which are hereby incorporated by reference). However, few studies have addressed the mechanism by which NBPs are taken up by cells or what the native function(s) of a putative NBP receptor might be. Additionally, it is not yet established that the therapeutic properties of NBPs are due to NBP entry into cells and subsequent inhibition of FDPS or GGPS activities. As orally or intravenously delivered NBPs target and adhere strongly to the bone surface (Masarachia, et. al., 1996, *Bone*, 19:281-290; Sato et. al., 1991, *The Journal of Clinical Investigation*, 88:2095-2105; both of which are hereby incorporated by reference), it is possible that the disease-relevant site of NBPs action might instead be extracellular or at the cell surface of bone cells. In addition to improving bone function, NBPs have also been shown to decrease cancer risk (Mundy et. al., 2002, *Nature Reviews. Cancer*, 2:2095-2105; hereby incorporated by reference).

However, there are also significant risks associated with NBP treatment. It is increasingly appreciated that NBP treatment can lead to osteonecrosis of the jaw as well as Barrett's esophagus (Kuehn et. al., 2009, *JAMA*, 301:710-711; hereby incorporated by reference). Therefore, developing better therapies to treat osteoporosis that have fewer side effects is of pressing need and clear value.

Genetic Screen

The current invention, set out to identify and characterize genes and cellular pathways regulated by the NBPs. In addition to the putative NBP targets, FDPS and GGPS, it is not known what other genes might control the responsiveness of bone cells to NBP treatment or lead to NBP resistance or sensitivity. A genetic screen was developed, using a recently characterized human haploid cell line. (Carette et. al., 2009, *Science*, 326:1231-1235, hereby incorporated by reference), to identify novel genes relevant in playing a role in the NBP drug pathway, and identify a possible mechanism of action for the drug.

Identifying the molecular mechanisms for many drugs of interest has long been a fruitful territory of genetic research in model organisms such as the budding yeast, *Saccharomyces cerevisiae*. A particularly well-known example was the identification in *S. cerevisiae* of the target of the immunosuppressant, rapamycin (Heitman, et. al., 1991, *Science*, 253:905-909; hereby incorporated by reference). While rapamycin was later found to act on proteins that are also present in mammalian cells (Sabatinin, et. al., 1994, *Cell*, 78:35-43; Brown et. al., 1994, *Nature*, 369:756-758; both of which are hereby incorporated by reference), other clinically used drugs have not been found to exhibit similar effects in model organisms as in humans (Bivi et. al., 2009, *Genome Biol*, 10:R93, hereby incorporated by reference) and thus, genes whose products are targeted by them have eluded identification. The discovery of RNA interference (RNAi)-based gene inactivation (Fire et. al, 1998, *Nature*, 391:806-811, hereby incorporated by reference) opened up the possibility of performing drug resistance screens in human cells. Unfortunately, discoveries of gene targets using RNAi screens have been hampered by several limitations such as: (1) anecdotal observations of RNAi-generated hypomorphic alleles where the levels of gene inactivation do not correlate well with the phenotypes of interest and where the phenotypes are not reproducibly penetrant between experiments; and (2) published findings of many RNAi reagents reducing the protein expression of numerous "off-target" gene products in addition to the intended gene products (Ma et. al., 2006, *Nature*, 443:359-363; Echeverri et. al., 2006, *Nat Rev Genet*, 7:373-384; both of which are hereby incorporated by reference). While the reasons for these behaviors are not entirely understood, in high-throughput RNAi screens larger than expected numbers of gene knock-downs produce a phenotype exceeding a desired threshold, and in independently performed experiments, there can be significant discordance between well-scoring genes (Bushman et. al., 2009, *PLoS Pathog*, 5:e1000437; hereby incorporated by reference).

The system of the current invention is designed to circumvent these limitations through the use of a predominantly haploid cell line, KBM7. While a single cell type is called out for the current example, one skilled in the art would appreciate that any haploid cell line could be used for the invention. A haploid genome allows one to overcome both of the aforementioned issues with RNAi: (1) one can generate true null alleles using insertional mutagenesis where the integration of gene-trap containing DNA sequence is tagged to identify the disrupted gene; and (2) where increased target gene specificity is conferred by gene-trap retroviruses that contain a strong adenoviral splice acceptor site and tracking gene and that can be easily titered to one integration per cell. While the current invention uses the KBM7 haploid cell line, one skilled in the art would appreciate that any haploid cell line can be used. In addition, the current invention also encompasses the use of a haploid cell line, which is generated from a diploid organism and is rendered haploid using any of the molecular biology techniques known in the art.

Identification of Nitrogenous Bisphosphonate Resistance Biomarkers

Figure 3:
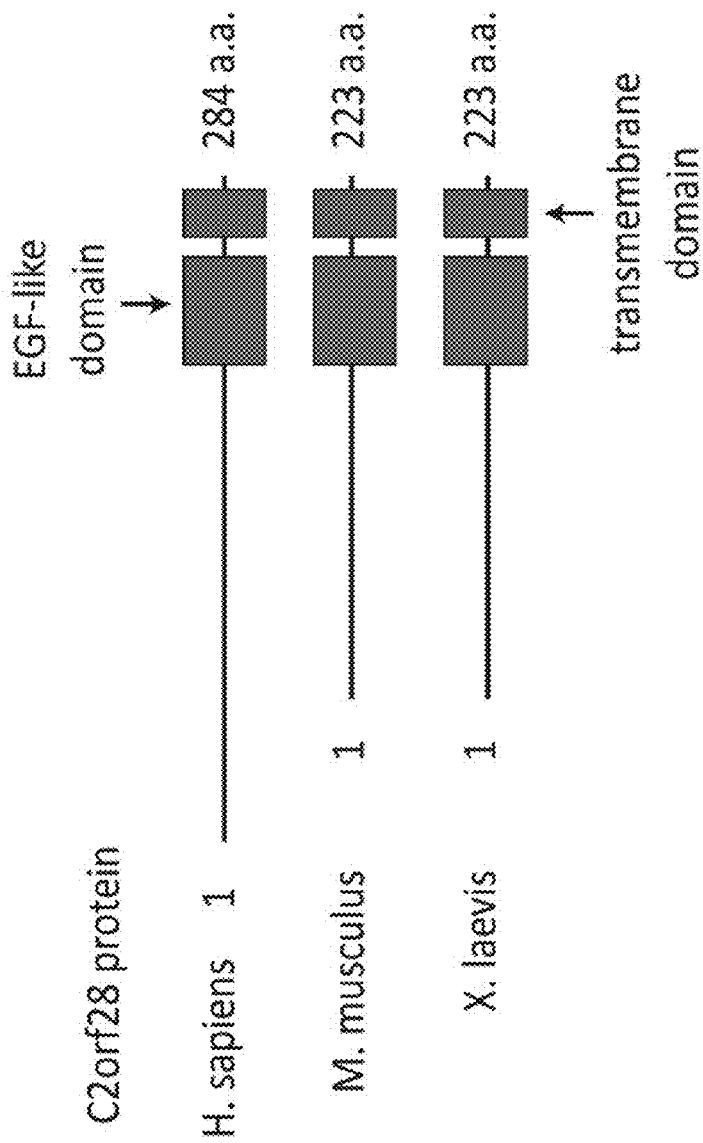
FIG. 3. C2orf28 Protein Structure. Schematic representation of certain structural features of human C2orf28 and its mouse and frog orthologues.

The aim of the current experiment was to identify gene targets for nitrogenous bisphosphonates, a general class of compounds used to treat a calcium disorder. NBPs have shown to be effective in treating calcium disorders through their anti-osteoclast and pro-osteoblast effects on cells, but their molecular targets remain poorly described. To develop the screen, a pooled genome-scale deletion library was generated, using the haploid KBM7 cell line described above. The knockout cells were created using a retroviral based gene-trap with a strong adenoviral splice acceptor site and tracking gene. Infection was carried out using serial dilutions to titer the virus and ensure one integration per cell, resulting in cell each containing null allele genotype for only a single gene. The mutagenized KBM7 cell library was then grown for four weeks in IMDM with 10% IFS, containing Alendronate at a final concentration of 65 µM. Only those knockout cells able to survive the cytotoxic effects of Alendronate were able to grow in the media. For those cells viable, post the four week incubation, genomic DNA was extracted and sequences to identify the tracking sequence and determine the gene integration site (FIG. 1 and FIG. 3).

Figure 2:
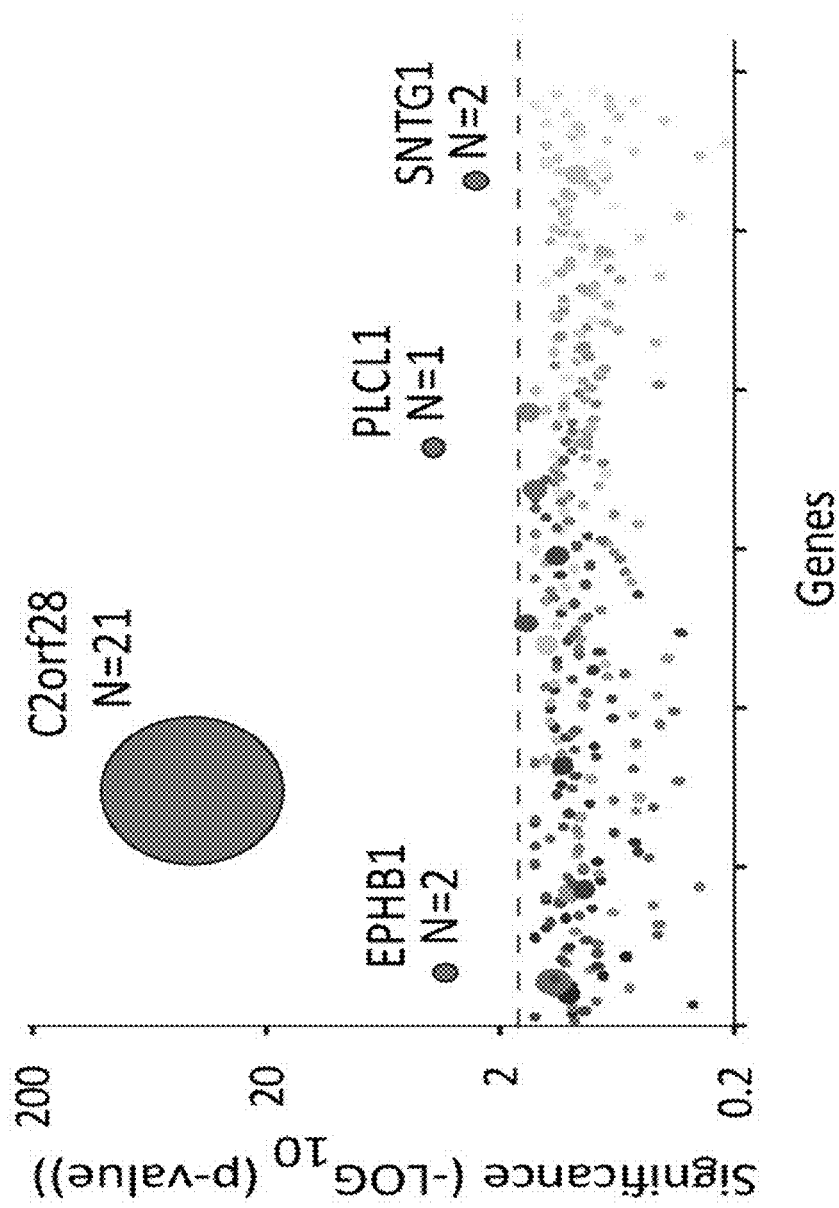
FIG. 2. Identification of Gene Targets. Sequencing-based identification of gene-trap insertion sites in Alendronate-resistant cells. N=Number of unique insertions within the stated gene locus. P-values for samples: C2orf28=2.79×10-45, PLCL1=6.38×10-07, EPHB1=1.91×10-06, SNTG1=2.29×10-05.

Using the NBP cell viability-based read-out of the current invention, the inventors identified C2orf28 as the gene most commonly mutated in cells resistant to the cytotoxic effects of Alendronate. In addition to C2orf28, mutations in three other genes, EPHB1, PLCL1 and SNTG1, were also show to confer NBP resistance (FIG. 2). While a single NBP was used for the experiment, one skilled in the art would recognize the any NBP could be used with the current invention. In addition, one skilled in the art would appreciate that the current invention encompasses a general screening approach that is not limited in scope to NBPs, but could be used to identify genes involved cellular pathways for other cytotoxic compounds.

Example 2

Characterizing the Role of C2orf28 in Nitrogenous Bisphosphonate Resistance

C2orf28 Function on NBP Cytotoxicity

Due to its recent identification, little is known about Apoptosis Related Protein 3 (ARP3), which was mapped to open reading frame 28 on *H. sapiens* chromosome two, resulting in the alternative nomenclature used by NCB1, C2orf28. The *M. musculus* homolog of APR3 is known by the NCBI symbol 0610007C21R1k. The gene products C2orf28 was originally identified from HL-60 cells as a transcript whose expression was increased by all-trans-retinoic acid which is known to induce cell differentiation and apoptosis in the cancer cell type, acute promyleocytic leukemia, (APL) of which the HL-60 cell line was derived (Zhu et al., 2000, *BioTechniques*, 29:310-313; hereby incorporated by reference). Although there have only been a few research studies on C2orf28 function, it has been reported that its overexpression causes G1/S phase arrest, which may result from APR3's ability to reduce Cyclin D1 expression (Yu et. al., *Biochem. Biophys. Res. Commun.*, 358:1041-1046; hereby incorporated by reference). Studies have also shown that C2orf28 contains regions in its promoter that are responsive to the transcription factors, NF-kappa B and NFAT, supporting its role in cellular proliferation. (Yang et. al., 2007, *Molecular and cellular biochemistry*, 302:187-194; hereby incorporated by reference).

Figure 4:
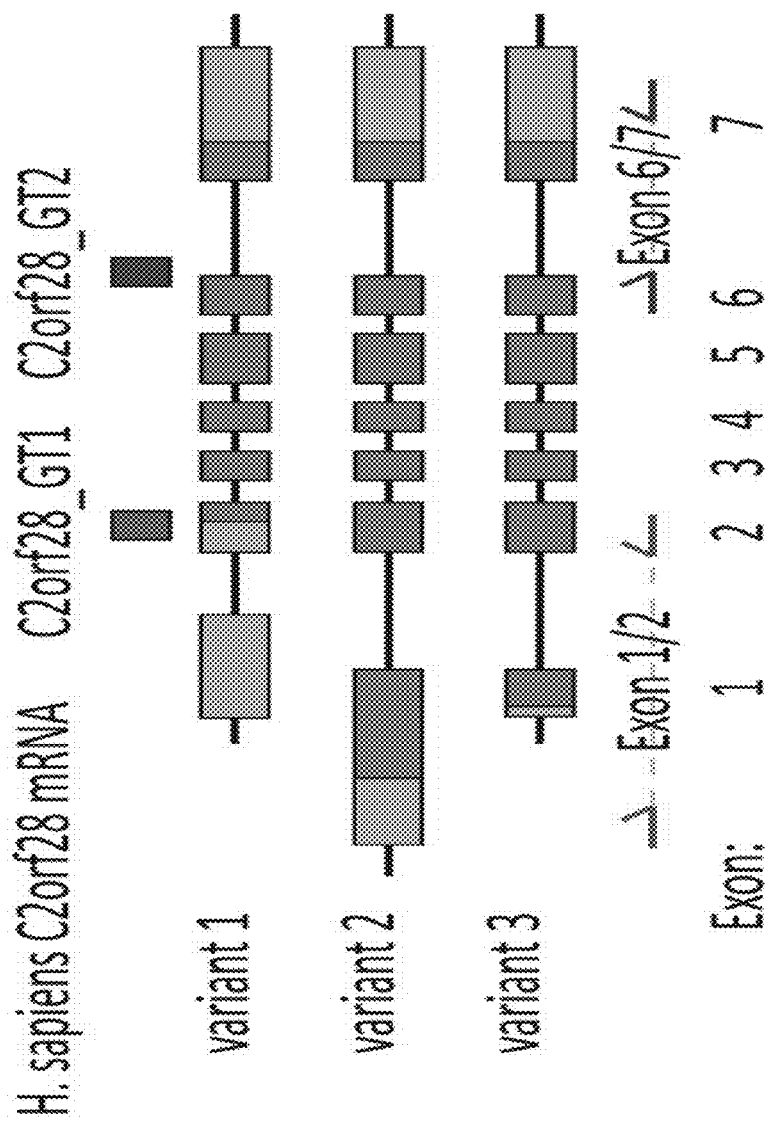
FIG. 4. Exon Structure of C2orf28 mRNA Variants. Schematic representation of the exon structure of three human C2orf28 mRNA variants. Shown are coding sequences for each variant (dark) and non-coding portions of each exon (light). Translated regions of variant 1 and variant 3 are shorter than variant 2 due to internal translation initiation sites. Locations of primer sets used to identify each C2orf28 gene trap (GT) are listed as (C2orf28 GT1) and (C2orf28_GT2).
Figure 5:
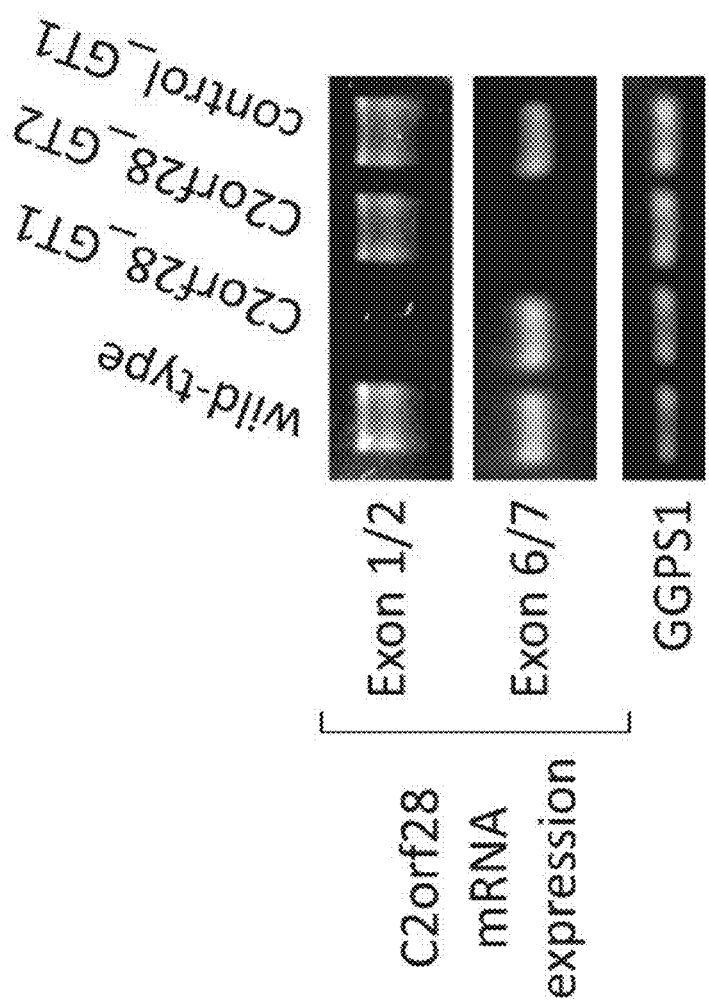
FIG. 5. mRNA Analysis. mRNA analysis of C2orf28 and geranyl geranyl phosphate synthase (GGPS1) expression levels in clones that contain independent gene-trap insertions in their respective loci. Wild-type KBM7 cells were compared with mutant alleles (labeled as GT) and GGPS1 was used as a loading control.

Structurally, C2orf28 is potentially a transmembrane protein. It is predicted to contain a signal sequence at the N-terminus, followed by an EGF-like domain, a transmembrane region and an intracellular region at the C-terminus (FIG. 3). (Yang et. al., 2007, *Molecular and cellular biochemistry*, 302:187-194; and Mulder et. al., *Nucleic Acids Res.*, 2007, 35:D224-D228; both of which are hereby incorporated by dereference) In addition, the gene encoding C2orf28 contains two promoters and alternative splice sites, resulting in three known isoforms (FIG. 4). Variant two has been shown to localize on the cell surface of MCF-7 (human breast cancer) cells (Yang et. al., 2007, *Molecular and cellular biochemistry*, 302:187-194; hereby incorporated by reference), while variant three is reported to be a putative secreted protein. (Clark et. al., *Genome Research*, 2003, 13:2265-2270, hereby incorporated by reference)

Figure 6:
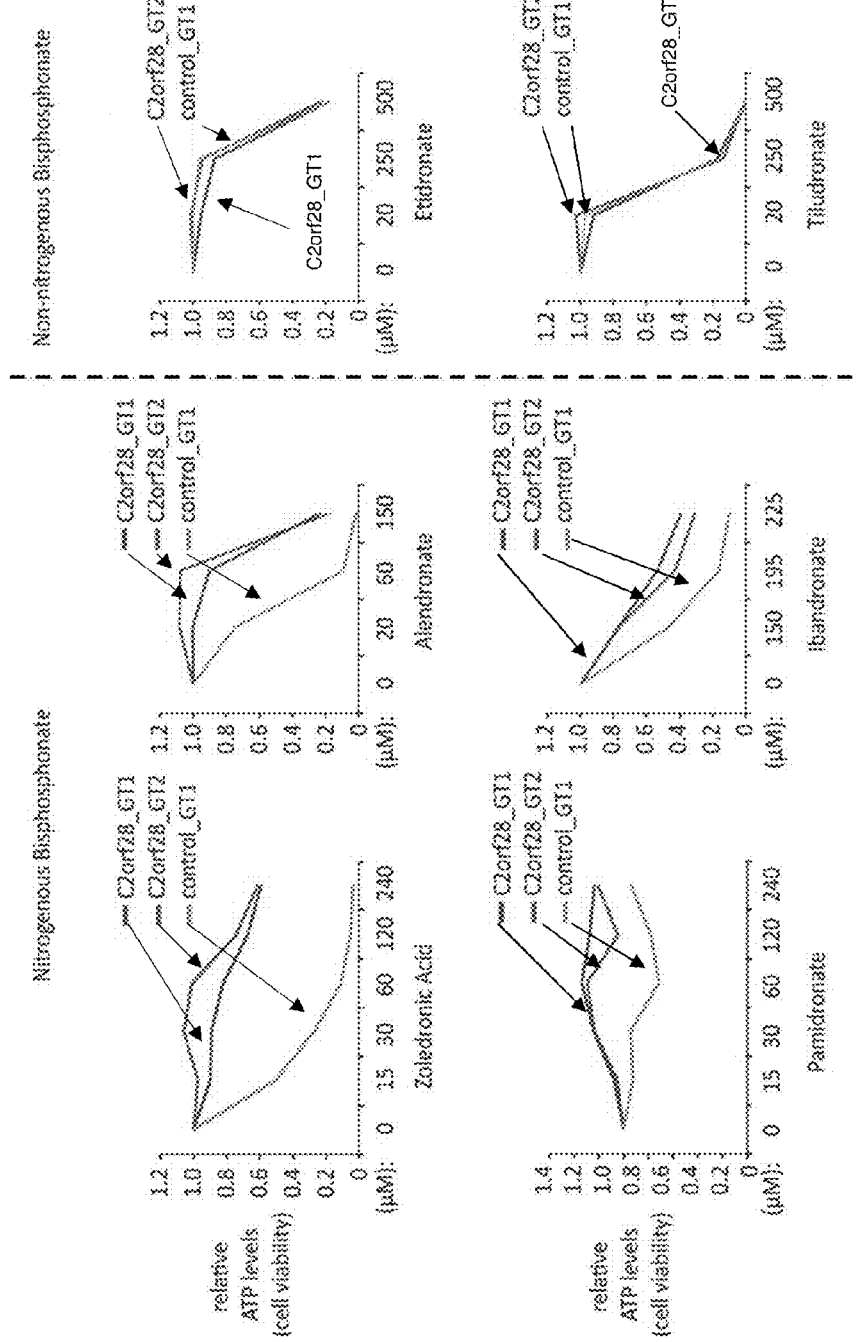
FIG. 6. Cell Viability. Cell viability in control and C2orf28 deficient cells upon nitrogenous bisphosphonate (NBP) or non-nitrogenous bisphosphonate (BP) treatment. All cells were treated with the indicated concentration of the indicated NBP (Alendronate, Ibandronate, Pamidronate, Zoledronic Acid) or BP (Etidronate, Tiludronate). Cell viability was determined after 72 hours, by measuring cellular ATP levels and is expressed as a ratio of the compared with untreated cells.

Given the initial findings with Alendronate, the inventors set out to examine the effect of several different bisphosphonate compounds on C2orf28 deficient cells. Control KBM7 cells and those mutagenized to perturb C2orf28 function (C2orf28_GT1, C2orf28_GT2) were grown for 72 hours in cell media treated with either, a non-nitrogenous bisphosphonate (BP) or nitrogenous bisphosphonate (NBP), at the indicated concentration (FIG. 6). The compounds selected for the experiment were as follows: NBPs (Alendronate, Ibandronate, Pamidronate, Zoledronic Acid) or BPs (Etidronate, Tiludronate). After 72 hours cell viability was determined by measuring cellular ATP levels and was expressed as a ratio of that compared with untreated cells (FIG. 6). All measurements were performed in quadruplicate. To test the generalizability of these findings, the inventors determined whether the lack of NBP responsiveness of C2orf28 deficient cells also occurs in a cell and mutation context distinct from that used in our primary screen. In HEK-293T, similar to the inventors results using KBM7 cells with gene trap-mediated mutagenesis of the C2orf28 gene, C2orf28 depletion using RNAi conferred strong resistance to the anti-proliferative effects of Alendronate (data not shown).

Figure 7:
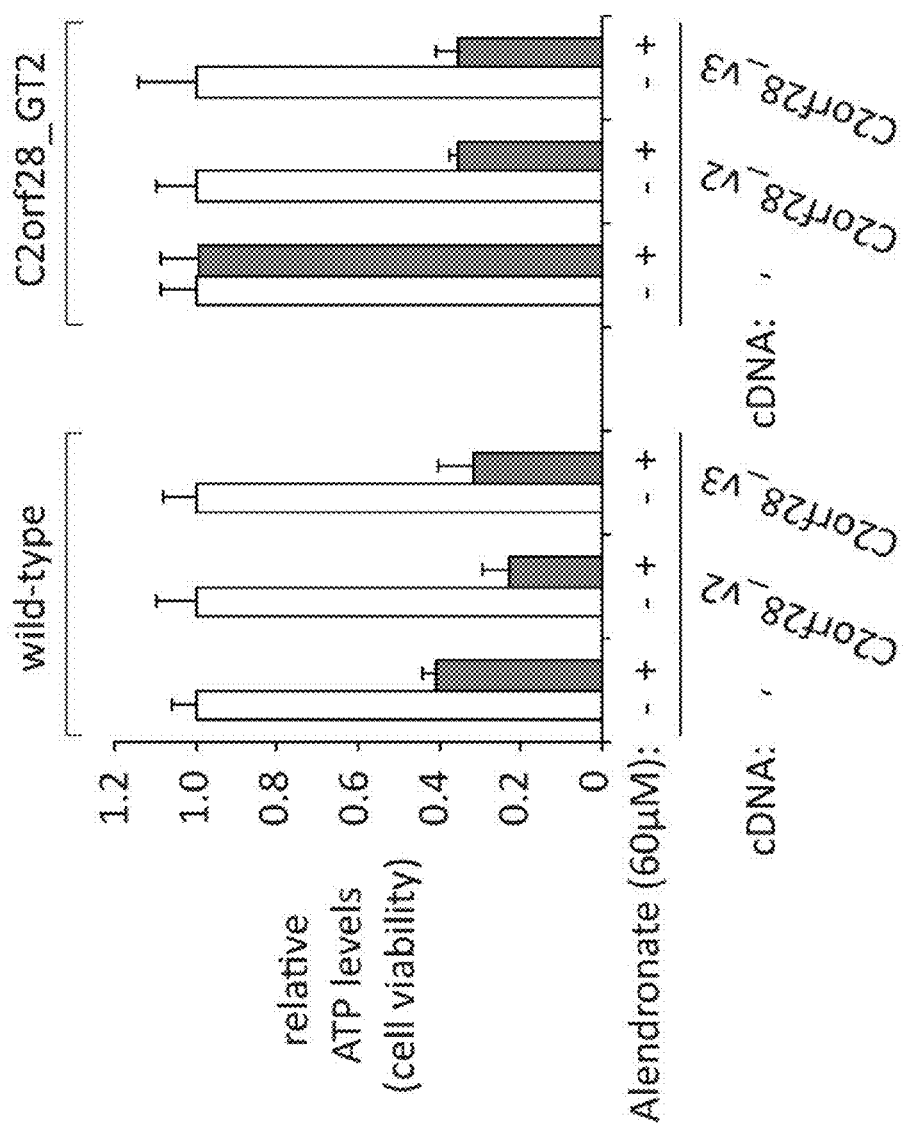
FIG. 7. Cell viability Vs. Rescue. Cell viability in control and C2orf28-deficient cells with or without exogenously expressed C2orf28 cDNA. Cells were treated with 60 µM Alendronate. Cell viability was determined after 72 hours, by measuring cellular ATP levels, which are expressed as a ratio of the treated with untreated cells. V2=variant 2 of C2orf28; V3=variant 2 of C2orf28.

The inventors next set out to determine if exogenous expression of a functional C2orf28 variant protein was sufficient to rescue the NBP sensitivity originally observed in the wild-type KBM7 control cells. The original KBM7 C2orf28 mutant cells (C2orf28_GT1, C2orf28_GT2) from the initial screen, were transfected to overexpress exogenous cDNA for either C2orf28 variant 2 or variant 3. Control and C2orf28 rescue cells (C2orf28_V2, C2orf28_V3) were grown for 72 hours in cell media treated with 60 μM Alendronate. After 72 hours cell viability was determined by measuring cellular ATP levels and was expressed as a ratio of that compared with untreated cells (FIG. 7). All measurements were performed in quadruplicate. The data suggests, that in contrast to cells lacking C2orf28 expression, exogenous expression of either C2orf28 variant 2 or variant 3 in C2orf28 mutant cells, rendered them as sensitive to Alendronate as wild-type KBM7 cells.

C2orf28 in regulating NBP Cytotoxicity

Current research suggests that the therapeutic benefit of NBPs may be primarily through their inhibition of FDPS and GGPS enzyme activities in osteoclasts, which leads to defective protein prenylation and subsequent impairment of the osteoclast to establish proper cell adhesion and vesicle trafficking required for bone resorption (Fisher et. al., *Proc Natl Acad Sci USA*, 1999, 96:133-138; Van beek et. al., *Journal of bone and mineral research: the official journal of the American Society for Bone and Mineral Research*, 1999, 14:722-729; Itzstein et. al., *Small GTPases* 2, 2011, 117-130, all of which are hereby incorporated by reference) Both in vitro and in cells, NBPs have been shown to inhibit the activities of FDPS and GGPS through interaction with their respective active sites. (Hosfield et. al., *The Journal of biological chemistry*, 2004, 279: 8526-8529; Kavanagh et. al., *Proceedings of the National Academy of Sciences of the United States of America*, 2006, 103:7829-7834; both of which are hereby incorporated by reference)

Figure 8:
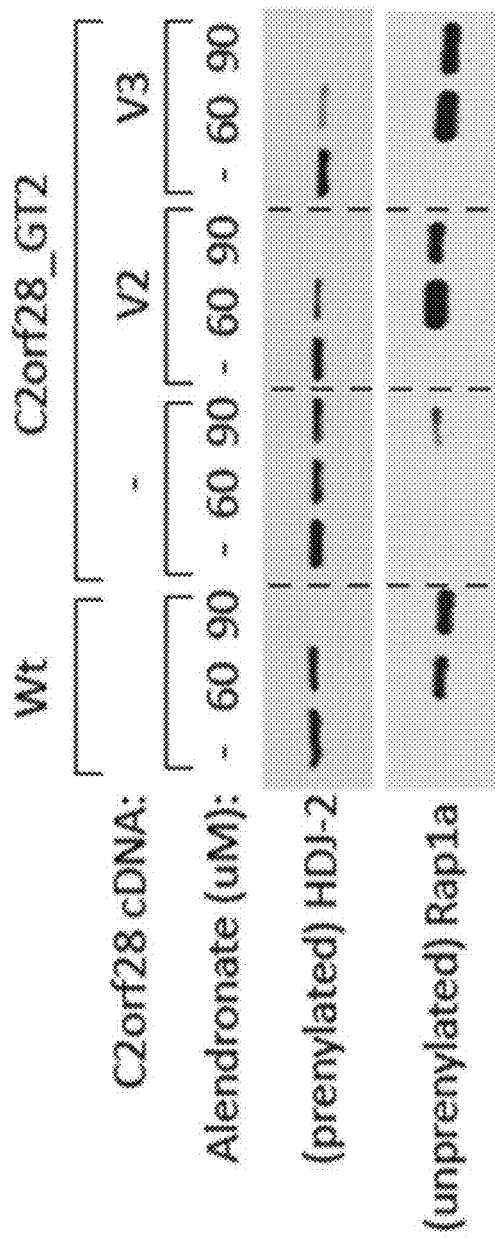
FIG. 8. Effect of Nitrogenous Bisphosphonates on Prenylation. Cells containing (WT) or lacking C2orf28 (C2orf28_GT2) were treated with Alendronate at the indicated dose ((−) indicates no Alendronate). After 72 hours the cells were analyzed by immunoblotting for the indicated proteins.

Therefore, to determine whether C2orf28 is involved with NBPs mediated protein prenylation, the inventors' monitored the prenylation of several known prenylated proteins including the heat shock protein DnaJ (Hsp40) homolog, HDJ-2, and the Ras family GTPase, Rapla. Cells containing or lacking C2orf28 were treated with the indicated dose of Alendronate for 72 hours then lysed and analyzed by immunoblotting for the indicated proteins. It was determined that, Alendronate impaired both HDJ-2 and Rapla prenylation in a dose dependent manner (FIG. 8). On the contrary, Alendronate had no effect on the level of HDJ-2 and Rapla prenylation in C2orf28 deficient cells (FIG. 8). This suggests that C2orf28 may control protein prenylation at a step upstream of the effect of NBPs on FDPS or GGPS.

Figure 9:
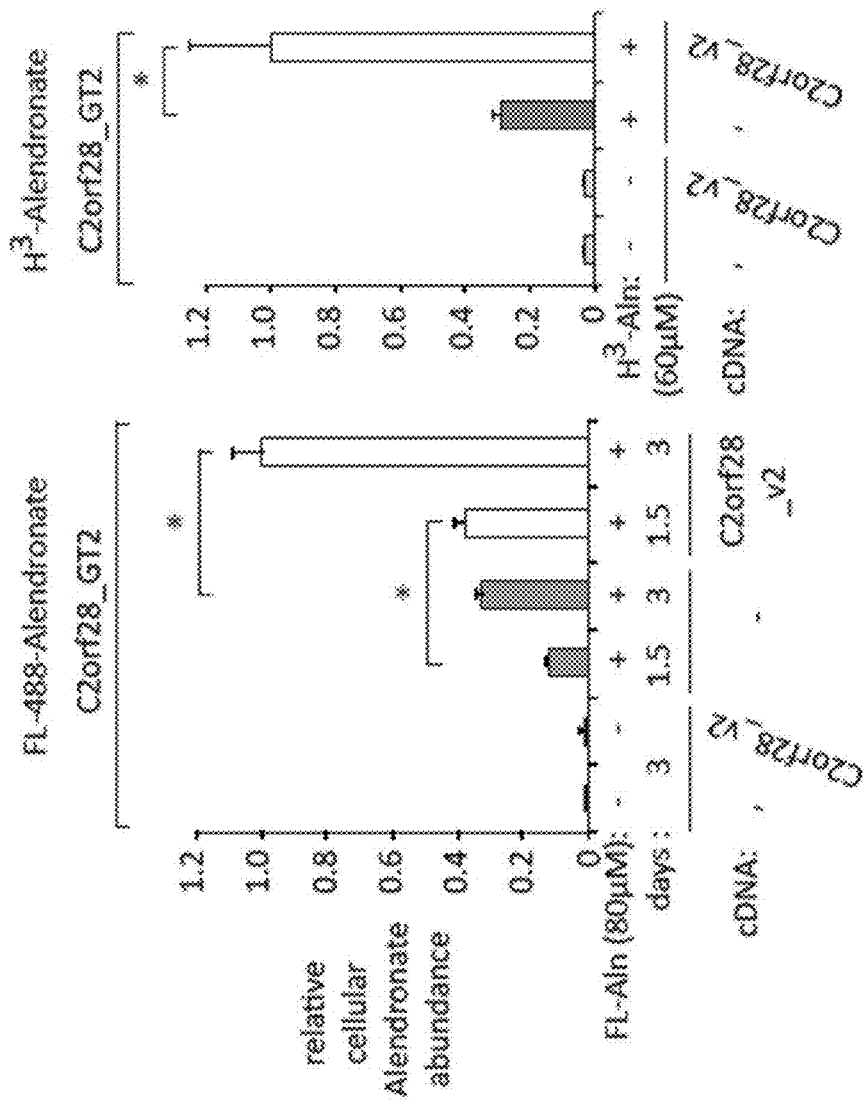
FIG. 9. Cellular accumulation of Alendronate. Cells deficient in C2orf28 (C2orf28_GT2) were incubated with or without (−) fluorescently conjugated Alendronate (75 µM) for 60 hours. Cells were then analyzed for cellular uptake of compound using fluorescence spectroscopy.

Given that C2orf28 is suspected of being a putative plasma membrane protein, it was hypothesized that C2orf28 might play a role in regulating NBP cellular uptake. To test this, the inventors' monitored the uptake of labeled Alendronate in cells containing or lacking C2orf28. Control and C2orf28 deficient cells were treated with 75 μM of fluorophore conjugated $H^3$-labeled Alendronate plus 60 μM cold alendronte for 60 hours. Following incubation, the cells where rinsed and lysed and the abundance of Alendronate in the cell lysates was quantified by fluorescence spectroscopy or scintillation counter. In comparison with C2orf28-complemented cells, C2orf28 deficient cells demonstrated an altered cellular Alendronate accumulation (FIG. 9). This suggests that Alendronate intracellular accumulation may be facilitated by directly binding C2orf28.

Figure 10:
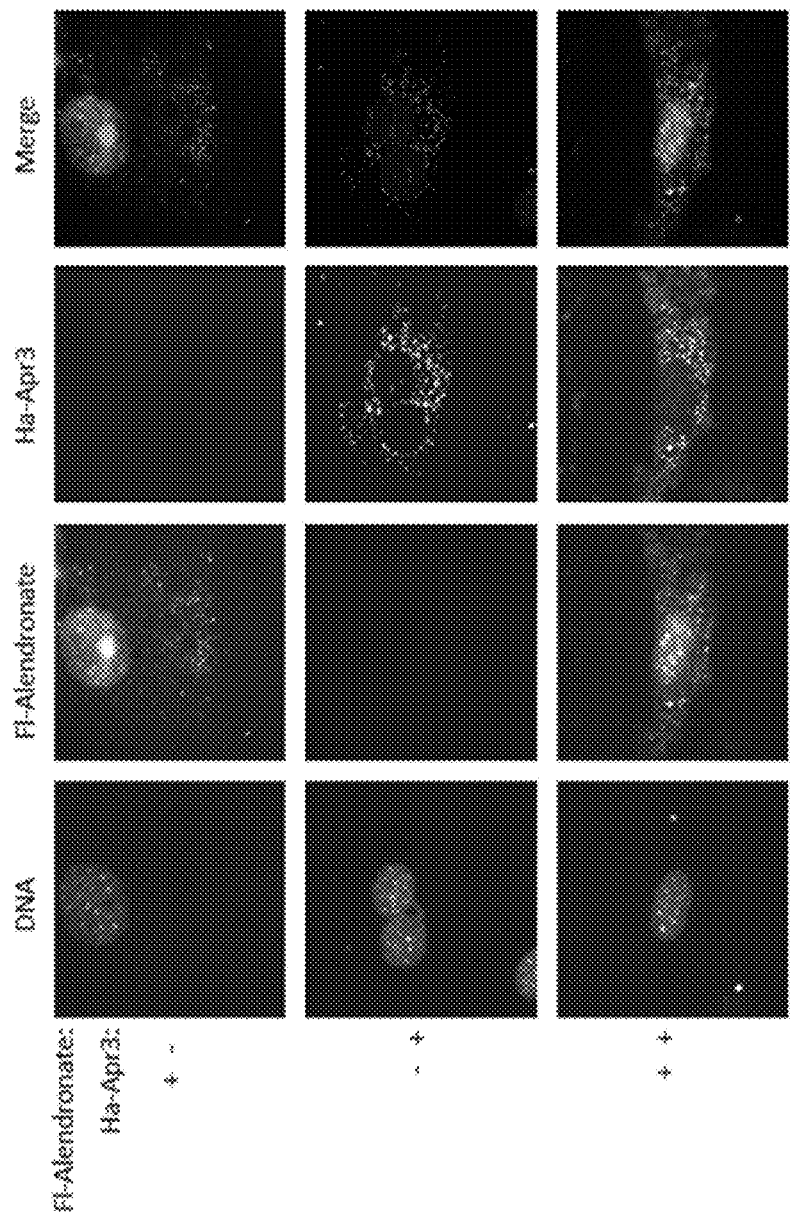
FIG. 10. Sub-cellular Localization. MC3T3-E1 pre-osteoblasts stably expressing HA tagged C2orf28 variant 2 were treated with fluorescently conjugated Alendronate (75 µM). Cells were processed in an immunofluorescence assay.

Cellular localization of Alendronate and C2orf28 was examined by observing their individual immunostaining profiles in MC3T3-E1 pre-osteoblasts. MC3T3-E1 pre-osteoblast cells stably expressing and HA tagged version of C2orf28 variant 2 were treated with 7504 fluorophore conjugated Alendronate. Following incubation, the cells were washed, and processed in an immunofluorescence assay to detect HA and Alendronate, along with DAPI to visualize DNA content. C2orf28 staining was punctate and often appeared as in vesicles throughout the cell consistent with that previously reported for Alendronate and as we observed (FIG. 10). Alendronate and C2orf28 co-staining also displayed a high degree of colocalization consistent with the hypothesis that C2orf28 binding to alendrondate might be important for alendrodronate, of NBP in general, accumulation in cells (FIG. 10).

C2Orf28 Membrane Targeting in Regulating NBP Cytotoxicity

Figure 11:
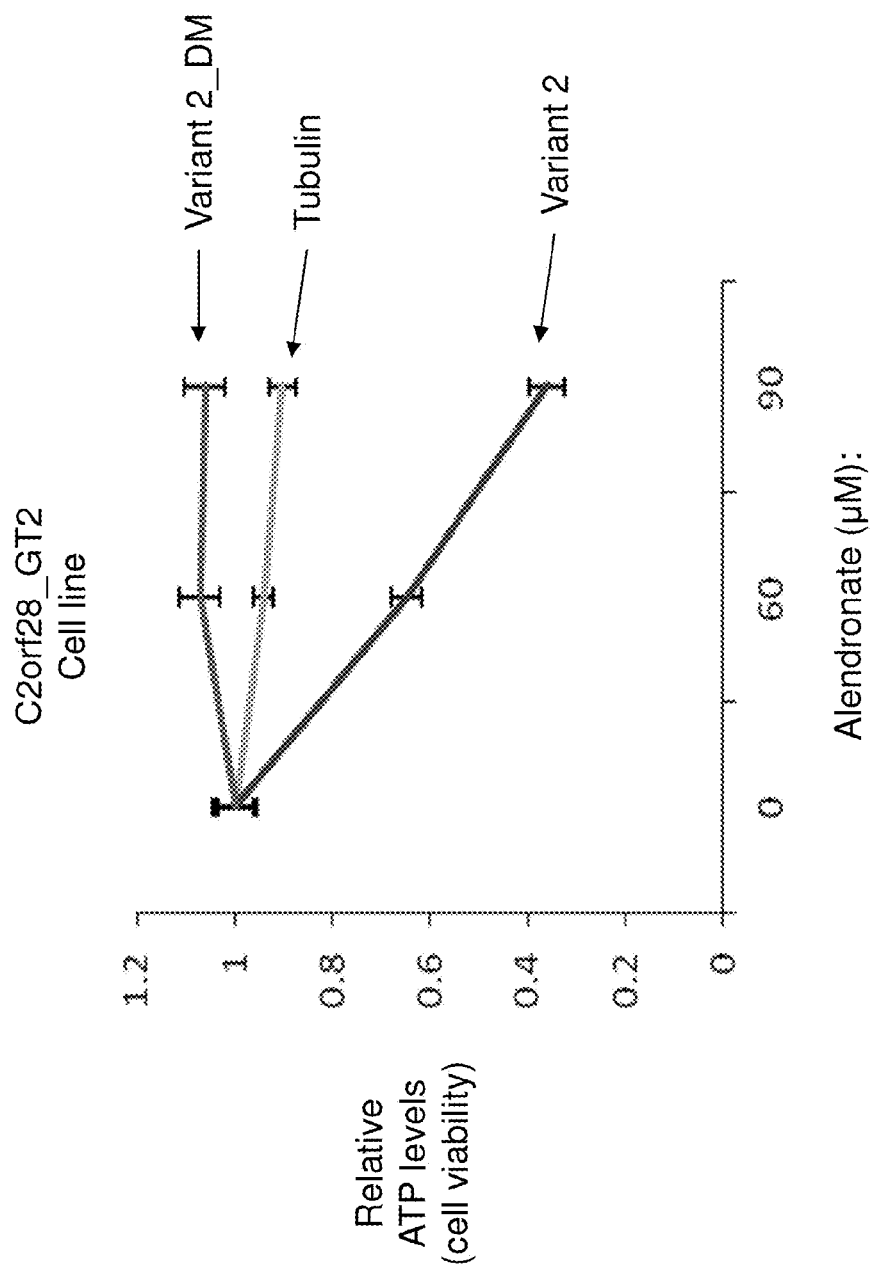
FIG. 11. C2orf28 Membrane Targeting. Cells deficient in C2orf28 (C2orf28_GT2) were transformed express exogenous tubulin (Tubulin), C2orf28 variant 2 (Variant 2), or C2orf28 variant 2 lacking the transmembrane domain (C2orf28 variant 2_DM). Cells were treated with Alendronate at the indicated dose. Cell viability was determined after 72 hours, by measuring cellular ATP levels and is expressed as a ratio of the compared with untreated cells.

To further investigate the possible role of C2orf28 in facilitating NBP entry into the cell, additional experiments were conducted to look at the role of C2orf28 membrane translocation. C2orf28 knockout cells (C2orf28 GT2) from the initial screen were transfected to exogenously express Tubulin, C2orf28 variant 2 or a C2orf28 variant 2 lacking the transmembrane domain (DM, residues 1-255 of the 284 a.a. containing full-length protein). The cells were treated with Alendronate at 0, 60 or 9004 for 72 hours. Following incubation, cell viability was determined by measuring cellular ATP levels and was expressed as a ratio of that compared with untreated cells. The data demonstrates that unlike C2orf28 deficient cells (tubulin expressing C2orf28_GT2 cells), cells expressing full-length C2orf28 are sensitive to Alendronate whereas membrane truncated forms seem to be resistant to Alendronate (FIG. 11). These data suggest that NBP requires C2orf28 membrane targeting for their cytotoxic effects.

C2Orf28 Regulates Calcium Homeostasis

Figure 12:
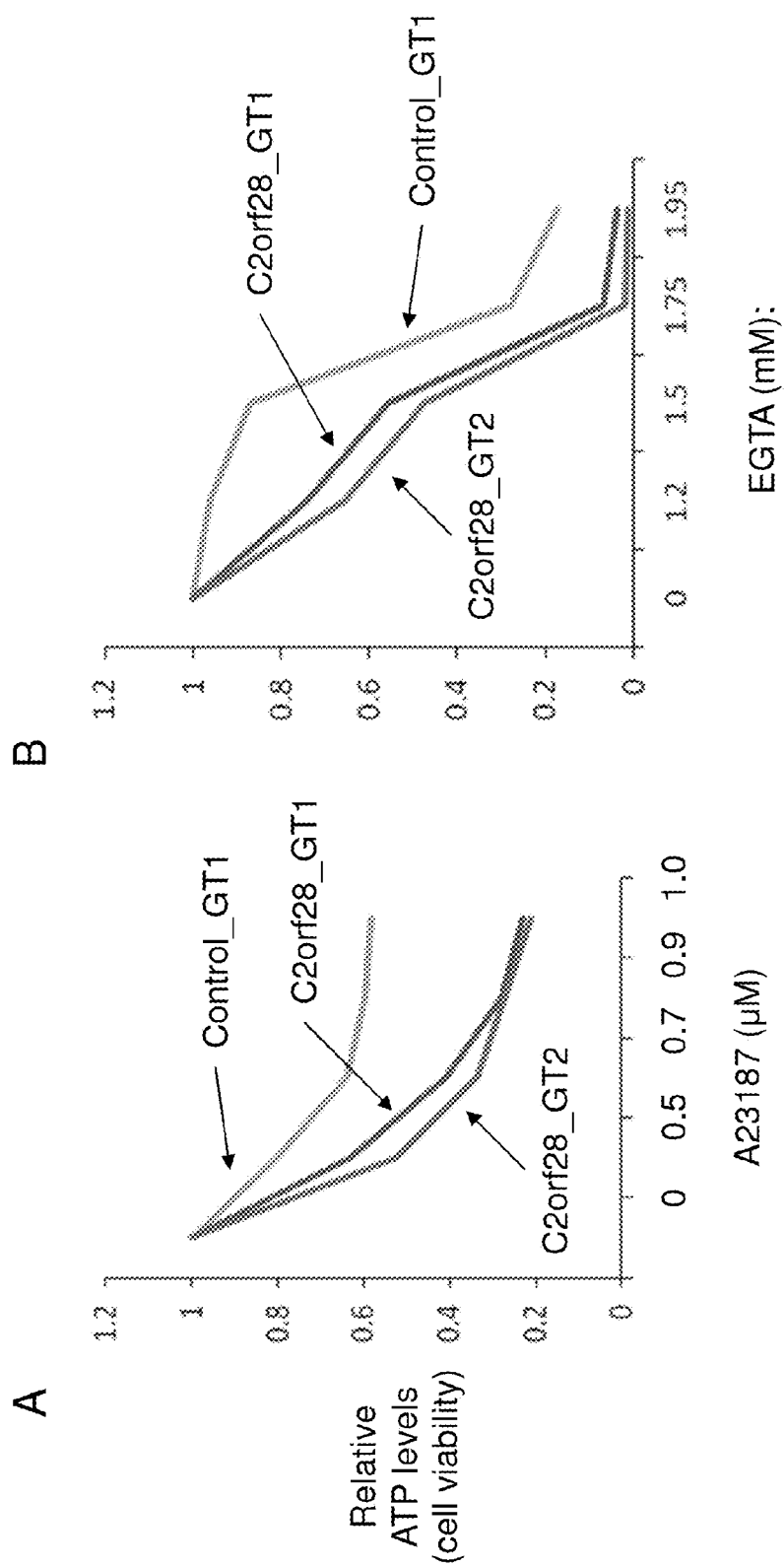
FIG. 12. C2orf28 and Calcium Sensitivity. Control and C2orf28 deficient cells were treated for 24 hours with the (A) calcium ionophore A23187, or (B) EGTA at the concentrations indicated. Cell viability was determined after 72 hours, by measuring cellular ATP levels and is expressed as a ratio of the compared with untreated cells.
Figure 13:
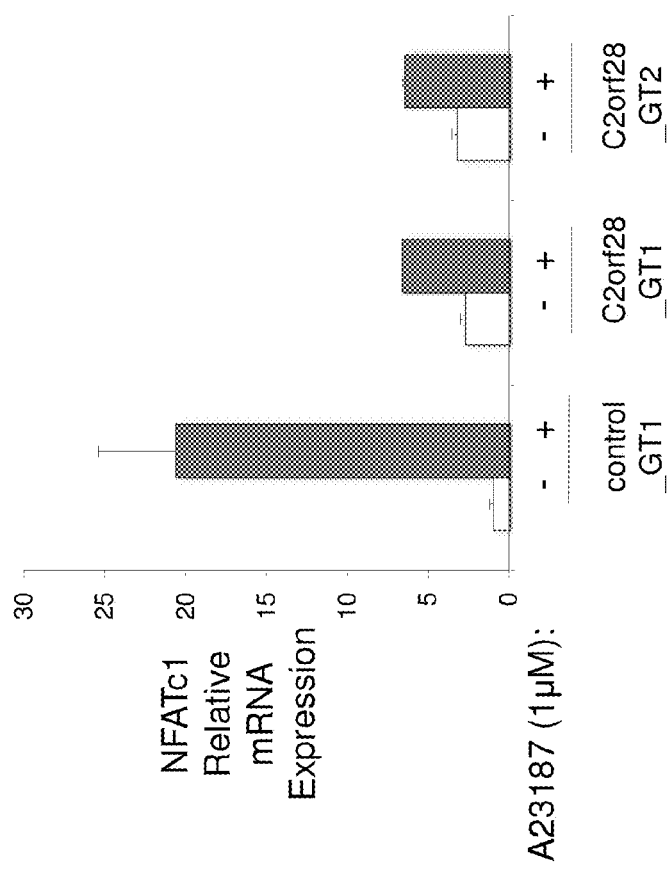
FIG. 13. A23187-induced NFATc1 Expression. Control and C2orf28 deficient cells were treated for 12 hours with 1 µM A23187. After 12 hours, relative levels of NFATc1 mRNA expression were measured.

The data also demonstrates that C2orf28 deficient cells are sensitive to intracellular calcium depletion (FIG. 12) and that C2orf28 deficient cells are defective in A23187-induced NFATc1 gene expression (FIG. 13). These findings suggest that in C2orf28 may play a role in regulating calcium induced NFAT signaling within the cell.

Materials

Reagents were obtained from the following sources: Antibody to Rapla from Santa Cruz Biotechnology; Antibody to HDJ-2 from Fischer Scientific, Antibody to HA from Cell Signaling Technology. Alendronate, Ibandronate, Pamidronate, Etidronate, Tiludronate, A23187, EGTA, and SYBR Green JumpStart Taq ReadyMix from Sigma Aldrich;

Fibronectin from Calbiochem; FuGENE 6 and Complete Protease Cocktail from Roche; 16% paraformaldehyde solution from Electron Microscopy Sciences; IMDM Glutatmax, α-MEM, SuperScript II Reverse Transcriptase, Alexa Fluor 568 secondary antibodies, Platinum Pfx, Platinum Taq DNA Polymerase and inactivated fetal calf serum (IFS) from Invitrogen; H3 Labeled Alendronate and Zolendronic Acid from Moravek.

Cell Lines and Cell Culture

KBM-7 cell lines were cultured in IMDM with 10% IFS. 3T3-E1 were obtained from ATCC and cultured in α-MEM+ 10% FBS.

cDNA Manipulations and Mutagenesis

The cDNAs for C2orf28 were cloned from a human R4 cell line cDNA library into the SalI and NotI sites of pRK5, pLKO.1, or pMSCV. All constructs were verified by DNA sequencing.

Synthesis of Fluorescently Labeled Alendronate

A quantity of 1.13 μmol of the amine-reactive probe Alexa Fluor-488 carboxylic acid 2,3,5,6-tetrafluorophenyl ester (AF-488; Invitrogen) dissolved in DMSO was mixed with 11.3 μmol of Alendronate [dissolved in bicarbonate buffer, pH 9.0 (i.e., a 1:10 molar ratio)]. The volume was made up to 1 ml with distilled water and the solution incubated for 2 hours at room temperature with mixing. To precipitate Alendronate, 19.8 μmol of CaCl2 were added and the mixture was centrifuged (14,000 g, 10 minutes). To bind the Ca+2 and resolubilize the Alendronate, 19.8 μmol of EGTA was added to the precipitate. PBS (100 μl) was added until all Alendronate-AlexaFluor-488 (a.k.a., AF-ALN) had dissolved and the solution was mixed for 30 minutes.

Mammalian Retroviral Transduction

To generate virus, mRNA-encoding plasmids were co-transfected with the Gag-pol envelope and CMV VSV-G packaging plasmids into actively growing HEK-293T using FuGENE 6 transfection reagent. Virus containing supernatants were collected at 48 hours after transfection, centrifuged to eliminate cells, and target cells (2,000,000) infected in the presence of 8 μg/ml polybrene. 24 hours after infection, the cells were given or split into fresh media and selected for two weeks with 200 ng/ml puromycin.

Protein Expression Analysis

Cells were pelleted by centrifugation at 9,000 rpm for 30 seconds, rinsed once with ice-cold PBS and lysed with Triton-X 100 containing lysis buffer (40 mM HEPES [pH 7.4], 2 mM EDTA, 150 mM NaCl, 50 mM NaF, 1% Triton-X 100, and one tablet of EDTA-free protease inhibitors [Roche] per 25 ml). The soluble fractions of cell lysates were isolated by centrifugation at 13,000 rpm for 10 minutes in a microcentrifuge. Lysate protein concentrations were normalized by Bradford assay (Bio-Rad). Proteins were then denatured by the addition of sample buffer and by boiling for 5 minutes, resolved using 4%-20% SDS-PAGE (Invitrogen), and analyzed by immunoblotting.

Immunofluoresence Assays 25,000-100,000 cells were plated on fibronectin-coated glass coverslips, fixed with 4% paraformaldehyde, and permeabilized with 0.2% Triton X-100. Permeabilized cells were blocked in 0.25% BSA PBS, incubated with primary antibody in blocking buffer overnight at 4° C. and subsequently incubated with secondary antibodies (diluted in blocking buffer 1:1000) for one hour at room temperature. 2-4×PBS washes were used in between all preceding steps. The coverslips were mounted on glass slides using Vectashield containing DAPI (Vector Laboratories) and imaged with 63× objective using epifluorescence microscopy.

Gene Expression Analysis

Total RNA was isolated and reverse-transcription was performed from cells grown in the indicated conditions. The resulting cDNA was diluted in DNase-free water (1:20) followed by quantification by real-time PCR. Data is expressed as the ratio between the expression of the target gene to the housekeeping gene, 18s. Each treated sample was normalized to the level of the vehicle controls of the same cell type. The following primers were used for quantitative real-time PCR:

```
NFATc1                              (SEQ ID NO: 17)
F'-GAAGTTCAATGTCGGAGTTTCTGA (SEQ ID NO: 18)
R'-GCATCACAGGGAAGACCGTGT 18s                                 (SEQ ID NO: 19)
F'-CTTAGAGGGACAAGTGGC (SEQ ID NO: 20)
R'-ACGCTGAGCCAGTCAGTGTA
```

Example 3

Role of TBONE in Osteoblast Differentiation and Osteoclastogenesis

This example demonstrates that TBONE is important for osteoblast differentiation and may play a critical role in both basal and NBP-stimulated induction of gene expression, required for osteoblast activity and function. The example also demonstrates that cells deficient in TBONE show a dramatic reduction in their level of RANKL production, similar to that of NBP treatment, suggesting that such a reduction in RANKL expression may lead to a dramatic reduction in stimulating osteoclastogenesis and lead to bone regeneration.

Background

In addition to providing both structural support and rigidity, the human skeletal system performs the vital role of serving as a central repository for the storage of calcium phosphate and various other biologically active molecules, such as growth factors. As a result, the process of bone remodeling with the human body, is an elaborate and dynamic process, requiring the systematically choreographed genesis and catalysis of mineral deposits to maintain calcium homeostatic. This process is tightly regulated via specialized cellular components, responsive to cellular and hormonal signals, allowing them to assay their surroundings and adjust to an ever-changing environment. Bone tissue is broken down and reabsorbed by multinucleate cells called osteoclast, derived from monocytes which originate in the bone marrow. The cells responsible for the deposition of minerals and generation of osteoid, the organic component of bone, are the mesenchymal stem cell derived osteoblasts. One key regulatory molecule, responsible for stimulating osteoclast differentiation and function is Rank-ligand (RANKL), which is produced from both osteoblasts and their precursor cells. However, the stimulatory effect of RANKL are balanced by the negative inhibitory effects of the molecule osteoprotegerin (OPG), which is also produced by osteoblast and is positively regulated by Estrogen levels within the body. Consequently perturbation of Estrogen levels, such as in the case of postmenopausal women, can lead to excess stimulation of osteoclast activity resulting in osteoporosis.

Effect of TBONE on Osteoblast Differentiation

Figure 14:
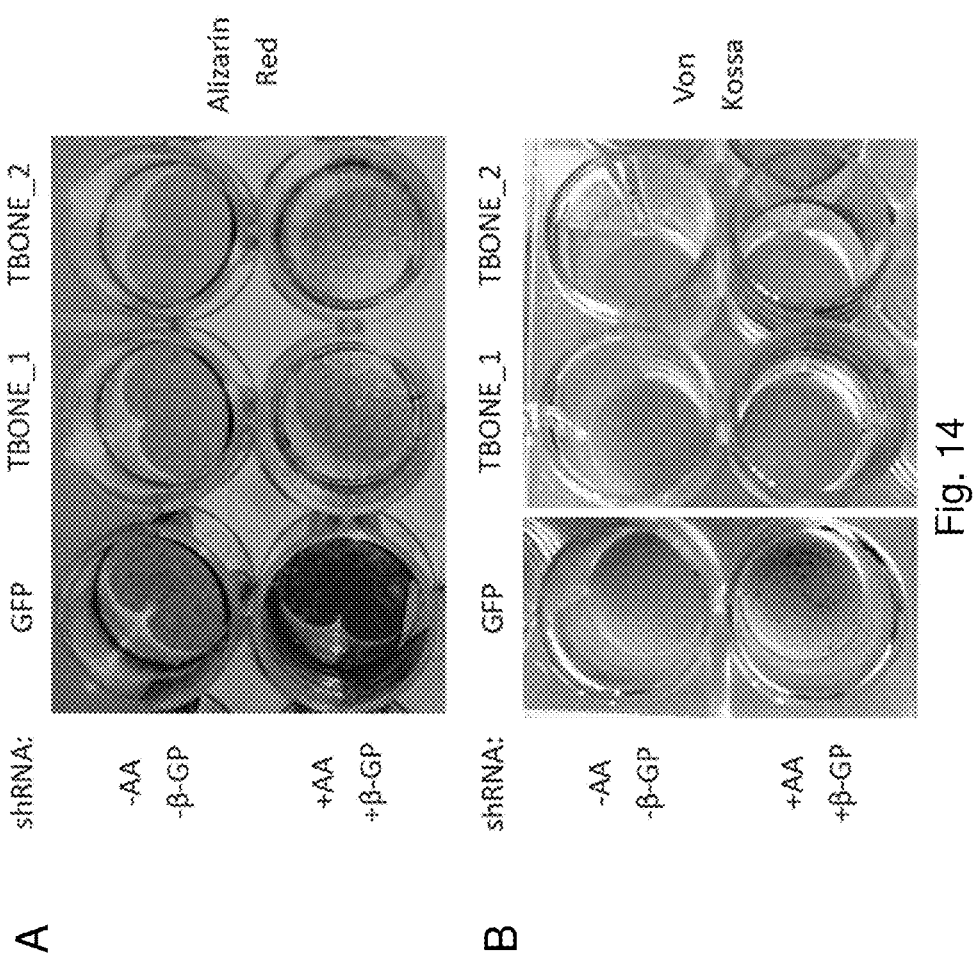
FIG. 14. Effect of TBONE on osteoblast calcium and phosphate deposition. shRNA-mediated TBONE knockdown (TBONE_1 and TBONE_2) and transfection control (GFP) cells were differentiated and analyzed for extracellular deposition of (A) calcium and (B) phosphate.

Since NBPs and calcium potentially play an important role in regulating osteoblast function, studies were performed to evaluate the role of TBONE in osteoblast differentiation. For the experiment, wild-type and GFP positive MC3T3-e1 cells were transiently transfected with small-hairpin RNA (shRNA). GFP positive cells were treated with a shRNA designed to target and disrupt GFP expression (transfection control), while wild-type cells were treated with one of two shRNA constructs (TBONE_1 and TBONE_2) designed to target and disrupt expression of Apr3. The cells were then subjected to conditions for promoting osteoblast differentiation, 50 μg/ml ascorbic acid and 10 mM B-glycerophosphate for 2 weeks, and analyzed for extracellular calcium deposition using Alizarin Red or phosphate deposition using the Von Kossa method. As shown in FIGS. 14A&B, following treatment with ascorbic acid (AA) and β-glycerophosphate (β-GP) the GFP transfection control cells were able to differentiate into osteoblasts as evidence by the presence of calcium (A) and phosphate (B) precipitation (dark color). While disruption of TBONE expression strongly impaired osteoblast differentiation and its subsequent biological function, preventing both calcium (A) and phosphate (B) deposition (FIGS. 14A&B).

Effect of TBONE on Basal and NBP Stimulated Osteoblastic Gene Expression

In addition to analyzing calcium and phosphate mineralization, additional studies were performed to examine the expression profile for osteocalcin (OC), bone sialoprotein (BSP) and alkaline phosphatase (ALPL). Several studies have shown that each of these well-established osteoblast specific genes are important for proper osteoblast function and calcium deposition (F. Otto et al., (1997) *Cell:* 89, 765; S. Mundlos et al., (1997) *Cell:* 89, 773; and G. Karsenty, (2008) *Annu Rev Genomics Hum Genet:* 9, 183; all of which are hereby incorporated by reference.)

Figure 15:
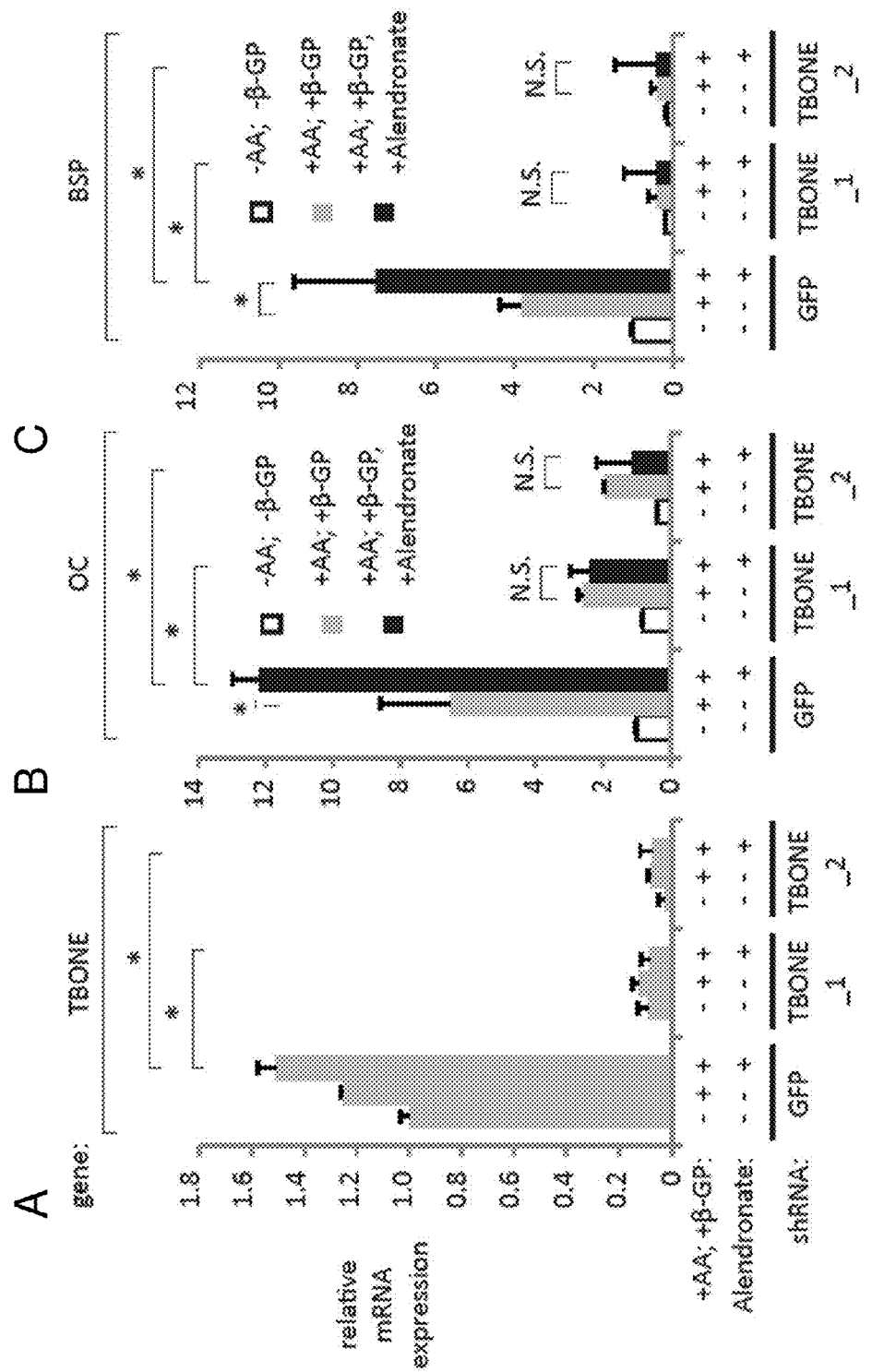
FIG. 15. Basal and NBP-potentiated osteoblastic gene expression. shNA-mediated TBONE knockdown (TBONE_1 and TBONE_2) and transfection control (GFP) cells were treated with 10 nM Alendronte or vehicle and analyzed using real-time RT-PCR for mRNA expression of (A) TBONE, (B) osteocalcin (OC), and (C) bone sialoprotein (BSP).
Figure 16:
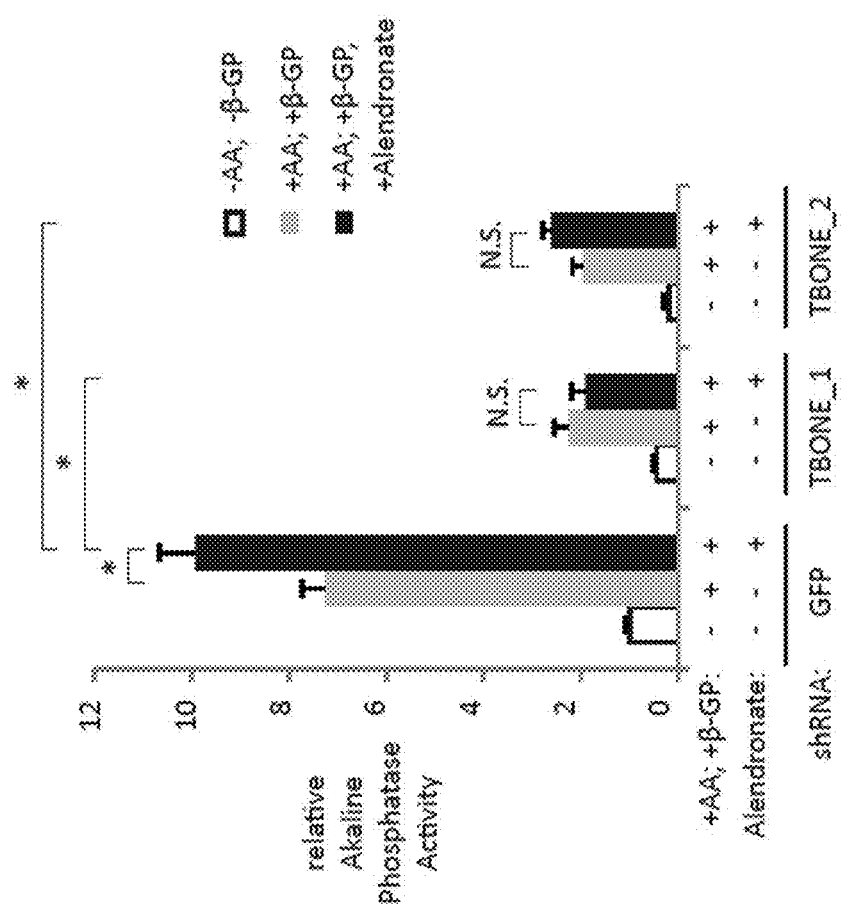
FIG. 16. Basal and NBP-potentiated osteoblastic alkaline phosphatase activity. shNA-mediated TBONE knockdown (TBONE_1 and TBONE_2) and transfection control (GFP) cells were treated with 10 nM Alendronte or vehicle and analyzed for alkaline phosphatase activity colormetrically.

Briefly, GFP control and TBONE knockdown cells were generated and subjected to differentiation as described above. Following the two week incubation, cells were treated with 10 nM Alendronate (exemplary NBP) or vehicle and analyzed by real-time RT-PCR using TBONE, OC and BSP gene specific oligonucleotide primers (FIG. 15). Alkaline phosphatase activity was measured using a colorimetric based assay designed to indicate ALPL activity by changing color following the dephosphorylation of p-nitrophenyl phosphate (pNPP) (FIG. 16). As indicated in FIG. 15A, shRNA treatment with TBONE_1 and TBONE_2 resulted in a dramatic knockdown in the expression of TBONE as compared to GFP control. Furthermore, differentiation (+AA;+β-GP) as well as NBP treatment lead to an increase in relative TBONE expression. This suggests, that both differentiated osteoblast and NBP stimulated osteoblasts display a higher level of TBONE expression than that of their precursor cells. In addition, TBONE knockdown cells (TBONE_1 and TBONE_2) fail to demonstrate a NBP-stimulated induction of TBONE. Cells deficient in TBONE expression also fail to demonstrate an increase in basal or NBP-stimulated gene expression of OC, BSP, and ALPL, when compared to GFP control, further supporting the initial finding (FIGS. 15 and 16).

These finding suggest that TBONE is important for the differentiation of osteoblast cells. Furthermore, the data suggests that TBONE may play a role in in the basal expression level of several genes necessary to carryout normal osteoblast function and mineralization for proper bone formation. Lastly, the data demonstrates that TBONE could be essential in promoting the NBP-stimulated induction of osteoblast activity, required for NBP drug treatment in patients.

Effect of TBONE on Osteoclastogenesis

Figure 17:
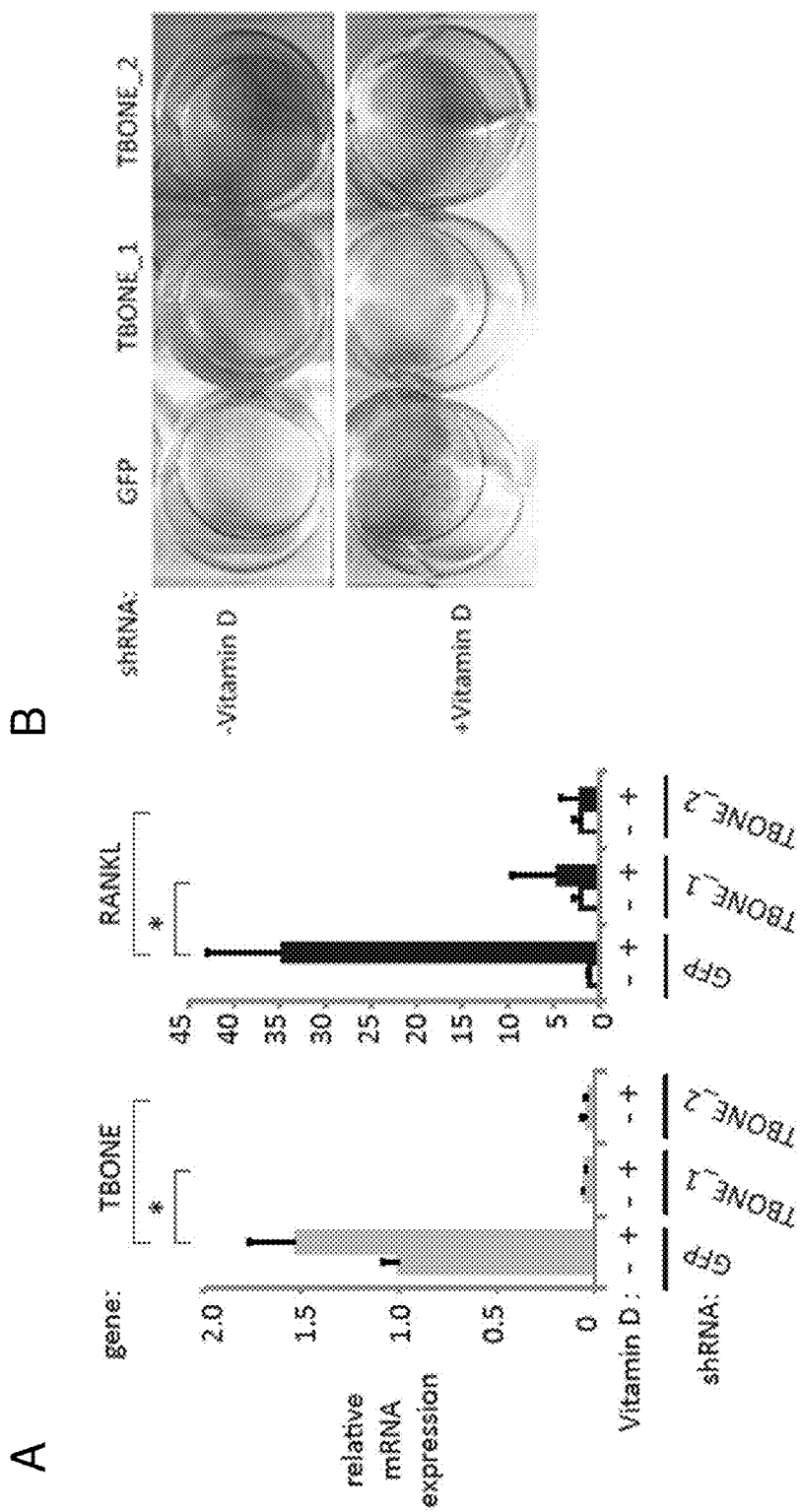
FIG. 17. Effect of TBONE on osteoblastic expression of RANKL mRNA. shNA-mediated TBONE knockdown (TBONE_1 and TBONE_2) and transfection control (GFP) cells were treated with 100 nM Vitamin D or vehicle and analyzed using real-time RT-PCR for mRNA expression of RANKL FIG. 18. Effect of Alendronate on osteoblastic expression of RANKL mRNA. ST-2 cells were treated with 100 nM Vitamin D, prior to treatment with Alendronate or vehicle and analyzed for (A) mRNA expression of RANKL by real-time RT-PCR, or (B) co-cultured with RAW 264.7 macrophages and analyzed for tartrate-resistant acid phosphatase (TRAP) activity.

Given that osteoblasts express and secrete RANKL, capable of stimulating the differentiation of monocytes into osteoclasts, studies were performed to evaluate the effects of TBONE and NBP treatment on osteoclastogenesis. For the experiment, wild-type and GFP positive ST-2 osteoblast cells were transiently transfected with small-hairpin RNA (shRNA). GFP positive cells were treated with a shRNA designed to target and disrupt GFP expression (transfection control), while wild-type cells were treated with one of two shRNA constructs (TBONE_1 and TBONE_2) designed to target and disrupt expression of Apr3. The cells were then treated with 100 nM Vitamin D, a known inducer of RANKL, or the corresponding vehicle control. Following treatment, two assay methods were employed to evaluate RANKL expression levels within the knockdown and control cells. First, total RNA was extracted from each group of experimental cells and analyzed by real-time RT-PCR using TBONE and RANKL gene specific oligonucleotide primers (FIG. 17A). Second, cells were co-cultured with RAW 264.7 macrophages and analyzed for tartrate-resistant acid phosphatase (TRAP) activity, to determine whether RANKL produce by each of the Vitamin D treated osteoblast groups was sufficient to simulate osteoclastogenesis (FIG. 17B). As demonstrated in FIG. 17A, TBONE knockdown cells (TBONE_1 and TBONE_2) display an impaired RANKL mRNA induction by Vitamin D compared to GFP control. In addition knockdown of TBONE largely blocked Vitamin D simulated osteoclastogenesis, as evidence by reduced TRAP activity, demonstrating a potential physiologic relevance and supporting TBONE as a therapeutic target for bone regeneration.

Figure 18:
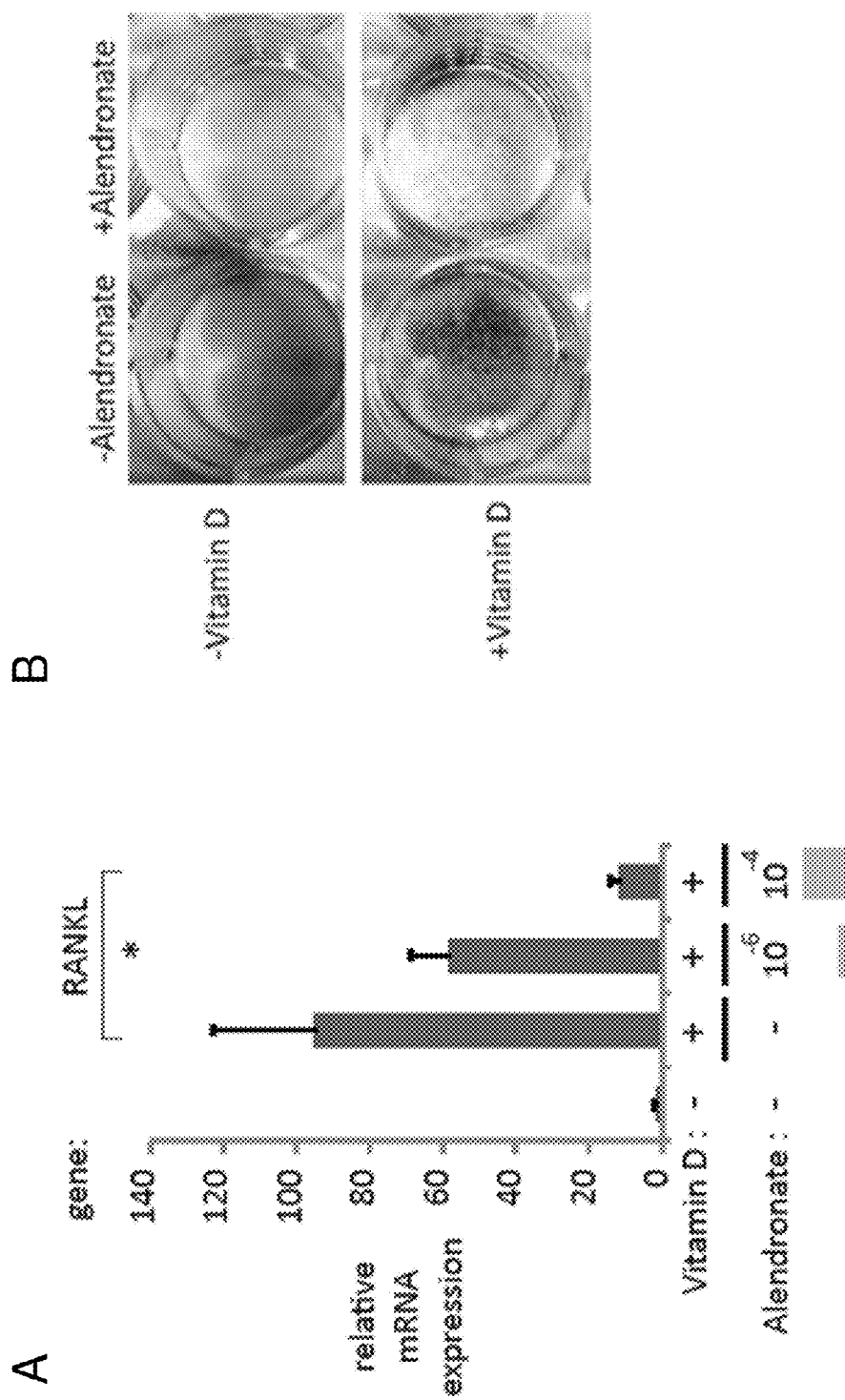

In order to further explore the link between TBONE and NBP treatment, studies were carried out to evaluate the effect of NBP treatment on osteoclastogenesis. Briefly, wild-type ST-2 osteoblast cells were treated with 100 nM Vitamin D along with and increasing concentration of Alendronate or vehicle control. Following treatment, two assay methods were employed to evaluate RANKL expression levels. First, total RNA was extracted from each group of experimental cells and analyzed by real-time RT-PCR using RANKL gene specific oligonucleotide primers (FIG. 18A). Second, cells were co-cultured with RAW 264.7 macrophages and analyzed for tartrate-resistant acid phosphatase (TRAP) activity, to determine whether RANKL produce by each of the osteoblast experimental or control groups was sufficient to simulate osteoclastogenesis (FIG. 18B). As demonstrated in FIG. 18A, cells treated with Alendronate showed impaired RANKL mRNA induction by Vitamin D, in a dose dependent fashion, as compared to control. In addition NBP treatment with Alendronate ameliorated Vitamin D simulated osteoclastogenesis, as evidence by reduced TRAP activity, demonstrating a potential physiologic relevance and further supporting TBONE's role in NBP drug treatment.

Figure 19:
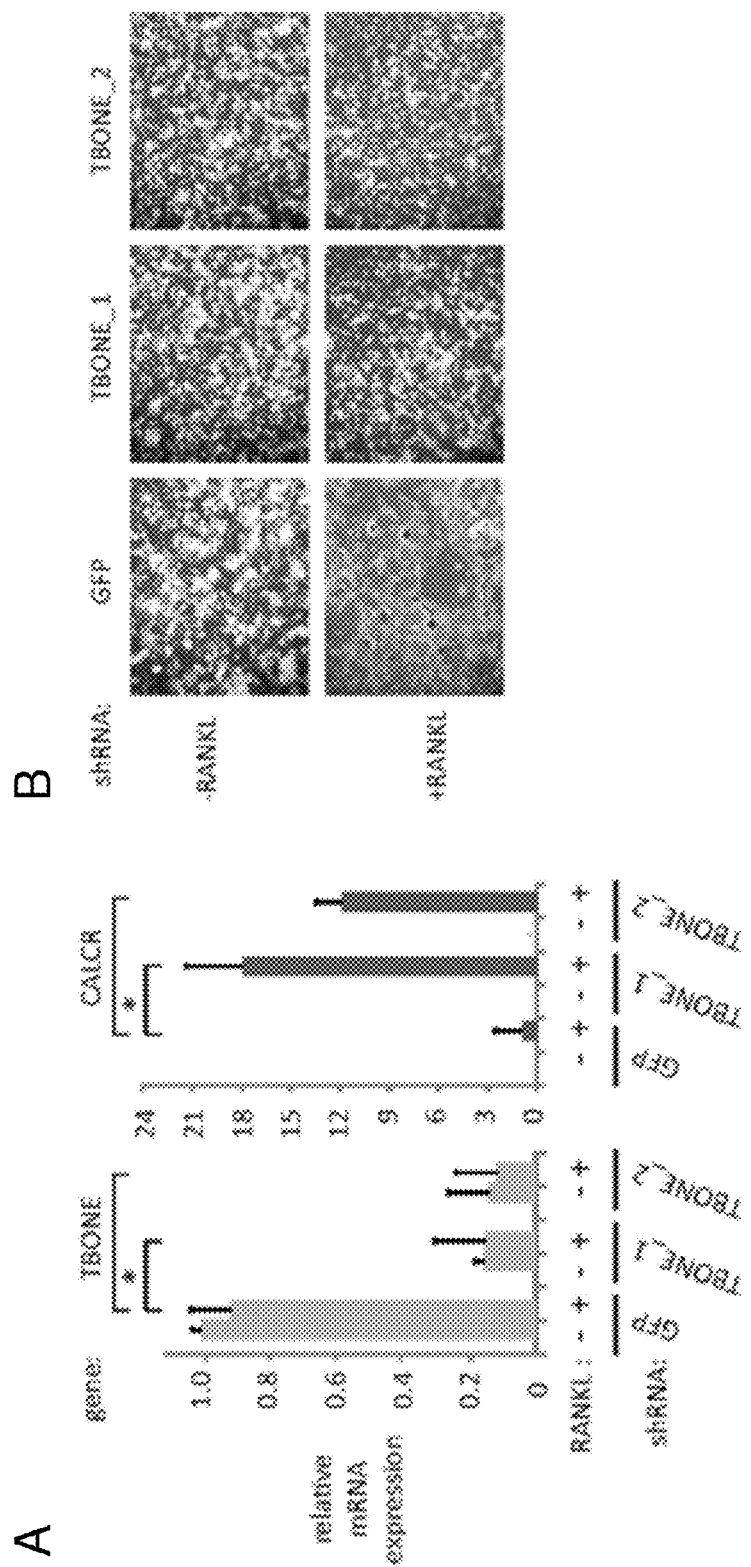
FIG. 19. Effect of TBONE on RANKL-medicated induction of TRAP activity. shNA-mediated TBONE knockdown (TBONE_1 and TBONE_2) and transfection control (GFP) RAW 264.7 macrophages were treated with 50 ng/ml RANKL for 5 days and analyzed for (A) real-time RT-PCR mRNA expression of TBONE and the calcitonin receptor (CALCR), and (B) liquid TRAP activity.

In order to determine if TBONE plays a role in directly regulating osteoclastogensis, TBONE was knockdown in macrophages to evaluate its potential effect on RANKL stimulated differentiation; by monitoring lineage specific surface marker expression of the calcitonin receptor (CALCR), a well-established indicator of osteoclast activity (J. Lam et al., (2000) *J Clin Invest:* 106, 1481; D. L. Lacey et al., (1998), *Cell:* 93, 165; and C. Minkin, (1982), *Calcif Tissue Int:* 34, 285; all of which are hereby incorporated by reference). Briefly, wild-type and GFP positive RAW 264.7 macrophages cells were transiently transfected with shRNA to knockdown GFP and Arp3 as described above. The cells were treated with 50 ng/ml RANKL for 5 days. Following treatment, two assay methods were employed to evaluate RANKL stimulated differentiation. First, total RNA was extracted from each group of experimental cells and analyzed by real-time RT-PCR using TBONE and calcitonin receptor (CALCR) gene specific oligonucleotide primers. Second, cells were analyzed for tartrate-resistant acid phosphatase (TRAP) activity. The data demonstrated that knockdown of TBONE remarkably promoted the expression of CALCR, a strong negative regulator of osteoclast function (FIG. 19A). In addition, the findings also suggest, that knockdown of TBONE strongly impairs RANKL-mediated TRAP activity (FIG. 19B).

Osteoclast Differentiation Correlates with NBP Side Effects in Patients

Figure 20:
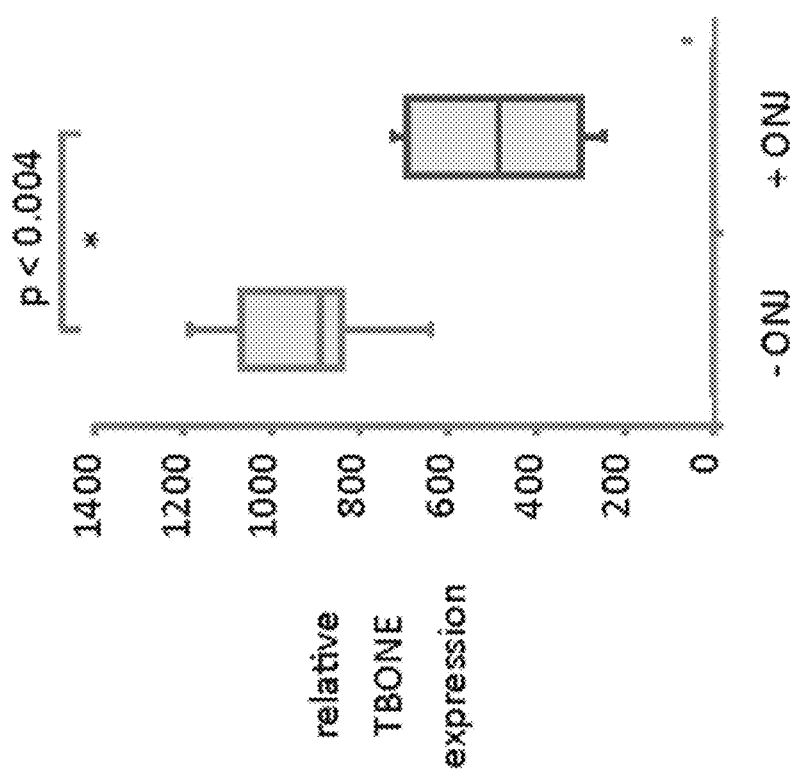
FIG. 20. TBONE expression in NBP-treated patients. The level of mRNA expression of TBONE was analyzed by real-time RT-PCR in NBP-treated multiple myeloma patients, who did (+) or did not (−) manifest osteonecrosis of the jaw (ONJ).

Previously studies suggest, that altered expression of key members of the NFAT (Nuclear Factor of Activated T-cells) family of transcription factors, are involved in the development of osteonecrosis of the jaw (ONJ) in multiple myeloma patients treated with NBPs (N. Raje et al., (2008) *Clin Cancer Res:* 14, 2387; which is hereby incorporated by reference). To investigate the role of TBONE in regulating the onset of ONJ, peripheral mononuclear cells samples were collected from subjects treated with NBP, with (+ONJ) and without (−ONJ) osteonecrosis of the jaw. Total RNA was extracted and analyzed by real-time RT-PCR using TBONE gene specific oligonucleotide primers. The data demonstrates that those patients treated with NBP who develop ONJ, have a statistically significant down-regulation of TBONE mRNA expression (FIG. 20).

These findings strongly suggest the TBONE is essential in promoting osteoblast differentiation, regulating osteoclastogenesis and maintaining proper bone homeostasis in the body. The studies also demonstrate the critical role of TBONE in helping to regulate bone remodeling within the body and promote NBP-mediated induction several key genes in promoting bone generation. Furthermore, the findings illustrate a physiologically relevant correlation, between TBONE expression levels and its ability to ameliorate the onset of deleterious side effects associated with NBP treatment. Taken together, these findings highlight the overall importance of TBONE as a cellular therapeutic target and its potential role helping to identify second generation drugs candidates and improve existing NBP treatment.

Example 5

Animal Model Systems for Studying Calcium Disorders

The current example describes generation of a TBONE knock-out mouse, to examine the role of TBONE in regulating bone homeostasis in vivo and support the previous in vitro findings. While this example describes the use and manipulation of a mouse model system, it will be readily apparent to one skilled in the art, that a wide number of non-human model systems (i.e.—animal, non-human primate, insect, yeast, fish, etc.) may be exploited using a variety of well-established methods. Any such method may be used to produce an organism with altered (reduced, increased and/or modified) expression, activity and/or function for one or more biomarkers associated with a calcium disorder, such as, but not limited to, C2orf28 (APR3), NELL1, NELL2, Phospholipase C-like 1(PLCL-1), Ephrin receptor B1 (EPHB1), Syntrophin Gamma 1(SNTG1) and combination thereof. Such an approach may be used to identify NBP-associated gene target-based diagnostics or therapeutics for any of a variety of calcium disorders described within the current application. In particular, the approach may be utilized to examine the role of biomarkers in regulating, diagnosing, monitoring and/or treating hormone withdrawal-dependent bone deterioration, atherosclerosis, renal arterial stenosis and bone malformations.

Generation of a TBONE Knock-Out (KO) Mouse

To characterize the role of TBONE in organismal physiology, a TBONE deficient mouse was created using a Cre-Lox system. Briefly, embryonic stem (ES) cells were obtained from the European Conditional Mouse Mutagenesis program (EUCOMM), containing a loxP flanked allele of the TBONE gene, and injected into blastocysts to obtain chimeric offspring. The chimeric mice were then bred to obtain germline transmitted heterozygous loxP-TBONE animals, which were then subsequently bred to homozygousity. To obtain homozygous null TBONE animals, the TBONE gene was deleted in homozygous floxed TBONE animals, by Cre-mediated insertion of the ubiquitously active minimal cytomegalovirus (CMV) promoter. While viable, homozygous null TBONE mice were found to displayed an approximately 20% reduction in weight as compared to age-matched wild-type control mice (data not shown).

Use of a Knock-Out Animal Model System to Evaluate Bone and NBP-Associated Gene Target-Based Diagnostics and Therapeutics for NBP-Responsiveness Generation of a knock-out animal model system, such as the TBONE knock-out mouse, allows one to examine the contribution of individual or multiple NBP gene targets on bone remodeling in vivo. While the current example demonstrates the creation of a TBONE deficient mouse, the current invention encompasses the recognition that one or more biomarkers associated with a calcium disorder, such as, but not limited to, C2orf28 (APR3), NELL1, NELL2, Phospholipase C-like 1(PLCL-1), Ephrin receptor B1 (EPHB1), Syntrophin Gamma 1(SNTG1) and combination thereof, may be targeted for generating knock-out organisms. In addition to affording one the ability to examine the contribution of an individual gene in regulating bone remodeling in vivo, use of an animal model helps provide insight into bone maturation during each critical phase of the organisms growth and development. One can monitor bone development and maintenance in mice using a variety of techniques, such as morphometric and histiometric analysis (Lacey, D. et al., L., (1998) *Cell:* 93; 165-176; which is hereby incorporated by reference).

It will also be appreciated by one skilled in the art, that a variety of methods exist for altering and/or treating an organism (wild-type or knock-out), in order to manifest and/or mimic a specific human disease phenotype. Consistent with the key role of sex hormones in proper bone function, ovariectomized female animals are widely utilized to model post-menopausal osteoporosis (Inada, M., et al., (2011) *Clinical calcium:* 21; 164-170; which is hereby incorporated by reference). An animal may also be placed in a state of chronic inflammation to monitor the effects of bone loss associated with inflammatory disorders (Hardy, R., et al., (2009) *Journal of Endocrinology:* 201(3):309-20; which is hereby incorporated by reference). Such approaches can be used to monitor the effect of one or more biomarkers (such as TBONE or other related NBP-gene targets) in altering (preventing, delaying or increasing) the onset of a calcium disorder (i.e., osteoporosis, atherosclerosis, renal arterial stenosis, etc.) and its role in regulating NBP treatment. These approaches may also be used in conjunction with specific assay methods to determine if one or more biomarkers (TBONE or other related NBP-gene targets) are refractory to the effects of NBPs on maintaining bone density; or influence the prevalence of side effects commonly associated with NBP treatment, such as osteonecrosis (Samadfam, R., et al., (2007) *Journal of bone and mineral research:* 22, 55-63; and Bi, Y., et al., (2010) *The American journal of pathology:* 177, 280-290; which are hereby incorporated by reference). Taken together, these experimental model systems and experimental approaches will not only lead to the development of diagnostic tools, but provide valuable clinical insight in determining a subjects predisposition to a given drug response and enable a physician to determine an appropriate drug regimen for treating a subject.

EQUIVALENTS

Those skilled in the art will recognize, or be able to ascertain using no more than routine experimentation, many equivalents to embodiments of the inventions described herein. The scope of the present invention is not intended to be limited to the above Description, but rather is as set forth in the following claims:

In accordance with 37 CFR 1.52(e)(5), a Sequence Listing in the form of a text file (entitled "Seq_Listing_0342941-0416 ST25.txt," created on Apr. 9, 2013 and 72 Kb) is incorporated herein by reference in its entirety.

We claim:

1. A method of identifying a candidate agent for diagnosis, monitoring, and/or treatment of a calcium disorder comprising steps of:
   (a) providing an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product; and
   (b) testing the effect of the agent in a system that serves as a model for a calcium disorder, wherein the agent is identified as a candidate agent for treatment of a calcium disorder if the agent produces an effect in the system that is indicative of potential therapeutic efficacy for treatment of a calcium disorder.

2. The method of claim 1, wherein the agent is not a bisphosphonate.

3. The method of claim 1, wherein the agent is a nitrogenous bisphosphonate.

4. The method of claim 1, wherein the agent is not C2orf28 (ARP3), NELL1, or NELL2 or a biologically active fragment or variant of C2orf28 (ARP3), NELL1, or NELL2.

5. The method of claim 1, wherein the agent comprises a small molecule, antibody, polypeptide, lipid, or nucleic acid.

6. The method of claim 5, wherein the antibody comprises a monoclonal antibody, antibody fragment, single chain antibody, bispecific antibody, diabody, tribody, tetrabody, nanobody, single domain antibody, VHH domain, human antibody, fully humanized antibody, partially humanized antibody, affibody, anticalin, adnectin, or chimeric antibody.

7. The method of claim 5, wherein the polypeptide comprises an affibody, anticalin, or adnectin.

8. The method of claim 1, wherein the system comprises a cell culture comprising osteoclasts, osteoblasts, osteocytes, or a combination thereof, or a non-human animal that serves as a model of a calcium disorder.

9. The method of claim 1, wherein an effect indicative of potential therapeutic efficacy is an effect that would be produced in the system by a nitrogenous bisphosphonate present at a concentration that corresponds to a concentration that is therapeutically useful for treatment of a calcium disorder in a mammalian subject.

10. The method of claim 1, wherein providing an agent that binds to or modulates expression, level, modification, localization, or activity of a C2orf28 (APR3), NELL1, NELL2, Phospholipase C-like 1(PLCL-1), Ephrin receptor B1 (EPHB1), or Syntrophin Gamma 1(SNTG1) gene product comprises identifying or generating an agent that binds to or modulates expression, level, modification, localization, or activity of said gene product.

11. The method of claim 1, wherein the calcium disorder is selected from the group consisting of osteoporosis, osteitis defomans (Paget's disease), hyperparathyroidism, hypercalcemia of malignancy, arthritis and osteolytic bone metastisis.

* * * * *

SEQUENCE LISTING

<160> NUMBER OF SEQ ID NOS: 20

<210> SEQ ID NO 1
<211> LENGTH: 1098
<212> TYPE: DNA
<213> ORGANISM: Homo sapiens

<400> SEQUENCE: 1

```
gcaccaaggg aacggaaaat ggcgcctcac gacccgggta gtcttacgac cctggtgccc      60
tgggctgccg ccctgctcct cgctctgggc gtggaaaggg ctctggcgct acccgaggta     120
cagaagcaag tttgaggtcg ggctgaagca gggtcgctgg ccagccgtgc gtcgcgctcg     180
ccagcggctc ccccttctcc tcggcgggcc tgcggttctg atttcgtccc tgacgcttcc     240
cgaccctgcc cagccagata tgcacccaat gtccagggag cgtgcaaaat ttgtcaaaag     300 tggccttta ttgtaaaacg acacgagagc taatgctgca tgcccgttgc tgcctgaatc     360
agaagggcac catcttgggg ctggatctcc agaactgttc tctggaggac cctggtccaa     420
actttcatca ggcacatacc actgtcatca tagacctgca agcaaacccc ctcaaaggtg     480
acttggccaa caccttccgt ggctttactc agctccagac tctgatactg ccacaacatg     540
tcaactgtcc tggaggaatt aatgcctgga atactatcac ctcttatata gacaaccaaa     600
tctgtcaagg gcaaaagaac ctttgcaata acactgggga cccagaaatg tgtcctgaga     660
atggatcttg tgtacctgat ggtccaggtc ttttgcagtg tgtttgtgct gatggtttcc     720
atggatacaa gtgtatgcgc cagggctcgt tctcactgct tatgttcttc gggattctgg     780
gagccaccac tctatccgtc tccattctgc tttgggcgac ccagcgccga aaagccaaga     840
cttcatgaac tacataggtc ttaccattga cctaagatca atctgaacta tcttagccca     900
gtcagggagc tctgcttcct agaaaggcat ctttcgccag tggattcgcc tcaaggttga     960
ggccgccatt ggaagatgaa aaattgcact cccttggtgt agacaaatac cagttcccat    1020
tggtgttgtt gcctataata aacacttttt tcttttttt tcctctcttt ctttttaaaa    1080
aaaaaaaaaa aaaaaaaa                                                  1098
```

<210> SEQ ID NO 2
<211> LENGTH: 1278
<212> TYPE: DNA
<213> ORGANISM: Homo sapiens

<400> SEQUENCE: 2

```
ggagggccc gagtttctgc gaagccgcga cctcggcgtc cggacgcggg gaacaccggg       60
ctgagggagt ctgcagtcgg ctccgggaag ccgcgcggcg acggggagg ccttcactaa     120 aggggaaaag gaagaggggg tcggccagta tccccgaaag agggctaggg cgcatgaaga    180
```

-continued

```
ccagcgcaga gctccacgag caggaaaagc ccccaagcag ccccagggcg actggaccgg      240
gccgcttagg ccacgcccgg ggaagagggc ctgacgcgct gcggggcggg gccgcggggc      300
cgggtcgcgc gagcagcgga gcaccaaggg aacggaaaat ggcgcctcac gacccgggta      360
gtcttacgac cctggtgccc tgggctgccg ccctgctcct cgctctgggc gtggaaggg       420 ctctggcgct acccgagata tgcacccaat gtcagggag cgtgcaaaat ttgtcaaaag       480 tggccttta ttgtaaaacg acacgagagc taatgctgca tgcccgttgc tgcctgaatc      540
agaagggcac catcttgggg ctggatctcc agaactgttc tctggaggac cctggtccaa     600
actttcatca ggcacatacc actgtcatca tagacctgca agcaaacccc ctcaaaggtg     660
acttggccaa caccttccgt ggctttactc agctccagac tctgatactg ccacaacatg     720
tcaactgtcc tggaggaatt aatgcctgga atactatcac ctcttatata gacaaccaaa     780
tctgtcaagg gcaaaagaac ctttgcaata acactgggga cccagaaatg tgtcctgaga     840
atggatcttg tgtacctgat ggtccaggtc ttttgcagtg tgtttgtgct gatggtttcc     900
atggatacaa gtgtatgcgc cagggctcgt tctcactgct tatgttcttc gggattctgg     960
gagccaccac tctatccgtc tccattctgc tttgggcgac ccagcgccga aaagccaaga    1020
cttcatgaac tacataggtc ttaccattga cctaagatca atctgaacta tcttagccca    1080
gtcagggagc tctgcttcct agaaaggcat ctttcgccag tggattcgcc tcaaggttga    1140
ggccgccatt ggaagatgaa aaattgcact cccttggtgt agacaaatac cagttcccat    1200
tggtgttgtt gcctataata aacacttttt tctttttttt tcctctcttt cttttttaaaa    1260 aaaaaaaaaa aaaaaaaa                                                    1278
```

<210> SEQ ID NO 3
<211> LENGTH: 958
<212> TYPE: DNA
<213> ORGANISM: Homo sapiens

<400> SEQUENCE: 3

```
gcaccaaggg aacggaaaat ggcgcctcac gacccgggta gtcttacgac cctggtgccc      60
tgggctgccg ccctgctcct cgctctgggc gtggaaggg ctctggcgct acccgagata      120
tgcacccaat gtcagggag cgtgcaaaat ttgtcaaaag tggccttta ttgtaaaacg       180 acacgagagc taatgctgca tgcccgttgc tgcctgaatc agaagggcac catcttgggg     240
ctggatctcc agaactgttc tctggaggac cctggtccaa actttcatca ggcacatacc     300
actgtcatca tagacctgca agcaaacccc ctcaaaggtg acttggccaa caccttccgt     360
ggctttactc agctccagac tctgatactg ccacaacatg tcaactgtcc tggaggaatt     420
aatgcctgga atactatcac ctcttatata gacaaccaaa tctgtcaagg gcaaaagaac     480
ctttgcaata acactgggga cccagaaatg tgtcctgaga atggatcttg tgtacctgat     540
ggtccaggtc ttttgcagtg tgtttgtgct gatggtttcc atggatacaa gtgtatgcgc     600
cagggctcgt tctcactgct tatgttcttc gggattctgg gagccaccac tctatccgtc     660
tccattctgc tttgggcgac ccagcgccga aaagccaaga cttcatgaac tacataggtc     720
ttaccattga cctaagatca atctgaacta tcttagccca gtcagggagc tctgcttcct     780
agaaaggcat ctttcgccag tggattcgcc tcaaggttga ggccgccatt ggaagatgaa     840
aaattgcact cccttggtgt agacaaatac cagttcccat tggtgttgtt gcctataata     900
aacacttttt tctttttttt tcctctcttt cttttttaaaa aaaaaaaaaa aaaaaaaa      958
```

<210> SEQ ID NO 4
<211> LENGTH: 6608
<212> TYPE: DNA
<213> ORGANISM: Homo sapiens

<400> SEQUENCE: 4

| | | | | | | |
|---|---|---|---|---|---|---|
| atcgggccgc | cggcgtccgg | gctccagagg | ccgcctggct | gggcgcccgg | tgccttttgt | 60 |
| ctggcgcagg | gccggcgttt | gcatcacatt | tcggatacct | ccctctcttt | ttcgcctctc | 120 |
| cttctgcctc | ccgctcacat | cgcctcccca | ctcccgccac | cgtccccgc | cggactgcta | 180 |
| gcctcctaga | ccgaagcccg | aggacgtctc | tgcccgagcg | atgtcccctc | tccagaaagt | 240 |
| tgccgccgcc | gccgccgccg | ccgccactgc | cgccgctggg | cggtgaaaca | aagtctggcg | 300 |
| gggccgcctc | ccggtgcagg | agcgcaccgg | tgcctagcgg | ctggactccg | ctgccgggcg | 360 |
| tcccgctttc | ccccggggag | ccctaaacgc | tccaggccat | ggccgagggc | gcggccggca | 420 |
| gggaggatcc | ggcgccgccc | gacgcggcgg | ggggcgaaga | cgaccccga | gtgggcccgg | 480 |
| atgccgccgg | ggactgcgtg | acggcggcct | ctggggccg | gatgagggac | cgtcgcagcg | 540 |
| gggtcgcact | gccaggcgcc | gcggggaccc | cagcggacag | cgaggcgggc | ctcctggagg | 600 |
| cagcacgggc | gacccccgg | cgcagcagca | tcatcaagga | tccttcaaac | caaaaatgtg | 660 |
| gtggaagaaa | gaaaaccgtg | tctttcagca | gcatgccatc | ggaaaagaaa | attagcagtg | 720 |
| caaatgactg | catcagcttc | atgcaagctg | gctgtgagtt | gaagaaagtc | cggccaaatt | 780 |
| ctcgcattta | caaccgtttt | ttcactctgg | acacagacct | tcaagctctt | cgctgggaac | 840 |
| cttcaaagaa | agacctcgag | aaagccaagc | ttgatatttc | tgccataaaa | gagatcagac | 900 |
| tggggaaaaa | cacggaaaca | tttagaaaca | atggccttgc | tgaccagatc | tgtgaggact | 960 |
| gtgccttttc | catactccac | ggggaaaact | atgagtctct | ggacctagtt | gccaattcag | 1020 |
| cagatgtggc | aaacatctgg | gtgtctgggt | tacggtacct | ggtttctcga | agtaagcagc | 1080 |
| ctcttgattt | tatggagggc | aaccagaaca | caccacggtt | catgtggttg | aaaacagtgt | 1140 |
| ttgaagcagc | agatgttgat | gggaatggga | ttatgttgga | agacacctct | gtagagttaa | 1200 |
| taaacaact | caaccctact | ctgaaggaag | ccaagatcag | gttaaagttt | aaagaaatcc | 1260 |
| agaagagcaa | ggaaaaacta | accacccgcg | tgaccgaaga | ggaattttgt | gaagcttttt | 1320 |
| gtgaactttg | caccaggcca | gaagtgtatt | tcttacttgt | acagatatct | aaaaacaaag | 1380 |
| aatatttgga | tgccaatgat | ctcatgctct | ttttagaagc | tgagcaagga | gtcacccata | 1440 |
| tcaccgagga | tatatgctta | gacatcataa | ggagatacga | actttctgaa | gagggacgtc | 1500 |
| aaaagggtt | tcttgcaatt | gatggcttta | cccagtattt | attgtcatca | gaatgtgaca | 1560 |
| tttttgatcc | tgagcaaaag | aaggttgccc | aagatatgac | ccagccatta | tctcactact | 1620 |
| atatcaatgc | ctctcataac | acctatctaa | tagaagacca | gttcaggggg | ccagctgaca | 1680 |
| tcaatgggta | cattagagct | ttgaaaatgg | gctgtcgaag | cgttgaactc | gatgtaagtg | 1740 |
| atggttcaga | taatgaacca | atcctttgta | atcgaaataa | catgacaacc | catgtttcct | 1800 |
| ttcgaagtgt | catagaggta | ataaataaat | ttgcctttgt | tgcttctgaa | tacccactca | 1860 |
| ttctttgctt | gggaaatcac | tgctccttgc | cgcagcagaa | ggtaatggct | caacagatga | 1920 |
| aaaaggtctt | tggcaataaa | ctctatactg | aagcaccttt | gccctcagaa | tcctacctcc | 1980 |
| catcaccaga | aaaattaaaa | agaatgatca | ttgtgaaagg | aaagaagttg | ccttctgatc | 2040 |
| cagatgtgtt | agaaggagaa | gtaacagatg | aagatgaaga | agctgaaatg | tctcgaagga | 2100 |
| tgtcggtaga | ttacaatggt | gagcagaagc | aaatccgact | ctgtagggag | ctctctgatt | 2160 |
| tggtgtctat | ttgtaaatct | gttcaataca | gggattttga | actatctatg | aaaagccaaa | 2220 |

```
actattggga aatgtgttca tttagtgaaa cagaggccag ccgcattgca aatgagtacc   2280
cagaggattt tgttaattat aataagaagt tcttatcaag aatctatcca agtgccatga   2340
ggatcgattc cagtaacttg aatccacagg acttttggaa ttgtggctgt cagattgtag   2400
caatgaattt tcagactccg ggtccaatga tggaccttca cacgggctgg tttcttcaaa   2460 acggggatg tggttatgtt ctaaggccgt ctataatgcg agatgaagtt tcttacttca   2520
gcgcaaatac aaagggcatt ctacctgggg tgtctcctct agctcttcat atcaagatca   2580
tcagtggtca gaatttccca aagcccaagg gagcttgtgc caagggggat gtcatagatc   2640
cctatgtttg tatagagata cacggaattc cagcggattg ttcggaacaa agaactaaaa   2700
ctgtacagca aaacagtgat aatcctattt ttgatgaaac ttttgagttc caagtaaacc   2760
tacctgagct ggccatgatc cgttttgttg ttctggatga tgactacatt ggggatgagt   2820 ttataggca atacgata ccatttgaat gtttgcagcc tggatatcgg catgttcccc   2880
tgcgttcttt tgtgggtgac atcatggagc acgtaaccct ttttgtccac atagcaataa   2940
ctaatcgaag tggaggagga aaggcacaga agcgcagtct ttcagtgaga atggggaaga   3000
aagttcggga atataccatg ctcaggaata tcggtcttaa aaccattgat gacatcttta   3060
aaatagcggt tcatccatta cgagaagcca tagatatgag agaaaatatg cagaatgcaa   3120
tcgtgtctat taaggaacta tgtggactcc ctccaattgc cagtctgaag cagtgcctgt   3180
taactctgtc atctcggctc atcaccagtg acaatactcc ttcagtctca cttgtgatga   3240
aagacagctt tccttacctg gagcctctgg gtgcaattcc agatgtgcag aaaaagatgc   3300
tgactgctta tgatctgatg attcaagaga gccggtttct catagaaatg gcggacacag   3360
tccaggaaaa gattgtacag tgtcagaaag cagggatgga gttccatgaa gaacttcata   3420 atttggggc aaaagaaggc ttgaagggaa gaaaactcaa caaagcaact gagagctttg   3480
cttggaacat tacagtattg aagggccaag gagatctgtt gaagaatgcc aagaatgaag   3540
ctatagaaaa catgaagcag atccagctgg catgcctgtc ctgtggactg agtaaagccc   3600
ccagcagcag tgctgaggcc aagagcaagc gcagcctgga agccatagag gagaaggaaa   3660
gtagtgagga gaatgggaag ctgtgactct gggcattatc gacacgttca cccatcttat   3720
caaggactct ggtttctcat tcttgttttc tttcttaaa tgttttataa gttcacaaaa   3780 tggtgccta tatgggtat tggacataga tattttcaca atgtcagtat ttcagtgtag   3840
ttaatttatc taaattaaag cctttagtat cagtgtttta aattctgaga catgtgtcaa   3900 caccctgtg tggatgcctg tggaagagtg tgtgtgtgtg tgtgtgtgtg tgtgtgtggc   3960
agagagagag aaagagagag agagagagaa attctgttaa aatctattct gtgttgcatt   4020
attcatttag tgagttattc cttgatcatt ttgggacaat tgttttaatc tgaaattcta   4080
aagagcactt actgtaacct gttgctgtgt ttaatttgac ttctctgcct ttgacattta   4140
atttagtgat cttagcatag cttattattg aaggaagcca aatttatcaa agcatagatg   4200
ttttggtaga ttaaatatag attagaaaaa ttcctaagaa tcagagtaga aataaaagtg   4260
aatgaaagat taaacagatg atgagaattt ctaaaaagat tagcaaggtc atttcttcag   4320
tcagaaaact ttaaaaaata tttattaaat aaaatcaatt tttaggaagt tttctgtagt   4380
catttactaa acatatgatt tcactagaaa agctgatcat aagtgaattt ataccatacct   4440 gtgtggtact ctgaaacaca ctgaaagctc tgttgcaatt aggatttga tgtgacaata   4500 atattgttgt ataatttcga gatttgtagg aaggtctcat tcttccaagc tgagagtcta   4560
gcactcattt tctataacag atatggcagc ttagaggtgt tggctttgtt tggatgtaat   4620
```

```
ttagggtact aaatttaaat ttaaagatat tgttcaaaca atatcatatc atcacattga   4680
gctgatataa attctgtggg tccgataata tctttgtgat aatttaagag ctaaccagtt   4740
accacacatc tatgatataa ccctaacaca cacagaaaag catacatgca aaaagaaatg   4800
actaattagg gtacatttat aattgcatct aggtaatttt taccctaatg tcttcataaa   4860
gtacttgagt gtaatgtttg ttacctccaa cagaactaaa tgttctatgg ttatgaaaga   4920
atatatttat ttaaagcatt gcttttattt tgaaaagctt cttaattaat ttgattaaca   4980
aatatgctaa tttggggaaa cctagagaag ataattgttg aaattttgca aatataaaca   5040
tctcctatag cttctgtgtt atttctgact tcttaacact attatgttta tgttgcacat   5100
tactgaaaga gtaaagatat gaaaaaaaca cttattgttt tcttttattg tgaattgaaa   5160
aagcaaagct aatgaaaatg ggttactaca tcaaaaatat cttaaagagt ttgctatttc   5220
catggaccag atatgatgaa attattccct gggtttaaaa ctgggcactc gaggaggagg   5280
tacctgaagt catttgaagg caagtttcca atgatgctac aatggcctga aaaaatttct   5340
ttaccctctg ttatatttaa cttgctggta ggaggaatag tggaatgcag gtgttaagcc   5400
cttttgtggtg aaaaagaggt tctatagaca gaaacaaaac ccaccttaca tcagctgatt   5460
ggttgatttt actagtgtac ctcttcatct acttgaattc tatttggtaa atccatgtct   5520
ttactggata tacagttagg tgggaagagg agataaagga tgacaaactc tcaaacaata   5580
tttatacatt tatttactcc agggtcaaat ccaatccttg gaagtagctt ctctagttta   5640
ttttatttgt cccagagctc tactcacact taggacccac ccaaaaattc tcaaaaacgt   5700
aatatggatt ctgcctcatc tgatgctatt tctggcagtg ggttgtcagc catactctgc   5760
ttcattccac tgggtgtcct tgctagatgg ggagtgagat gtggagcagg gaggagcttt   5820
ggattctggg agtggaggtg gcaagggaaa agtctcctag tctcctgtga tgttcctgcc   5880
tccagataga atagcaaaaa caaacaattt ttttttgtgt attatgcctc catgacattg   5940
ttacattcta tgaggagcat ctgtctcctt tctagacttg aactgtggta gaaaaagccc   6000
ccttctctct tctatctact tagatttggt gatgctagga atgtagtgtt ttagatatta   6060
attctatttt tatttattca tttttacatc accaatagga tctgaggtgg agatggcggg   6120
tattatcact ggcattttac aggtgagaaa gcccaaagcc actgaggtaa ttaatggaat   6180
aattgatttt gaacttgggt ctgtctgatt tcatgtgcaa gattatatac ttagtgattt   6240
tgattttaag tttattctta acatttaaaa ccagactatt aactcttacc tttataacca   6300
cagatacaaa gaactgtatc atttatttc tgaatataaa atattaatgg tcaatataaa   6360
aatacaaaaa tagagaacta tatacaacag aaaagcaaaa ttacccacta ataacatttt   6420
gatttatatc cctttagaca ctgtttagag tttatacata tatgtaaata tgcttgtatt   6480
ttaacaaaat tgagatatta tataaactgt ttgtagcagg gtgtttaaaa ttttaacaat   6540
atgttatgga tatctttctg tgtcaataaa tgtgtattta cattagagtt ccaagcattt   6600
gaactgaa                                                             6608
```

<210> SEQ ID NO 5
<211> LENGTH: 4691
<212> TYPE: DNA
<213> ORGANISM: Homo sapiens

<400> SEQUENCE: 5

```
gtcagtctgg ccggctccgt cctcccgtag gctccgctgt agctagcaat gtgacaccag     60
gacgcactcg ctctcgcgcg ctctcccagg ctcgttctcc ctcgccctct ctctctcaca    120
```

```
cacgcacgca cacacccacc tctcccataa acacacacac acacatgcac acccacaccc    180
acgcgcgccc gcaccgcccc acgcgcacac actcctgccc acgcccacgc agcgctccgg    240
gaagtccggt ccgggcgaga gcgcgaaagg ataccgagaa gccacccgcg gagagcgcag    300
cggcgccctg ggacgcggcg ctctcccggc gctgctgcct cggcttggtc tcggcctgcg    360
ggccgtcggc cggcgatggc cctggattat ctactactgc tcctcctggc atccgcagtg    420
gctgcgatgg aagaaacgtt aatggacacc agaacggcta ctgcagagct gggctggacg    480
gccaatcctg cgtccgggtg ggaagaagtc agtggctacg atgaaaacct gaacaccatc    540
cgcacctacc aggtgtgcaa tgtcttcgag cccaaccaga caattggct gctcaccacc    600 ttcatcaacc gcggggggc ccatcgcatc tacacagaga tgcgcttcac tgtgagagac    660
tgcagcagcc tccctaatgt cccaggatcc tgcaaggaga ccttcaactt gtattactat    720
gagactgact ctgtcattgc caccaagaag tcagccttct ggtctgaggc cccctacctc    780
aaagtagaca ccattgctgc agatgagagc ttctcccagg tggactttgg gggaaggctg    840
atgaaggtaa acacagaagt caggagcttt gggcctctta ctcggaatgg ttttacctc    900 gcttttcagg attatggagc ctgtatgtct cttctttctg tccgtgtctt cttcaaaaag    960
tgtcccagca ttgtgcaaaa ttttgcagtg tttccagaga ctatgacagg ggcagagagc    1020
acatctctgg tgattgctcg gggcacatgc atccccaacg cagaggaagt ggacgtgccc    1080
atcaaactct actgcaacgg ggatgggaa tggatggtgc ctattgggcg atgcacctgc    1140
aagcctggct atgagcctga aacagcgtg gcatgcaagg cttgccctgc agggacattc    1200
aaggccagcc aggaagctga aggctgctcc cactgcccct ccaacagccg ctcccctgca    1260
gaggcgtctc ccatctgcac ctgtcggacc ggttattacc gagcggactt tgaccctcca    1320
gaagtggcat gcactagcgt cccatcaggt ccccgcaatg ttatctccat cgtcaatgag    1380
acgtccatca ttctggagtg gcaccctcca agggagacag gtgggcggga tgatgtgacc    1440
tacaacatca tctgcaaaaa gtgccgggca gaccgccgga gctgctcccg ctgtgacgac    1500
aatgtggagt ttgtgcccag gcagctgggc ctgacggagt gccgcgtctc catcagcagc    1560
ctgtgggccc acaccccta cacctttgac atccaggcca tcaatggagt ctccagcaag    1620
agtcccttcc ccccacagca cgtctctgtc aacatcacca caaaccaagc cgcccccctcc    1680 accgttccca tcatgcacca agtcagtgcc actatgagga gcatcacctt gtcatggcca    1740
cagccggagc agcccaatgg catcatcctg gactatgaga tccggtacta tgagaaggaa    1800
cacaatgagt tcaactcctc catggccagg agtcagacca acacagcaag gattgatggg    1860
ctgcggcctg gcatggtata tgtggtacag gtgcgtgccc gcactgttgc tggctacggc    1920
aagttcagtg gcaagatgtg cttccagact ctgactgacg atgattacaa gtcagagctg    1980
agggagcagc tgcccctgat tgctggctcg gcagcggccg gggtcgtgtt cgttgtgtcc    2040
ttggtggcca tctctatcgt ctgtagcagg aaacggctt atagcaaaga ggctgtgtac    2100
agcgataagc tccagcatta cagcacaggc gaggctccc cagggatgaa gatctacatt    2160 gacccctca cttacgagga tcccaacgaa gctgtccggg agtttgccaa ggagattgat    2220
gtatcttttg tgaaaattga agaggtcatc ggagcagggg agtttggaga agtgtacaag    2280
gggcgtttga aactgccagg caagagggaa atctacgtgg ccatcaagac cctgaaggca    2340
gggtactcgg agaagcagcg tcgggacttt ctgagtgagg cgagcatcat gggccagttc    2400
gaccatccta acatcattcg cctggagggt gtggtcacca agagtcggcc tgtcatgatc    2460
atcacagagt tcatggagaa tggtgcattg gattctttcc tcaggcaaaa tgacgggcag    2520
```

```
ttcaccgtga tccagcttgt gggtatgctc aggggcatcg ctgctggcat gaagtacctg    2580
gctgagatga attatgtgca tcgggacctg gctgctagga acattctggt caacagtaac    2640
ctggtgtgca aggtgtccga ctttggcctc tcccgctacc tccaggatga cacctcagat    2700
cccacctaca ccagctcctt gggagggaag atccctgtga gatggacagc tccagaggcc    2760
atcgcctacc gcaagttcac ttcagccagc gacgtttgga gctatgggat cgtcatgtgg    2820
gaagtcatgt catttggaga gagaccctat tgggatatgt ccaaccaaga tgtcatcaat    2880
gccatcgagc aggactaccg gctgccccca cccatggact gtccagctgc tctacaccag    2940
ctcatgctgg actgttggca aggaccggg aacagccggc cccggtttgc ggagattgtc    3000
aacaccctag ataagatgat ccggaacccg gcaagtctca agactgtggc aaccatcacc    3060
gccgtgcctt cccagcccct gctcgaccgc tccatcccag acttcacggc ctttaccacc    3120
gtggatgact ggctcagcgc catcaaaatg gtccagtaca gggacagctt cctcactgct    3180
ggcttcacct ccctccagct ggtcacccag atgcatcag aagacctcct gagaataggc    3240
atcaccttgg caggccatca gaagaagatc ctgaacagca ttcattctat gagggtccag    3300
ataagtcagt caccaacggc aatggcatga gaactcttgt ttcttgggga aggagaggag    3360
ggaaaaggac cagggtcaag ggggaccaga ggttgaccac tgtggaatgt actggagaga    3420
ctggcttctc agctgaggaa tgcatttcca tcagtgaaga atcaaccgga cctgttgcta    3480
gcaggcaatc tccatttctc agtgacagaa gcatgtttga gatgccgtgg gaaaccaaat    3540
atataataat aaaaatataa aaaggtgatg ttcaacagaa gtgaagacaa acaatatgc    3600 atcaggagaa caagagtaaa cccagctccc actctcagtg ggctgcagtt gcccaaccac    3660
aggaagaaag ggaaggaggt agagggaaga aacagaagca gtgttccatt ttcttcctca    3720
ccaatgacat tcttttcttt tctcctttcg tactcctccc tgagagtccc ctccctttctc   3780 ccacactcgt ttccctttgc tcatgactcc tgtaggaag tttcttcaaa caaaacccag    3840
ctcctgagtc tccagatgtt gttctgtcag ttgccaaagg actttgctga ccactgcatg    3900
gggatccaac caattcaatt aatgtcttca tattgaagaa gagatgtacc ttcaattgaa    3960
aacctcgttt ttcttttgtt tgcatttcct gcaaaaagga aaagaaacc acaaattggg    4020 gaaaaaaaa aagaaaaac ctgtttccgt gtgcaaaagc acacatatgt atgtctgtgt     4080
tataaaatga ctgtgcttgt tcgtaacaga tgcaaacaag aaagaagaac tgggaagtct    4140
ttgtccctag gaaatccaaa ggggctggaa tatggtgttg gtttggcttt ctggttggcc    4200
caatcggcct attggctcaa tgggaagaga ggagagggag aaaaataaaa tgaaaggaaa    4260
aaaaaaagtt tgcaaattca gacaggaaac aggtgagtgg tttgaattgg atgcagtgtg    4320
ggccatcctg gaatgatact gactgattaa ttattcctga taacatctca agaaaggag    4380 aaggaaagtg tttctggaga atgttctttc acatcactgg aatctgcaat tcaagaagtg    4440
acaagggaga attcttgctt tacctatgga ctggcttaag ccgtgtggca tccgaggaat    4500
gtttcaaatg tgtctgtgtt tctctttaca ttccttgttg tacctcattg ttcaattcac    4560
ttttgtaaat tccacctaac atttaattat tttaaatttc tccttttacc ttaatctcct    4620
tgctaatttt atctgtctaa ttaaaagag cagaagcatg tctgggttta cgtaaaaaaa    4680 aaaaaaaaa a                                                          4691

<210> SEQ ID NO 6
<211> LENGTH: 1888
<212> TYPE: DNA
<213> ORGANISM: Homo sapiens
```

<400> SEQUENCE: 6

```
ttagaagctc tgagaaatca tgggccgtgc ggtaggggtt gaaatgctca aaggtccaca      60
cttcttgaaa taaacagaat ggtcttgagt ggattgcaac tgttttggaa atagctttgt     120
gaaaagaggg tggagagcta ctcaaaattc tacgttagag agactgaaaa gacatctaat     180
ttcattgctc ggcagactgc tctccagaat gttgagattg cccgagaagt gaccccagca     240
aaagaaaaat attgctgtac ctaaattcaa acgacatcct tgtggtgcc acagcacatg      300
gatttcagaa ccgcctgtga ggagacaaag acaggaattt gtttgctgca ggatggtaac     360
caggagcctt tcaaagtgcg gctgcaccta gccaaagaca ttttgatgat ccaggaacag     420
gatgtgatat gtgtgtctgg tgagcctttc tattctggtg aaagaacggt gaccatcaga     480
agacaaacag taggaggatt tggattaagc ataaaggggag gagcagaaca taacattcca    540
gttgtcgttt caaaaatctc caaggaacaa agagcggaac tttcaggact acttttatt     600
ggagatgcaa ttctacagat aaatggcatt aatgtgagaa aatgtagaca tgaagaagtg     660
gttcaggttc ttcggaatgc tggagaagag tgactctaac agtgtcattt ttaaaaagag     720
cacctgcttt cctcaaactc ccattgaatg aagattgtgc atgtgctcca agtgaccaga     780
gcagtggcac ctcctctcct ctctgtgaca gtggcttaca tctcaactac catcccaaca     840
atacagacac attatcatgc tcgtcgtggc cgacgtctcc aggcttgagg tgggagaagc     900
gatggtgcga cctcagactg atccctctac ttcattcgcg cttctctcag tatgtgcccg     960
gcacagattt gagtcggcag aatgcctttc aagtcattgc tgtggatggg gtctgcactg    1020
ggattattca gtgcctctct gctgaagact gcgttgactg gctacaagca atagcaacta    1080
acatttcaaa tctcacaaag cacaatatta aaaaaatcaa cagaaacttt cctgtaaacc    1140
agcagattgt ctacatgggc tggtgtgaag cccgggagca agacccctc caggacagag     1200
tgtactcccc gaccttcctg gccctgaggg gctcatgtct ctacaagttt ctggcacctc    1260
cagtgaccac ctgggactgg acgagagcag agaaaacatt ctcagtttat gagattatgt    1320
gcaagatcct caaggacagt gacctgctgg accgacggaa acagtgcttc accgtgcagt    1380
ctgagtctgg ggaggacctg tacttctcag tggagctgga aagtgacctc gcccagtggg    1440
aaagagcctt ccagacagca acctttctag aagtagaacg gatacagtgc aagacctatg    1500
catgtgtgct agaaagtcat ctaatgggac tcacaattga tttcagcaca ggatttatct    1560
gctttgatgc tgcaacaaag gctgtccttt ggaggtataa attctctcag cttaaaggtt    1620
cttcagatga tggcaagagc aaaatcaaat ttttgtttca gaatccagat actaaacaga    1680
ttgaagcaaa ggagttggaa ttttctaatt tatttgctgt tcttcactgc attcattcct    1740
tctttgctgc caaggtagct tgtttggacc ctctatttt aggcaatcaa gctactgctt     1800
ctactgctgc cagctctgct accacgagca aagcaaagta caacttga catactgaac      1860
tcttcattga cacaccccat gactgtat                                       1888
```

<210> SEQ ID NO 7
<211> LENGTH: 2541
<212> TYPE: DNA
<213> ORGANISM: Homo sapiens

<400> SEQUENCE: 7

```
tccaggctca tttgcttcca cctagcttcg gtgccccctg ctaggcgggg accctcgaga      60
gcgatgccga tggatttgat tttagttgtg tggttctgtg tgtgcactgc caggacagtg     120
gtgggctttg ggatggaccc tgaccttcag atggatatcg tcaccgagct tgaccttgtg     180
```

-continued

```
aacaccaccc ttggagttgc tcaggtgtct ggaatgcaca atgccagcaa agcattttta    240
tttcaagaca tagaaagaga gatccatgca gctcctcatg tgagtgagaa attaattcag    300
ctgttccgga acaagagtga attcaccatt ttggccactg tacagcagaa gccatctact    360
tcaggagtga tactgtccat tcgagaactg gagcacagct attttgaact ggagagcagt    420
ggcctgaggg atgagattcg gtatcactac atacacaatg gaagccaag gacagaggca    480 cttccttacc gcatggcaga tggacaatgg cacaaggttg cactgtcagt tagcgcctct    540
catctcctgc tccatgtcga ctgtaacagg atttatgagc gtgtgataga ccctccagat    600
accaaccttc ccccaggaat caatttatgg cttggccagc gcaaccaaaa gcatggctta    660
ttcaaaggga tcatccaaga tgggaagatc atctttatgc cgaatggata taacacag     720 tgtccaaatc taaatcacac ttgcccaacc tgcagtgatt tcttaagcct ggtgcaagga    780
ataatggatt tacaagagct tttggccaag atgactgcaa aactaaatta tgcagagaca    840
agacttagtc aattggaaaa ctgtcattgt gagaagactt gtcaagtgag tggactgctc    900
tatcgagatc aagactcttg ggtagatggt gaccattgca ggaactgcac ttgcaaaagt    960
ggtgccgtgg aatgccgaag gatgtcctgt cccccctctca attgctcccc agactccctc   1020
ccagtgcaca ttgctggcca gtgctgtaag gtctgccgac caaaatgtat ctatggagga   1080
aaagttcttg cagaaggcca gcggatttta accaagagct gtcgggaatg ccgaggtgga   1140
gttttagtaa aaattacaga aatgtgtcct cctttgaact gctcagaaaa ggatcacatt   1200
cttcctgaga atcagtgctg ccgtgtctgt agaggtcata acttttgtgc agaaggacct   1260
aaatgtggtg aaaactcaga gtgcaaaaac tggaatacaa aagctacttg tgagtgcaag   1320
agtggttaca tctctgtcca gggagactct gcctactgtg aagatattga tgagtgtgca   1380
gctaagatgc attactgtca tgccaatact gtgtgtgtca accttcctgg gttatatcgc   1440
tgtgactgtg tcccaggata cattcgtgtg gatgacttct cttgtacaga acacgatgaa   1500
tgtggcagcg gccagcacaa ctgtgatgag aatgccatct gcaccaacac tgtccaggga   1560
cacagctgca cctgcaaacc gggctacgtg gggaacggga ccatctgcag agctttctgt   1620
gaagagggct gcagatacgg tggaacgtgt gtggctccca acaaatgtgt ctgtccatct   1680
ggattcacag gaagccactg cgagaaagat attgatgaat gttcagaggg aatcattgag   1740
tgccacaacc attcccgctg cgttaacctg ccagggtggt accactgtga gtgcagaagc   1800 ggttccatg acgatgggac ctattcactg tccggggagt cctgtattga cattgatgaa   1860
tgtgccttaa gaactcacac ctgttggaac gattctgcct gcatcaacct ggcagggggt   1920
tttgactgtc tctgcccctc tgggccctcc tgctctggtg actgtcctca tgaaggggg   1980 ctgaagcaca atgccaggt gtggaccttg aaagaagaca ggtgttctgt ctgctcctgc   2040
aaggatggca agatattctg ccgacggaca gcttgtgatt gccagaatcc aagtgctgac   2100
ctattctgtt gcccagaatg tgacaccaga gtcacaagtc aatgtttaga ccaaaatggt   2160
cacaagctgt atcgaagtgg agacaattgg acccatagct gtcagcagtg tcggtgtctg   2220
gaaggagagg tagattgctg gccactcact tgccccaact tgagctgtga gtatacagct   2280
atcttagaag gggaatgttg tccccgctgt gtcagtgacc cctgcctagc tgataacatc   2340
acctatgaca tcagaaaaac ttgcctggac agctatggtg tttcacggct tagtggctca   2400
gtgtggacga tggctggatc tccctgcaca acctgtaaat gcaagaatgg aagagtctgt   2460
tgttctgtga ttttgagtg tcttcaaaat aattgaagta tttacagtgg actcaacgca   2520
gaagaatgga cgaaatgacc a                                             2541
```

<210> SEQ ID NO 8
<211> LENGTH: 3422
<212> TYPE: DNA
<213> ORGANISM: Homo sapiens

<400> SEQUENCE: 8

```
ccccgacgga gccgcgccgg ggcgagtccg acccctccct ccgggccccc tccgggccgc      60
gctgccgcct cggccctgcg tgtgggaatg atgtgcgcat tggagggtct aagttcttca     120
cgcgcctggg gaggcctccc ttttctttct taggcaacca agcgtatta atcctactga      180 tcagtaaatc cgaggcagca gcaggagaga caaacgttat tttcccgctt gattccaaga    240
acctcttcga ttttatttt tattttaaa gagggagacg atggactgag ctgatccgca      300
ccatggagtc tcgggtctta ctgagaacat tctgtttgat cttcggtctc ggagcagttt    360 ggggcttgg tgtggaccct tccctacaga ttgacgtctt aacagagtta gaacttgggg     420
agtccacgac cggagtgcgt caggtccgg ggctgcataa tgggacgaaa gcctttctct     480
ttcaagatac tcccagaagc ataaaagcat ccactgctac agctgaacag ttttttcaga    540
agctgagaaa taaacatgaa tttactattt tggtgaccct aaaacagacc cacttaaatt    600
caggagttat tctctcaatt caccacttgg atcacaggta cctggaactg aaagtagtg     660 gccatcggaa tgaagtcaga ctgcattacc gctcaggcag tcaccgccct cacacagaag    720
tgtttcctta cattttggct gatgacaagt ggcacaagct ctccttagcc atcagtgctt    780
cccatttgat tttacacatt gactgcaata aaatttatga aagggtagta gaaaagccct    840
ccacagactt gcctctaggc acaacatttt ggctaggaca gagaaataat gcgcatggat    900
attttaaggg tataatgcaa gatgtccaat tacttgtcat gccccaggga tttattgctc    960
agtgcccaga tcttaatcgc acctgtccaa cttgcaatga cttccatgga cttgtgcaga   1020
aaatcatgga gctacaggat attttagcca aacatcagc caagctgtct cgagctgaac    1080
agcgaatgaa tagattggat cagtgctatt gtgaaaggac ttgcaccatg aagggaacca    1140
cctaccgaga atttgagtcc tggatagacg gctgtaagaa ctgcacatgc ctgaatggaa    1200
ccatccagtg tgaaactcta atctgcccaa atcctgactg cccacttaag tcggctcttg    1260
cgtatgtgga tggcaaatgc tgtaaggaat gcaaatcgat atgccaattt caaggacgaa    1320
cctactttga aggagaaaga aatacagtct attcctcttc tggagtatgt gttctctatg    1380
agtgcaagga ccagaccatg aaacttgttg agagttcagg ctgtccagct ttggattgtc    1440
cagagtctca tcagataacc ttgtctcaca gctgttgcaa agtttgtaaa ggttatgact    1500
tttgttctga aaggcataac tgcatggaga attccatctg cagaaatctg aatgacaggg    1560
ctgtttgtag ctgtcgagat ggttttaggg ctcttcgaga ggataatgcc tactgtgaag    1620
acatcgatga gtgtgctgaa gggcgccatt actgtcgtga aaatacaatg tgtgtcaaca    1680
ccccgggttc tttatgtgc atctgcaaaa ctggatacat cagaattgat gattattcat     1740
gtacagaaca tgatgagtgt atcacaaatc agcacaactg tgatgaaaat gctttatgct    1800
tcaacactgt tggaggacac aactgtgttt gcaagccggg ctatacaggg aatggaacga    1860
catgcaaagc attttgcaaa gatggctgta gaaatggagg agcctgtatt gccgctaatg    1920
tgtgtgcctg cccacaaggc ttcactggac ccagctgtga acggacatt gatgaatgct    1980 ctgatggttt tgttcaatgt gacagtcgtg ctaattgcat taacctgcct ggatggtacc    2040
actgtgagtg cagagatggc taccatgaca atggatgtt tcaccaagt ggagaatcgt     2100 gtgaagatat tgatgagtgt gggaccggga ggcacagctg tgccaatgat accatttgct    2160
```

```
tcaatttgga tggcggatat gattgtcgat gtcctcatgg aaagaattgc acaggggact   2220
gcatccatga tggaaaagtt aagcacaatg gtcagatttg ggtgttggaa atgacaggt    2280 gctctgtgtg ctcatgtcag aatggattcg ttatgtgtcg acggatggtc tgtgactgtg   2340
agaatcccac agttgatctt ttttgctgcc ctgaatgtga cccaaggctt agtagtcagt   2400
gcctccatca aatgggaaa actttgtata acagtggtga cacctgggtc cagaattgtc    2460
aacagtgccg ctgcttgcaa ggggaagttg attgttggcc cctgccttgc ccagatgtgg   2520
agtgtgaatt cagcattctc ccagagaatg agtgctgccc gcgctgtgtc acagaccctt   2580
gccaggctga caccatccgc aatgacatca ccaagacttg cctggacgaa atgaatgtgg   2640
ttcgcttcac cgggtcctct tggatcaaac atggcactga gtgtactctc tgccagtgca   2700
agaatggcca catctgttgc tcagtggatc cacagtgcct tcaggaactg tgaagttaac   2760
tgtctcatgg gagatttctg ttaaaagaat gttctttcat aaaagacca aaaagaagtt    2820 aaaacttaaa ttgggtgatt tgtgggcagc taaatgcagc tttgttaata gctgagtgaa   2880
ctttcaatta tgaaatttgt ggagcttgac aaaatcacaa aaggaaaatt actggggcaa   2940 aattagaccct caagtctgcc tctactgtgt ctcacatcac catgtagaag aatgggcgta   3000
cagtatatac cgtgacatcc tgaaccctgg atagaaagcc tgagcccatt ggatctgtga   3060
aagcctctag cttcactggt gcagaaaatt ttcctctaga tcagaatctt caagaatcag   3120
ttaggttcct cactgcaaga aataaaatgt caggcagtga atgaattata ttttcagaag   3180
taaagcaaag aagctataac atgttgtgta cagtacactc tgaaaagaaa tctgaaacaa   3240
gttattgtaa tgataaaaat aatgcacagg catggttact taatatttc taacaggaaa    3300 agtcatccct atttccttgt tttactgcac ttaatattat ttggttgaat tgttcagta    3360 taagctcgtt cttgtgcaaa attaaataaa tatttctctt accttataaa aaaaaaaaa    3420 aa                                                                  3422
```

<210> SEQ ID NO 9
<211> LENGTH: 171
<212> TYPE: PRT
<213> ORGANISM: Homo sapiens

<400> SEQUENCE: 9

```
Met Leu His Ala Arg Cys Cys Leu Asn Gln Lys Gly Thr Ile Leu Gly
1               5                   10                  15

Leu Asp Leu Gln Asn Cys Ser Leu Glu Asp Pro Gly Pro Asn Phe His
            20                  25                  30

Gln Ala His Thr Thr Val Ile Ile Asp Leu Gln Ala Asn Pro Leu Lys
        35                  40                  45

Gly Asp Leu Ala Asn Thr Phe Arg Gly Phe Thr Gln Leu Gln Thr Leu
    50                  55                  60

Ile Leu Pro Gln His Val Asn Cys Pro Gly Gly Ile Asn Ala Trp Asn
65                  70                  75                  80

Thr Ile Thr Ser Tyr Ile Asp Asn Gln Ile Cys Gln Gly Gln Lys Asn
                85                  90                  95

Leu Cys Asn Asn Thr Gly Asp Pro Glu Met Cys Pro Glu Asn Gly Ser
            100                 105                 110

Cys Val Pro Asp Gly Pro Gly Leu Leu Gln Cys Val Cys Ala Asp Gly
        115                 120                 125

Phe His Gly Tyr Lys Cys Met Arg Gln Gly Ser Phe Ser Leu Leu Met
    130                 135                 140
```

```
Phe Phe Gly Ile Leu Gly Ala Thr Thr Leu Ser Val Ser Ile Leu Leu
145                 150                 155                 160

Trp Ala Thr Gln Arg Arg Lys Ala Lys Thr Ser
                165                 170
```

<210> SEQ ID NO 10
<211> LENGTH: 284
<212> TYPE: PRT
<213> ORGANISM: Homo sapiens

<400> SEQUENCE: 10

```
Met Lys Thr Ser Ala Glu Leu His Glu Gln Glu Lys Pro Pro Ser Ser
1               5                   10                  15

Pro Arg Ala Thr Gly Pro Gly Arg Leu Gly His Ala Arg Gly Arg Gly
            20                  25                  30

Pro Asp Ala Leu Arg Gly Gly Ala Ala Gly Pro Gly Arg Ala Ser Ser
            35                  40                  45

Gly Ala Pro Arg Glu Arg Lys Met Ala Pro His Asp Pro Gly Ser Leu
50                  55                  60

Thr Thr Leu Val Pro Trp Ala Ala Ala Leu Leu Leu Ala Leu Gly Val
65                  70                  75                  80

Glu Arg Ala Leu Ala Leu Pro Glu Ile Cys Thr Gln Cys Pro Gly Ser
                85                  90                  95

Val Gln Asn Leu Ser Lys Val Ala Phe Tyr Cys Lys Thr Thr Arg Glu
            100                 105                 110

Leu Met Leu His Ala Arg Cys Cys Leu Asn Gln Lys Gly Thr Ile Leu
        115                 120                 125

Gly Leu Asp Leu Gln Asn Cys Ser Leu Glu Asp Pro Gly Pro Asn Phe
130                 135                 140

His Gln Ala His Thr Thr Val Ile Ile Asp Leu Gln Ala Asn Pro Leu
145                 150                 155                 160

Lys Gly Asp Leu Ala Asn Thr Phe Arg Gly Phe Thr Gln Leu Gln Thr
                165                 170                 175

Leu Ile Leu Pro Gln His Val Asn Cys Pro Gly Gly Ile Asn Ala Trp
            180                 185                 190

Asn Thr Ile Thr Ser Tyr Ile Asp Asn Gln Ile Cys Gln Gly Gln Lys
        195                 200                 205

Asn Leu Cys Asn Asn Thr Gly Asp Pro Glu Met Cys Pro Glu Asn Gly
210                 215                 220

Ser Cys Val Pro Asp Gly Pro Gly Leu Leu Gln Cys Val Cys Ala Asp
225                 230                 235                 240

Gly Phe His Gly Tyr Lys Cys Met Arg Gln Gly Ser Phe Ser Leu Leu
                245                 250                 255

Met Phe Phe Gly Ile Leu Gly Ala Thr Thr Leu Ser Val Ser Ile Leu
            260                 265                 270

Leu Trp Ala Thr Gln Arg Arg Lys Ala Lys Thr Ser
        275                 280
```

<210> SEQ ID NO 11
<211> LENGTH: 229
<212> TYPE: PRT
<213> ORGANISM: Homo sapiens

<400> SEQUENCE: 11

```
Met Ala Pro His Asp Pro Gly Ser Leu Thr Thr Leu Val Pro Trp Ala
1               5                   10                  15

Ala Ala Leu Leu Leu Ala Leu Gly Val Glu Arg Ala Leu Ala Leu Pro
```

-continued

```
                 20                  25                  30
Glu Ile Cys Thr Gln Cys Pro Gly Ser Val Gln Asn Leu Ser Lys Val
             35                  40                  45
Ala Phe Tyr Cys Lys Thr Thr Arg Glu Leu Met Leu His Ala Arg Cys
         50                  55                  60
Cys Leu Asn Gln Lys Gly Thr Ile Leu Gly Leu Asp Leu Gln Asn Cys
 65                  70                  75                  80
Ser Leu Glu Asp Pro Gly Pro Asn Phe His Gln Ala His Thr Thr Val
                 85                  90                  95
Ile Ile Asp Leu Gln Ala Asn Pro Leu Lys Gly Asp Leu Ala Asn Thr
            100                 105                 110
Phe Arg Gly Phe Thr Gln Leu Gln Thr Leu Ile Leu Pro Gln His Val
        115                 120                 125
Asn Cys Pro Gly Gly Ile Asn Ala Trp Asn Thr Ile Thr Ser Tyr Ile
130                 135                 140
Asp Asn Gln Ile Cys Gln Gly Gln Lys Asn Leu Cys Asn Asn Thr Gly
145                 150                 155                 160
Asp Pro Glu Met Cys Pro Glu Asn Gly Ser Cys Val Pro Asp Gly Pro
                165                 170                 175
Gly Leu Leu Gln Cys Val Cys Ala Asp Gly Phe His Gly Tyr Lys Cys
            180                 185                 190
Met Arg Gln Gly Ser Phe Ser Leu Leu Met Phe Phe Gly Ile Leu Gly
        195                 200                 205
Ala Thr Thr Leu Ser Val Ser Ile Leu Leu Trp Ala Thr Gln Arg Arg
    210                 215                 220
Lys Ala Lys Thr Ser
225

<210> SEQ ID NO 12
<211> LENGTH: 1094
<212> TYPE: PRT
<213> ORGANISM: Homo sapiens

<400> SEQUENCE: 12

Met Ala Glu Gly Ala Ala Gly Arg Glu Asp Pro Ala Pro Pro Asp Ala
 1               5                  10                  15
Ala Gly Gly Glu Asp Asp Pro Arg Val Gly Pro Asp Ala Ala Gly Asp
                20                  25                  30
Cys Val Thr Ala Ala Ser Gly Gly Arg Met Arg Asp Arg Arg Ser Gly
             35                  40                  45
Val Ala Leu Pro Gly Ala Ala Gly Thr Pro Ala Asp Ser Glu Ala Gly
         50                  55                  60
Leu Leu Glu Ala Ala Arg Ala Thr Pro Arg Arg Ser Ser Ile Ile Lys
 65                  70                  75                  80
Asp Pro Ser Asn Gln Lys Cys Gly Gly Arg Lys Lys Thr Val Ser Phe
                 85                  90                  95
Ser Ser Met Pro Ser Glu Lys Lys Ile Ser Ser Ala Asn Asp Cys Ile
            100                 105                 110
Ser Phe Met Gln Ala Gly Cys Glu Leu Lys Lys Val Arg Pro Asn Ser
        115                 120                 125
Arg Ile Tyr Asn Arg Phe Phe Thr Leu Asp Thr Asp Leu Gln Ala Leu
    130                 135                 140
Arg Trp Glu Pro Ser Lys Lys Asp Leu Glu Lys Ala Lys Leu Asp Ile
145                 150                 155                 160
Ser Ala Ile Lys Glu Ile Arg Leu Gly Lys Asn Thr Glu Thr Phe Arg
```

```
                    165                 170                 175
Asn Asn Gly Leu Ala Asp Gln Ile Cys Glu Asp Cys Ala Phe Ser Ile
            180                 185                 190

Leu His Gly Glu Asn Tyr Glu Ser Leu Asp Leu Val Ala Asn Ser Ala
        195                 200                 205

Asp Val Ala Asn Ile Trp Val Ser Gly Leu Arg Tyr Leu Val Ser Arg
    210                 215                 220

Ser Lys Gln Pro Leu Asp Phe Met Glu Gly Asn Gln Asn Thr Pro Arg
225                 230                 235                 240

Phe Met Trp Leu Lys Thr Val Phe Glu Ala Ala Asp Val Asp Gly Asn
                245                 250                 255

Gly Ile Met Leu Glu Asp Thr Ser Val Glu Leu Ile Lys Gln Leu Asn
            260                 265                 270

Pro Thr Leu Lys Glu Ala Lys Ile Arg Leu Lys Phe Lys Glu Ile Gln
        275                 280                 285

Lys Ser Lys Glu Lys Leu Thr Thr Arg Val Thr Glu Glu Phe Cys
    290                 295                 300

Glu Ala Phe Cys Glu Leu Cys Thr Arg Pro Glu Val Tyr Phe Leu Leu
305                 310                 315                 320

Val Gln Ile Ser Lys Asn Lys Glu Tyr Leu Asp Ala Asn Asp Leu Met
                325                 330                 335

Leu Phe Leu Glu Ala Glu Gln Gly Val Thr His Ile Thr Glu Asp Ile
            340                 345                 350

Cys Leu Asp Ile Ile Arg Arg Tyr Glu Leu Ser Glu Glu Gly Arg Gln
        355                 360                 365

Lys Gly Phe Leu Ala Ile Asp Gly Phe Thr Gln Tyr Leu Leu Ser Ser
    370                 375                 380

Glu Cys Asp Ile Phe Asp Pro Glu Gln Lys Lys Val Ala Gln Asp Met
385                 390                 395                 400

Thr Gln Pro Leu Ser His Tyr Tyr Ile Asn Ala Ser His Asn Thr Tyr
                405                 410                 415

Leu Ile Glu Asp Gln Phe Arg Gly Pro Ala Asp Ile Asn Gly Tyr Ile
            420                 425                 430

Arg Ala Leu Lys Met Gly Cys Arg Ser Val Glu Leu Asp Val Ser Asp
        435                 440                 445

Gly Ser Asp Asn Glu Pro Ile Leu Cys Asn Arg Asn Met Thr Thr
    450                 455                 460

His Val Ser Phe Arg Ser Val Ile Glu Val Ile Asn Lys Phe Ala Phe
465                 470                 475                 480

Val Ala Ser Glu Tyr Pro Leu Ile Leu Cys Leu Gly Asn His Cys Ser
                485                 490                 495

Leu Pro Gln Gln Lys Val Met Ala Gln Gln Met Lys Lys Val Phe Gly
            500                 505                 510

Asn Lys Leu Tyr Thr Glu Ala Pro Leu Pro Ser Glu Ser Tyr Leu Pro
        515                 520                 525

Ser Pro Glu Lys Leu Lys Arg Met Ile Ile Val Lys Gly Lys Lys Leu
    530                 535                 540

Pro Ser Asp Pro Asp Val Leu Glu Gly Glu Val Thr Asp Glu Asp Glu
545                 550                 555                 560

Glu Ala Glu Met Ser Arg Arg Met Ser Val Asp Tyr Asn Gly Glu Gln
                565                 570                 575

Lys Gln Ile Arg Leu Cys Arg Glu Leu Ser Asp Leu Val Ser Ile Cys
            580                 585                 590
```

-continued

Lys Ser Val Gln Tyr Arg Asp Phe Glu Leu Ser Met Lys Ser Gln Asn
            595                 600                 605

Tyr Trp Glu Met Cys Ser Phe Ser Glu Thr Glu Ala Ser Arg Ile Ala
610                 615                 620

Asn Glu Tyr Pro Glu Asp Phe Val Asn Tyr Asn Lys Lys Phe Leu Ser
625                 630                 635                 640

Arg Ile Tyr Pro Ser Ala Met Arg Ile Asp Ser Ser Asn Leu Asn Pro
            645                 650                 655

Gln Phe Trp Asn Cys Gly Cys Gln Ile Val Ala Met Asn Phe Gln Thr
            660                 665                 670

Pro Gly Pro Met Met Asp Leu His Thr Gly Trp Phe Leu Gln Asn Gly
            675                 680                 685

Gly Cys Gly Tyr Val Leu Arg Pro Ser Ile Met Arg Asp Glu Val Ser
            690                 695                 700

Tyr Phe Ser Ala Asn Thr Lys Gly Ile Leu Pro Gly Val Ser Pro Leu
705                 710                 715                 720

Ala Leu His Ile Lys Ile Ile Ser Gly Gln Asn Phe Pro Lys Pro Lys
            725                 730                 735

Gly Ala Cys Ala Lys Gly Asp Val Ile Asp Pro Tyr Val Cys Ile Glu
            740                 745                 750

Ile His Gly Ile Pro Ala Asp Cys Ser Glu Gln Arg Thr Lys Thr Val
            755                 760                 765

Gln Gln Asn Ser Asp Asn Pro Ile Phe Asp Glu Thr Phe Glu Phe Gln
            770                 775                 780

Val Asn Leu Pro Glu Leu Ala Met Ile Arg Phe Val Val Leu Asp Asp
785                 790                 795                 800

Asp Tyr Ile Gly Asp Glu Phe Ile Gly Gln Tyr Thr Ile Pro Phe Glu
            805                 810                 815

Cys Leu Gln Pro Gly Tyr Arg His Val Pro Leu Arg Ser Phe Val Gly
            820                 825                 830

Asp Ile Met Glu His Val Thr Leu Phe Val His Ile Ala Ile Thr Asn
            835                 840                 845

Arg Ser Gly Gly Gly Lys Ala Gln Lys Arg Ser Leu Ser Val Arg Met
850                 855                 860

Gly Lys Lys Val Arg Glu Tyr Thr Met Leu Arg Asn Ile Gly Leu Lys
865                 870                 875                 880

Thr Ile Asp Asp Ile Phe Lys Ile Ala Val His Pro Leu Arg Glu Ala
            885                 890                 895

Ile Asp Met Arg Glu Asn Met Gln Asn Ala Ile Val Ser Ile Lys Glu
            900                 905                 910

Leu Cys Gly Leu Pro Pro Ile Ala Ser Leu Lys Gln Cys Leu Leu Thr
            915                 920                 925

Leu Ser Ser Arg Leu Ile Thr Ser Asp Asn Thr Pro Ser Val Ser Leu
930                 935                 940

Val Met Lys Asp Ser Phe Pro Tyr Leu Glu Pro Leu Gly Ala Ile Pro
945                 950                 955                 960

Asp Val Gln Lys Lys Met Leu Thr Ala Tyr Asp Leu Met Ile Gln Glu
            965                 970                 975

Ser Arg Phe Leu Ile Glu Met Ala Asp Thr Val Gln Glu Lys Ile Val
            980                 985                 990

Gln Cys Gln Lys Ala Gly Met Glu Phe His Glu Glu Leu His Asn Leu
            995                 1000                1005

Gly Ala Lys Glu Gly Leu Lys Gly Arg Lys Leu Asn Lys Ala Thr
            1010                1015                1020

Glu Ser Phe Ala Trp Asn Ile Thr Val Leu Lys Gly Gln Gly Asp
1025                1030                1035

Leu Leu Lys Asn Ala Lys Asn Glu Ala Ile Glu Asn Met Lys Gln
1040                1045                1050

Ile Gln Leu Ala Cys Leu Ser Cys Gly Leu Ser Lys Ala Pro Ser
1055                1060                1065

Ser Ser Ala Glu Ala Lys Ser Lys Arg Ser Leu Glu Ala Ile Glu
1070                1075                1080

Glu Lys Glu Ser Ser Glu Glu Asn Gly Lys Leu
1085                1090

<210> SEQ ID NO 13
<211> LENGTH: 984
<212> TYPE: PRT
<213> ORGANISM: Homo sapiens

<400> SEQUENCE: 13

Met Ala Leu Asp Tyr Leu Leu Leu Leu Leu Ala Ser Ala Val Ala
1               5                   10                  15

Ala Met Glu Glu Thr Leu Met Asp Thr Arg Thr Ala Thr Ala Glu Leu
            20                  25                  30

Gly Trp Thr Ala Asn Pro Ala Ser Gly Trp Glu Glu Val Ser Gly Tyr
            35                  40                  45

Asp Glu Asn Leu Asn Thr Ile Arg Thr Tyr Gln Val Cys Asn Val Phe
    50                  55                  60

Glu Pro Asn Gln Asn Asn Trp Leu Leu Thr Thr Phe Ile Asn Arg Arg
65                  70                  75                  80

Gly Ala His Arg Ile Tyr Thr Glu Met Arg Phe Thr Val Arg Asp Cys
                85                  90                  95

Ser Ser Leu Pro Asn Val Pro Gly Ser Cys Lys Glu Thr Phe Asn Leu
                100                 105                 110

Tyr Tyr Tyr Glu Thr Asp Ser Val Ile Ala Thr Lys Lys Ser Ala Phe
            115                 120                 125

Trp Ser Glu Ala Pro Tyr Leu Lys Val Asp Thr Ile Ala Ala Asp Glu
    130                 135                 140

Ser Phe Ser Gln Val Asp Phe Gly Gly Arg Leu Met Lys Val Asn Thr
145                 150                 155                 160

Glu Val Arg Ser Phe Gly Pro Leu Thr Arg Asn Gly Phe Tyr Leu Ala
                165                 170                 175

Phe Gln Asp Tyr Gly Ala Cys Met Ser Leu Leu Ser Val Arg Val Phe
            180                 185                 190

Phe Lys Lys Cys Pro Ser Ile Val Gln Asn Phe Ala Val Phe Pro Glu
        195                 200                 205

Thr Met Thr Gly Ala Glu Ser Thr Ser Leu Val Ile Ala Arg Gly Thr
    210                 215                 220

Cys Ile Pro Asn Ala Glu Glu Val Asp Val Pro Ile Lys Leu Tyr Cys
225                 230                 235                 240

Asn Gly Asp Gly Glu Trp Met Val Pro Ile Gly Arg Cys Thr Cys Lys
                245                 250                 255

Pro Gly Tyr Glu Pro Glu Asn Ser Val Ala Cys Lys Ala Cys Pro Ala
            260                 265                 270

Gly Thr Phe Lys Ala Ser Gln Glu Ala Glu Gly Cys Ser His Cys Pro
        275                 280                 285

Ser Asn Ser Arg Ser Pro Ala Glu Ala Ser Pro Ile Cys Thr Cys Arg
    290                 295                 300

-continued

Thr Gly Tyr Tyr Arg Ala Asp Phe Asp Pro Glu Val Ala Cys Thr
305                 310                 315                 320

Ser Val Pro Ser Gly Pro Arg Asn Val Ile Ser Ile Val Asn Glu Thr
            325                 330                 335

Ser Ile Ile Leu Glu Trp His Pro Pro Arg Glu Thr Gly Gly Arg Asp
            340                 345                 350

Asp Val Thr Tyr Asn Ile Ile Cys Lys Lys Cys Arg Ala Asp Arg Arg
            355                 360                 365

Ser Cys Ser Arg Cys Asp Asp Asn Val Glu Phe Val Pro Arg Gln Leu
        370                 375                 380

Gly Leu Thr Glu Cys Arg Val Ser Ile Ser Ser Leu Trp Ala His Thr
385                 390                 395                 400

Pro Tyr Thr Phe Asp Ile Gln Ala Ile Asn Gly Val Ser Ser Lys Ser
                405                 410                 415

Pro Phe Pro Pro Gln His Val Ser Val Asn Ile Thr Thr Asn Gln Ala
            420                 425                 430

Ala Pro Ser Thr Val Pro Ile Met His Gln Val Ser Ala Thr Met Arg
            435                 440                 445

Ser Ile Thr Leu Ser Trp Pro Gln Pro Glu Gln Pro Asn Gly Ile Ile
450                 455                 460

Leu Asp Tyr Glu Ile Arg Tyr Tyr Glu Lys Glu His Asn Glu Phe Asn
465                 470                 475                 480

Ser Ser Met Ala Arg Ser Gln Thr Asn Thr Ala Arg Ile Asp Gly Leu
            485                 490                 495

Arg Pro Gly Met Val Tyr Val Gln Val Arg Ala Arg Thr Val Ala
            500                 505                 510

Gly Tyr Gly Lys Phe Ser Gly Lys Met Cys Phe Gln Thr Leu Thr Asp
        515                 520                 525

Asp Asp Tyr Lys Ser Glu Leu Arg Glu Gln Leu Pro Leu Ile Ala Gly
        530                 535                 540

Ser Ala Ala Gly Val Val Phe Val Val Ser Leu Val Ala Ile Ser
545                 550                 555                 560

Ile Val Cys Ser Arg Lys Arg Ala Tyr Ser Lys Glu Ala Val Tyr Ser
                565                 570                 575

Asp Lys Leu Gln His Tyr Ser Thr Gly Arg Gly Ser Pro Gly Met Lys
            580                 585                 590

Ile Tyr Ile Asp Pro Phe Thr Tyr Glu Asp Pro Asn Glu Ala Val Arg
        595                 600                 605

Glu Phe Ala Lys Glu Ile Asp Val Ser Phe Val Lys Ile Glu Glu Val
        610                 615                 620

Ile Gly Ala Gly Glu Phe Gly Glu Val Tyr Lys Gly Arg Leu Lys Leu
625                 630                 635                 640

Pro Gly Lys Arg Glu Ile Tyr Val Ala Ile Lys Thr Leu Lys Ala Gly
            645                 650                 655

Tyr Ser Glu Lys Gln Arg Arg Asp Phe Leu Ser Glu Ala Ser Ile Met
            660                 665                 670

Gly Gln Phe Asp His Pro Asn Ile Ile Arg Leu Glu Gly Val Val Thr
            675                 680                 685

Lys Ser Arg Pro Val Met Ile Ile Thr Glu Phe Met Glu Asn Gly Ala
        690                 695                 700

Leu Asp Ser Phe Leu Arg Gln Asn Asp Gly Gln Phe Thr Val Ile Gln
705                 710                 715                 720

Leu Val Gly Met Leu Arg Gly Ile Ala Ala Gly Met Lys Tyr Leu Ala

```
                        725                 730                 735
Glu Met Asn Tyr Val His Arg Asp Leu Ala Ala Arg Asn Ile Leu Val
            740                 745                 750

Asn Ser Asn Leu Val Cys Lys Val Ser Asp Phe Gly Leu Ser Arg Tyr
            755                 760                 765

Leu Gln Asp Asp Thr Ser Asp Pro Thr Tyr Thr Ser Ser Leu Gly Gly
            770                 775                 780

Lys Ile Pro Val Arg Trp Thr Ala Pro Glu Ala Ile Ala Tyr Arg Lys
785                 790                 795                 800

Phe Thr Ser Ala Ser Asp Val Trp Ser Tyr Gly Ile Val Met Trp Glu
                    805                 810                 815

Val Met Ser Phe Gly Glu Arg Pro Tyr Trp Asp Met Ser Asn Gln Asp
                    820                 825                 830

Val Ile Asn Ala Ile Glu Gln Asp Tyr Arg Leu Pro Pro Pro Met Asp
                    835                 840                 845

Cys Pro Ala Ala Leu His Gln Leu Met Leu Asp Cys Trp Gln Lys Asp
            850                 855                 860

Arg Asn Ser Arg Pro Arg Phe Ala Glu Ile Val Asn Thr Leu Asp Lys
865                 870                 875                 880

Met Ile Arg Asn Pro Ala Ser Leu Lys Thr Val Ala Thr Ile Thr Ala
                    885                 890                 895

Val Pro Ser Gln Pro Leu Leu Asp Arg Ser Ile Pro Asp Phe Thr Ala
            900                 905                 910

Phe Thr Thr Val Asp Asp Trp Leu Ser Ala Ile Lys Met Val Gln Tyr
            915                 920                 925

Arg Asp Ser Phe Leu Thr Ala Gly Phe Thr Ser Leu Gln Leu Val Thr
930                 935                 940

Gln Met Thr Ser Glu Asp Leu Leu Arg Ile Gly Ile Thr Leu Ala Gly
945                 950                 955                 960

His Gln Lys Lys Ile Leu Asn Ser Ile His Ser Met Arg Val Gln Ile
                    965                 970                 975

Ser Gln Ser Pro Thr Ala Met Ala
            980

<210> SEQ ID NO 14
<211> LENGTH: 517
<212> TYPE: PRT
<213> ORGANISM: Homo sapiens

<400> SEQUENCE: 14

Met Asp Phe Arg Thr Ala Cys Glu Glu Thr Lys Thr Gly Ile Cys Leu
1               5                   10                  15

Leu Gln Asp Gly Asn Gln Glu Pro Phe Lys Val Arg Leu His Leu Ala
            20                  25                  30

Lys Asp Ile Leu Met Ile Gln Glu Gln Asp Val Ile Cys Val Ser Gly
            35                  40                  45

Glu Pro Phe Tyr Ser Gly Glu Arg Thr Val Thr Ile Arg Arg Gln Thr
            50                  55                  60

Val Gly Gly Phe Gly Leu Ser Ile Lys Gly Gly Ala Glu His Asn Ile
65                  70                  75                  80

Pro Val Val Val Ser Lys Ile Ser Lys Glu Gln Arg Ala Glu Leu Ser
                    85                  90                  95

Gly Leu Leu Phe Ile Gly Asp Ala Ile Leu Gln Ile Asn Gly Ile Asn
            100                 105                 110

Val Arg Lys Cys Arg His Glu Glu Val Val Gln Val Leu Arg Asn Ala
```

```
            115                 120                 125
Gly Glu Glu Val Thr Leu Thr Val Ser Phe Leu Lys Arg Ala Pro Ala
130                 135                 140

Phe Leu Lys Leu Pro Leu Asn Glu Asp Cys Ala Cys Ala Pro Ser Asp
145                 150                 155                 160

Gln Ser Ser Gly Thr Ser Ser Pro Leu Cys Asp Ser Gly Leu His Leu
                165                 170                 175

Asn Tyr His Pro Asn Asn Thr Asp Thr Leu Ser Cys Ser Ser Trp Pro
            180                 185                 190

Thr Ser Pro Gly Leu Arg Trp Glu Lys Arg Trp Cys Asp Leu Arg Leu
        195                 200                 205

Ile Pro Leu Leu His Ser Arg Phe Ser Gln Tyr Val Pro Gly Thr Asp
    210                 215                 220

Leu Ser Arg Gln Asn Ala Phe Gln Val Ile Ala Val Asp Gly Val Cys
225                 230                 235                 240

Thr Gly Ile Ile Gln Cys Leu Ser Ala Glu Asp Cys Val Asp Trp Leu
                245                 250                 255

Gln Ala Ile Ala Thr Asn Ile Ser Asn Leu Thr Lys His Asn Ile Lys
            260                 265                 270

Lys Ile Asn Arg Asn Phe Pro Val Asn Gln Gln Ile Val Tyr Met Gly
        275                 280                 285

Trp Cys Glu Ala Arg Glu Gln Asp Pro Leu Gln Asp Arg Val Tyr Ser
    290                 295                 300

Pro Thr Phe Leu Ala Leu Arg Gly Ser Cys Leu Tyr Lys Phe Leu Ala
305                 310                 315                 320

Pro Pro Val Thr Thr Trp Asp Trp Thr Arg Ala Glu Lys Thr Phe Ser
                325                 330                 335

Val Tyr Glu Ile Met Cys Lys Ile Leu Lys Asp Ser Asp Leu Leu Asp
            340                 345                 350

Arg Arg Lys Gln Cys Phe Thr Val Gln Ser Glu Ser Gly Glu Asp Leu
        355                 360                 365

Tyr Phe Ser Val Glu Leu Glu Ser Asp Leu Ala Gln Trp Glu Arg Ala
    370                 375                 380

Phe Gln Thr Ala Thr Phe Leu Glu Val Glu Arg Ile Gln Cys Lys Thr
385                 390                 395                 400

Tyr Ala Cys Val Leu Glu Ser His Leu Met Gly Leu Thr Ile Asp Phe
                405                 410                 415

Ser Thr Gly Phe Ile Cys Phe Asp Ala Ala Thr Lys Ala Val Leu Trp
            420                 425                 430

Arg Tyr Lys Phe Ser Gln Leu Lys Gly Ser Ser Asp Asp Gly Lys Ser
        435                 440                 445

Lys Ile Lys Phe Leu Phe Gln Asn Pro Asp Thr Lys Gln Ile Glu Ala
    450                 455                 460

Lys Glu Leu Glu Phe Ser Asn Leu Phe Ala Val Leu His Cys Ile His
465                 470                 475                 480

Ser Phe Phe Ala Ala Lys Val Ala Cys Leu Asp Pro Leu Phe Leu Gly
                485                 490                 495

Asn Gln Ala Thr Ala Ser Thr Ala Ala Ser Ser Ala Thr Thr Ser Lys
            500                 505                 510

Ala Lys Tyr Thr Thr
        515

<210> SEQ ID NO 15
<211> LENGTH: 810
```

-continued

```
<212> TYPE: PRT
<213> ORGANISM: Homo sapiens

<400> SEQUENCE: 15

Met Pro Met Asp Leu Ile Leu Val Val Trp Phe Cys Val Cys Thr Ala
1               5                   10                  15

Arg Thr Val Val Gly Phe Gly Met Asp Pro Asp Leu Gln Met Asp Ile
            20                  25                  30

Val Thr Glu Leu Asp Leu Val Asn Thr Thr Leu Gly Val Ala Gln Val
        35                  40                  45

Ser Gly Met His Asn Ala Ser Lys Ala Phe Leu Phe Gln Asp Ile Glu
    50                  55                  60

Arg Glu Ile His Ala Ala Pro His Val Ser Glu Lys Leu Ile Gln Leu
65                  70                  75                  80

Phe Arg Asn Lys Ser Glu Phe Thr Ile Leu Ala Thr Val Gln Gln Lys
                85                  90                  95

Pro Ser Thr Ser Gly Val Ile Leu Ser Ile Arg Glu Leu Glu His Ser
            100                 105                 110

Tyr Phe Glu Leu Glu Ser Ser Gly Leu Arg Asp Glu Ile Arg Tyr His
        115                 120                 125

Tyr Ile His Asn Gly Lys Pro Arg Thr Glu Ala Leu Pro Tyr Arg Met
    130                 135                 140

Ala Asp Gly Gln Trp His Lys Val Ala Leu Ser Val Ser Ala Ser His
145                 150                 155                 160

Leu Leu Leu His Val Asp Cys Asn Arg Ile Tyr Glu Arg Val Ile Asp
                165                 170                 175

Pro Pro Asp Thr Asn Leu Pro Pro Gly Ile Asn Leu Trp Leu Gly Gln
            180                 185                 190

Arg Asn Gln Lys His Gly Leu Phe Lys Gly Ile Ile Gln Asp Gly Lys
        195                 200                 205

Ile Ile Phe Met Pro Asn Gly Tyr Ile Thr Gln Cys Pro Asn Leu Asn
    210                 215                 220

His Thr Cys Pro Thr Cys Ser Asp Phe Leu Ser Leu Val Gln Gly Ile
225                 230                 235                 240

Met Asp Leu Gln Glu Leu Leu Ala Lys Met Thr Ala Lys Leu Asn Tyr
                245                 250                 255

Ala Glu Thr Arg Leu Ser Gln Leu Glu Asn Cys His Cys Glu Lys Thr
            260                 265                 270

Cys Gln Val Ser Gly Leu Leu Tyr Arg Asp Gln Asp Ser Trp Val Asp
        275                 280                 285

Gly Asp His Cys Arg Asn Cys Thr Cys Lys Ser Gly Ala Val Glu Cys
    290                 295                 300

Arg Arg Met Ser Cys Pro Pro Leu Asn Cys Ser Pro Asp Ser Leu Pro
305                 310                 315                 320

Val His Ile Ala Gly Gln Cys Cys Lys Val Cys Arg Pro Lys Cys Ile
                325                 330                 335

Tyr Gly Gly Lys Val Leu Ala Glu Gly Gln Arg Ile Leu Thr Lys Ser
            340                 345                 350

Cys Arg Glu Cys Arg Gly Gly Val Leu Val Lys Ile Thr Glu Met Cys
        355                 360                 365

Pro Pro Leu Asn Cys Ser Glu Lys Asp His Ile Leu Pro Glu Asn Gln
    370                 375                 380

Cys Cys Arg Val Cys Arg Gly His Asn Phe Cys Ala Glu Gly Pro Lys
385                 390                 395                 400
```

```
Cys Gly Glu Asn Ser Glu Cys Lys Asn Trp Asn Thr Lys Ala Thr Cys
                405                 410                 415
Glu Cys Lys Ser Gly Tyr Ile Ser Val Gln Gly Asp Ser Ala Tyr Cys
            420                 425                 430
Glu Asp Ile Asp Glu Cys Ala Ala Lys Met His Tyr Cys His Ala Asn
        435                 440                 445
Thr Val Cys Val Asn Leu Pro Gly Leu Tyr Arg Cys Asp Cys Val Pro
    450                 455                 460
Gly Tyr Ile Arg Val Asp Asp Phe Ser Cys Thr Glu His Asp Glu Cys
465                 470                 475                 480
Gly Ser Gly Gln His Asn Cys Asp Glu Asn Ala Ile Cys Thr Asn Thr
                485                 490                 495
Val Gln Gly His Ser Cys Thr Cys Lys Pro Gly Tyr Val Gly Asn Gly
            500                 505                 510
Thr Ile Cys Arg Ala Phe Cys Glu Glu Gly Cys Arg Tyr Gly Gly Thr
        515                 520                 525
Cys Val Ala Pro Asn Lys Cys Val Cys Pro Ser Gly Phe Thr Gly Ser
    530                 535                 540
His Cys Glu Lys Asp Ile Asp Glu Cys Ser Glu Gly Ile Ile Glu Cys
545                 550                 555                 560
His Asn His Ser Arg Cys Val Asn Leu Pro Gly Trp Tyr His Cys Glu
                565                 570                 575
Cys Arg Ser Gly Phe His Asp Asp Gly Thr Tyr Ser Leu Ser Gly Glu
            580                 585                 590
Ser Cys Ile Asp Ile Asp Glu Cys Ala Leu Arg Thr His Thr Cys Trp
        595                 600                 605
Asn Asp Ser Ala Cys Ile Asn Leu Ala Gly Gly Phe Asp Cys Leu Cys
    610                 615                 620
Pro Ser Gly Pro Ser Cys Ser Gly Asp Cys Pro His Glu Gly Gly Leu
625                 630                 635                 640
Lys His Asn Gly Gln Val Trp Thr Leu Lys Glu Asp Arg Cys Ser Val
                645                 650                 655
Cys Ser Cys Lys Asp Gly Lys Ile Phe Cys Arg Arg Thr Ala Cys Asp
            660                 665                 670
Cys Gln Asn Pro Ser Ala Asp Leu Phe Cys Cys Pro Glu Cys Asp Thr
        675                 680                 685
Arg Val Thr Ser Gln Cys Leu Asp Gln Asn Gly His Lys Leu Tyr Arg
    690                 695                 700
Ser Gly Asp Asn Trp Thr His Ser Cys Gln Gln Cys Arg Cys Leu Glu
705                 710                 715                 720
Gly Glu Val Asp Cys Trp Pro Leu Thr Cys Pro Asn Leu Ser Cys Glu
                725                 730                 735
Tyr Thr Ala Ile Leu Glu Gly Glu Cys Cys Pro Arg Cys Val Ser Asp
            740                 745                 750
Pro Cys Leu Ala Asp Asn Ile Thr Tyr Asp Ile Arg Lys Thr Cys Leu
        755                 760                 765
Asp Ser Tyr Gly Val Ser Arg Leu Ser Gly Ser Val Trp Thr Met Ala
    770                 775                 780
Gly Ser Pro Cys Thr Thr Cys Lys Cys Lys Asn Gly Arg Val Cys Cys
785                 790                 795                 800
Ser Val Asp Phe Glu Cys Leu Gln Asn Asn
                805                 810

<210> SEQ ID NO 16
```

```
<211> LENGTH: 816
<212> TYPE: PRT
<213> ORGANISM: Homo sapiens

<400> SEQUENCE: 16

Met Glu Ser Arg Val Leu Leu Arg Thr Phe Cys Leu Ile Phe Gly Leu
1               5                   10                  15

Gly Ala Val Trp Gly Leu Gly Val Asp Pro Ser Leu Gln Ile Asp Val
            20                  25                  30

Leu Thr Glu Leu Glu Leu Gly Glu Ser Thr Thr Gly Val Arg Gln Val
        35                  40                  45

Pro Gly Leu His Asn Gly Thr Lys Ala Phe Leu Phe Gln Asp Thr Pro
    50                  55                  60

Arg Ser Ile Lys Ala Ser Thr Ala Thr Ala Glu Gln Phe Phe Gln Lys
65                  70                  75                  80

Leu Arg Asn Lys His Glu Phe Thr Ile Leu Val Thr Leu Lys Gln Thr
                85                  90                  95

His Leu Asn Ser Gly Val Ile Leu Ser Ile His His Leu Asp His Arg
            100                 105                 110

Tyr Leu Glu Leu Glu Ser Ser Gly His Arg Asn Glu Val Arg Leu His
        115                 120                 125

Tyr Arg Ser Gly Ser His Arg Pro His Thr Glu Val Phe Pro Tyr Ile
    130                 135                 140

Leu Ala Asp Asp Lys Trp His Lys Leu Ser Leu Ala Ile Ser Ala Ser
145                 150                 155                 160

His Leu Ile Leu His Ile Asp Cys Asn Lys Ile Tyr Glu Arg Val Val
                165                 170                 175

Glu Lys Pro Ser Thr Asp Leu Pro Leu Gly Thr Thr Phe Trp Leu Gly
            180                 185                 190

Gln Arg Asn Asn Ala His Gly Tyr Phe Lys Gly Ile Met Gln Asp Val
        195                 200                 205

Gln Leu Leu Val Met Pro Gln Gly Phe Ile Ala Gln Cys Pro Asp Leu
    210                 215                 220

Asn Arg Thr Cys Pro Thr Cys Asn Asp Phe His Gly Leu Val Gln Lys
225                 230                 235                 240

Ile Met Glu Leu Gln Asp Ile Leu Ala Lys Thr Ser Ala Lys Leu Ser
                245                 250                 255

Arg Ala Glu Gln Arg Met Asn Arg Leu Asp Gln Cys Tyr Cys Glu Arg
            260                 265                 270

Thr Cys Thr Met Lys Gly Thr Thr Tyr Arg Glu Phe Glu Ser Trp Ile
        275                 280                 285

Asp Gly Cys Lys Asn Cys Thr Cys Leu Asn Gly Thr Ile Gln Cys Glu
    290                 295                 300

Thr Leu Ile Cys Pro Asn Pro Asp Cys Pro Leu Lys Ser Ala Leu Ala
305                 310                 315                 320

Tyr Val Asp Gly Lys Cys Cys Lys Glu Cys Lys Ser Ile Cys Gln Phe
                325                 330                 335

Gln Gly Arg Thr Tyr Phe Glu Gly Glu Arg Asn Thr Val Tyr Ser Ser
            340                 345                 350

Ser Gly Val Cys Val Leu Tyr Glu Cys Lys Asp Gln Thr Met Lys Leu
        355                 360                 365

Val Glu Ser Ser Gly Cys Pro Ala Leu Asp Cys Pro Glu Ser His Gln
    370                 375                 380

Ile Thr Leu Ser His Ser Cys Cys Lys Val Cys Lys Gly Tyr Asp Phe
385                 390                 395                 400
```

-continued

Cys Ser Glu Arg His Asn Cys Met Glu Asn Ser Ile Cys Arg Asn Leu
                405                 410                 415
Asn Asp Arg Ala Val Cys Ser Cys Arg Asp Gly Phe Arg Ala Leu Arg
                420                 425                 430
Glu Asp Asn Ala Tyr Cys Glu Asp Ile Asp Glu Cys Ala Glu Gly Arg
                435                 440                 445
His Tyr Cys Arg Glu Asn Thr Met Cys Val Asn Thr Pro Gly Ser Phe
                450                 455                 460
Met Cys Ile Cys Lys Thr Gly Tyr Ile Arg Ile Asp Asp Tyr Ser Cys
465                 470                 475                 480
Thr Glu His Asp Glu Cys Ile Thr Asn Gln His Asn Cys Asp Glu Asn
                    485                 490                 495
Ala Leu Cys Phe Asn Thr Val Gly Gly His Asn Cys Val Cys Lys Pro
                500                 505                 510
Gly Tyr Thr Gly Asn Gly Thr Thr Cys Lys Ala Phe Cys Lys Asp Gly
                515                 520                 525
Cys Arg Asn Gly Gly Ala Cys Ile Ala Ala Asn Val Cys Ala Cys Pro
                530                 535                 540
Gln Gly Phe Thr Gly Pro Ser Cys Glu Thr Asp Ile Asp Glu Cys Ser
545                 550                 555                 560
Asp Gly Phe Val Gln Cys Asp Ser Arg Ala Asn Cys Ile Asn Leu Pro
                    565                 570                 575
Gly Trp Tyr His Cys Glu Cys Arg Asp Gly Tyr His Asp Asn Gly Met
                580                 585                 590
Phe Ser Pro Ser Gly Glu Ser Cys Glu Asp Ile Asp Glu Cys Gly Thr
                595                 600                 605
Gly Arg His Ser Cys Ala Asn Asp Thr Ile Cys Phe Asn Leu Asp Gly
                610                 615                 620
Gly Tyr Asp Cys Arg Cys Pro His Gly Lys Asn Cys Thr Gly Asp Cys
625                 630                 635                 640
Ile His Asp Gly Lys Val Lys His Asn Gly Gln Ile Trp Val Leu Glu
                    645                 650                 655
Asn Asp Arg Cys Ser Val Cys Ser Cys Gln Asn Gly Phe Val Met Cys
                660                 665                 670
Arg Arg Met Val Cys Asp Cys Glu Asn Pro Thr Val Asp Leu Phe Cys
                675                 680                 685
Cys Pro Glu Cys Asp Pro Arg Leu Ser Ser Gln Cys Leu His Gln Asn
                690                 695                 700
Gly Glu Thr Leu Tyr Asn Ser Gly Asp Thr Trp Val Gln Asn Cys Gln
705                 710                 715                 720
Gln Cys Arg Cys Leu Gln Gly Glu Val Asp Cys Trp Pro Leu Pro Cys
                    725                 730                 735
Pro Asp Val Glu Cys Glu Phe Ser Ile Leu Pro Glu Asn Glu Cys Cys
                740                 745                 750
Pro Arg Cys Val Thr Asp Pro Cys Gln Ala Asp Thr Ile Arg Asn Asp
                755                 760                 765
Ile Thr Lys Thr Cys Leu Asp Glu Met Asn Val Val Arg Phe Thr Gly
                770                 775                 780
Ser Ser Trp Ile Lys His Gly Thr Glu Cys Thr Leu Cys Gln Cys Lys
785                 790                 795                 800
Asn Gly His Ile Cys Cys Ser Val Asp Pro Gln Cys Leu Gln Glu Leu
                    805                 810                 815

```
<210> SEQ ID NO 17
<211> LENGTH: 24
<212> TYPE: DNA
<213> ORGANISM: Artificial Sequence
<220> FEATURE:
<223> OTHER INFORMATION: Nucleic Acid PCR Primer

<400> SEQUENCE: 17
gaagttcaat gtcggagttt ctga                                            24

<210> SEQ ID NO 18
<211> LENGTH: 21
<212> TYPE: DNA
<213> ORGANISM: Artificial Sequence
<220> FEATURE:
<223> OTHER INFORMATION: Nucleic Acid PCR Primer

<400> SEQUENCE: 18
gcatcacagg gaagaccgtg t                                               21

<210> SEQ ID NO 19
<211> LENGTH: 18
<212> TYPE: DNA
<213> ORGANISM: Artificial Sequence
<220> FEATURE:
<223> OTHER INFORMATION: Nucleic Acid PCR Primer

<400> SEQUENCE: 19
cttagaggga caagtggc                                                   18

<210> SEQ ID NO 20
<211> LENGTH: 20
<212> TYPE: DNA
<213> ORGANISM: Artificial Sequence
<220> FEATURE:
<223> OTHER INFORMATION: Nucleic Acid PCR Primer

<400> SEQUENCE: 20
acgctgagcc agtcagtgta                                                 20
```